United States Patent
Ono et al.

(10) Patent No.: US 9,181,229 B2
(45) Date of Patent: Nov. 10, 2015

(54) AZOLE DERIVATIVE

(75) Inventors: Naoya Ono, Toshima-ku (JP); Shoichi Kuroda, Toshima-ku (JP); Yoshihisa Shirasaki, Toshima-ku (JP); Tetsuo Takayama, Toshima-ku (JP); Yoshinori Sekiguchi, Toshima-ku (JP); Fumihito Ushiyama, Toshima-ku (JP); Yusuke Oka, Toshima-ku (JP)

(73) Assignee: TAISHO PHARMACEUTICAL CO., LTD., Tokyo (JP)

( * ) Notice: Subject to any disclaimer, the term of this patent is extended or adjusted under 35 U.S.C. 154(b) by 92 days.

(21) Appl. No.: 14/004,997

(22) PCT Filed: Mar. 15, 2012

(86) PCT No.: PCT/JP2012/056624
§ 371 (c)(1),
(2), (4) Date: Sep. 13, 2013

(87) PCT Pub. No.: WO2012/124750
PCT Pub. Date: Sep. 20, 2012

(65) Prior Publication Data
US 2013/0345419 A1    Dec. 26, 2013

(30) Foreign Application Priority Data
Mar. 15, 2011    (JP) .................................. 2011-056149

(51) Int. Cl.
*C07D 413/04* (2006.01)
*C07D 403/04* (2006.01)
*C07D 417/04* (2006.01)
*C07D 413/14* (2006.01)

(52) U.S. Cl.
CPC ............ *C07D 413/04* (2013.01); *C07D 403/04* (2013.01); *C07D 413/14* (2013.01); *C07D 417/04* (2013.01)

(58) Field of Classification Search
None
See application file for complete search history.

(56) References Cited

U.S. PATENT DOCUMENTS

2010/0022604 A1    1/2010    Nakao et al.

FOREIGN PATENT DOCUMENTS

| EP | 0 423 714 A2 | 4/1991 |
|---|---|---|
| JP | 2925285 B2 | 7/1999 |
| JP | 2001-247569 A | 9/2001 |
| JP | 2004-123556 A | 4/2004 |
| JP | 2004-123557 A | 4/2004 |
| JP | 2004123556 | * 4/2004 |
| WO | 92/19593 A1 | 11/1992 |
| WO | 96/40633 A1 | 12/1996 |
| WO | 98/55090 A1 | 12/1998 |
| WO | 99/45006 A1 | 9/1999 |
| WO | 99/62511 A1 | 12/1999 |
| WO | 9962880 | 12/1999 |
| WO | 00/05231 A1 | 2/2000 |
| WO | 00/27811 A1 | 5/2000 |
| WO | 0104116 | 1/2001 |
| WO | 01/42245 A1 | 6/2001 |
| WO | 2008/075735 A1 | 6/2008 |

OTHER PUBLICATIONS

Communication for EP 12757646.0 dated Jul. 17, 2014, with Supplementary European Search Report dated Jul. 9, 2014.
Yamamoto et al., "Stimulation of Hair Growth by Topical Application of FK506, a Potent Immunosuppressive Agent", Journal Investigative Dermatology, Feb. 1994, pp. 160-164, vol. 102, No. 2.
(Continued)

*Primary Examiner* — Kamal Saeed
(74) *Attorney, Agent, or Firm* — Sughrue Mion, PLLC

(57) ABSTRACT

Provided are novel compounds that bind to FKBP12 or pharmaceutically acceptable salts thereof, as well as new therapeutics useful in the prevention or treatment of alopecia which comprise those compounds or pharmaceutically acceptable salts thereof. Specifically, compounds represented by formula (1)

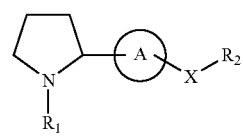

(1)

[where $R_1$ represents either the following formula (2) or (3)]

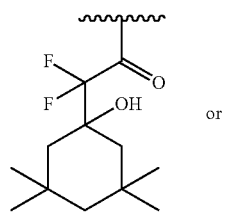

(2)

or

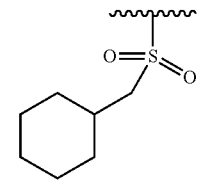

(3)

or pharmaceutically acceptable salts thereof are provided.

16 Claims, 2 Drawing Sheets

(56) References Cited

OTHER PUBLICATIONS

Freyschmidt-Paul et al., "Treatment of alopecia areata in C3H/HeJ mice with the topical immunosuppressant FK506 (Tacrolimus)", European Journal of Dermatology, Sep.-Oct. 2001, pp. 405-409, vol. 11, No. 5.

K. J. McElwee et al., "Topical FK506: a potent immunotherapy for alopecia areata? Studies using the Dundee experimental bald rat model", British Journal of Dermatology, 1997, vol. 137, pp. 491-497.

Hong Jiang et al., "Induction of Anagen in Telogen Mouse Skin by Topical Application of FK506, a Potent Immunosuppressant", Journal Investigative Dermatology, Apr. 1995, pp. 523-525, vol. 104, No. 4.

Maurer et al., "Hair Growth Modulation by Topical Immunophilin Ligands", American Journal of Pathology, Apr. 1997, pp. 1433-1441, vol. 150, No. 4.

International Search Report of PCT/JP2012/056624 dated Apr. 17, 2012.

* cited by examiner

AZOLE DERIVATIVE

CROSS REFERENCE TO RELATED APPLICATIONS

This is a National Stage of International Application No. PCT/JP2012/056624 filed Mar. 15, 2012, claiming priority based on Japanese Patent Application No. 2011-056149 filed Mar. 15, 2011, the contents of all of which are incorporated herein by reference in their entirety.

TECHNICAL FIELD

The present invention relates to novel compounds that bind to FKBP12 or pharmaceutically acceptable salts thereof, as well as agents for preventing or treating alopecia that contain such novel compounds or pharmaceutically acceptable salts thereof as an active ingredient.

BACKGROUND ART

Alopecia manifests itself in various types including male pattern alopecia, alopecia senilis, alopecia areata, and alopecia in postmenopausal women. While alopecia is not life-threatening in many cases, the disease is cosmetically distressing and often involves mental pain; under the circumstances, effective agents for preventing or treating alopecia are desired.

Hairs are born again through three stages, the anagen, catagen, and telogen phases (hair cycle). One hair cycle usually takes a period of two to seven years to complete and if something abnormal occurs to shorten this period, hair growth is arrested before reaching maturity. As a consequence, more hairs will fall out to result in a lower hair density or the thickness per hair will decrease. Factors that upset the rhythm of hair cycle include androgens such as testosterone and dihydrotestosterone, radiation, medicaments such as anticancer drugs, aging, and stress.

Studies using many diverse compounds are being made with a view to creating therapeutics for alopecia, and the immunosuppressant FK506 (tacrolimus), for example, has been reported to have a recognizable hair-development stimulating effect in a plurality of animal models (see Patent Document 1 and Non-Patent Document 1.) The action of FK506 has been confirmed in models of alopecia areata which is considered an autoimmune disease (see Non-Patent Documents 2 and 3), as well as in hair development tests using normal mice and models of alopecia medicamentosa (see Non-Patent Documents 4 and 5.) However, due to its immunosuppressing action, FK506 has high risk for side-effects, so there is desired a safer compound that is effective as a therapeutic for alopecia without presenting the immunosuppressing action.

A plurality of compounds that bind to immunophilin FKBP12 (an FK506 binding protein with a molecular weight of 12 kDa) without exerting the immunosuppressing action have recently been found (see Patent Documents 2-10.) Some of those derivatives have been disclosed to show a hair-development stimulating action (see Patent Documents 11 and 12.) Other derivatives, however, have not been reported to show any hair-development stimulating action and much remains unclear about the relationship between the activity of binding to immunophilin FKBP12 and the hair-development stimulating activity. What is more, the reported FKBP12 binding compounds are not disclosed to have the same azole structures as specified in the present invention.

CITATION LIST

Patent Literature

Patent Document 1: Japanese Patent No. 2925285
Patent Document 2: WO 1996/040633
Patent Document 3: WO 1992/019593
Patent Document 4: WO 2000/027811
Patent Document 5: WO 1999/062511
Patent Document 6: WO 1999/045006
Patent Document 7: WO 2000/005231
Patent Document 8: WO 2001/042245
Patent Document 9: JP 2004-123556 A
Patent Document 10: JP 2004-123557 A
Patent Document 11: WO 98/55090
Patent Document 12: WO 2008/075735

Non-Patent Literature

Non-Patent Document 1: Yamamoto et al., "J. Invest. Dermatol.", 102, 160-164, 1994
Non-Patent Document 2: Freyschmidt-Paul et al., "Eur. J. Dermatol.", 11, 405-409, 2001
Non-Patent Document 3: McElwee et al., "Br. J. Dermatol.", 137, 491-497, 1997
Non-Patent Document 4: Jianga et al., "J. Invest. Dermatol.", 104, 523-525, 1995
Non-Patent Document 5: Maurer et al., "Am. J. Pathol.", 150, 1433-1441, 1997

SUMMARY OF INVENTION

Technical Problem

An object of the present invention is to find novel compounds that bind to FKBP12 or pharmaceutically acceptable salts thereof and provide new therapeutics useful in preventing or treating alopecia.

Solution to Problem

The present inventors found that compounds represented by the following formula (1) or pharmaceutically acceptable salts thereof can solve the aforementioned problem and this finding has led to the accomplishment of the present invention.

Accordingly, the present invention relates to:

(I) A compound represented by formula (1)

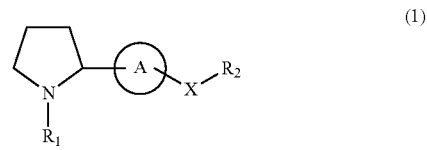

(1)

[where R₁ represents either the following formula (2) or (3)

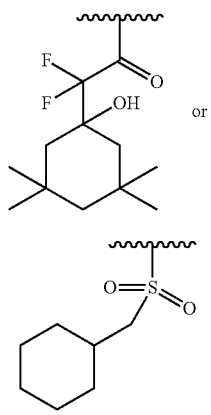

ring A represents either one of the rings represented by the following formula (4)

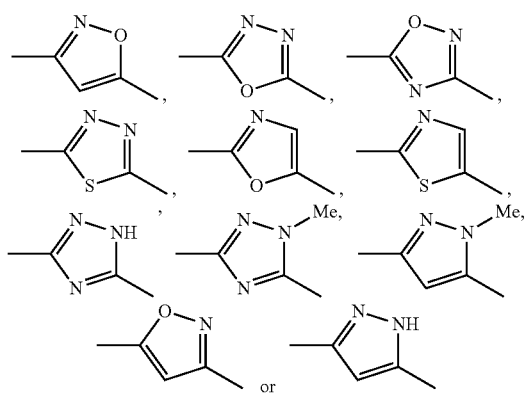

X represents —(CH₂)ₘ—X₁—(CH₂)ₙ—;
X₁ represents a bond, —O—, —NRᵃC(=O)—, —C(=O)NRᵇ—, —NRᶜS(=O)₂—, or —S(=O)₂NRᵈ—;
Rᵃ, Rᵇ, Rᶜ, and Rᵈ which may be the same or different each represent a hydrogen atom or a C₁₋₆ alkyl group;
m and n which may be the same or different each represent an integer of 0-3;
R₂ represents an aryl group, a heteroaryl group (said aryl or heteroaryl group may be substituted by 1-3 substituent groups selected from the group consisting of a halogen atom, a C₁₋₆ alkyl group, and a C₁₋₆ alkoxy group (said C₁₋₆ alkyl group or C₁₋₆ alkoxy group may be substituted by 1-3 substituent groups selected from the group consisting of a halogen atom and a hydroxy group)), a 1,3-benzodioxolanyl group, an indolyl group, a morpholyl group, a hydroxy group, a C₁₋₆ alkyl group (said C₁₋₆ alkyl group may be substituted by 1-2 hydroxy groups), an amino group, a mono-C₁₋₆ alkylamino group, a di-C₁₋₆ alkylamino group, a C₁₋₆ alkoxy group, a C₁₋₆ alkylsulfonyloxy group, a pyridonyl group, or a pyrimidinonyl group] or a pharmaceutically acceptable salts thereof;

(I') The compound or pharmaceutically acceptable salt thereof according to (I), wherein R₂ represents an aryl group, a heteroaryl group (said aryl or heteroaryl group may be substituted by 1-3 substituent groups selected from the group consisting of a C₁₋₆ alkyl group and a C₁₋₆ alkoxy group (said C₁₋₆ alkyl group or C₁₋₆ alkoxy group may be substituted by 1-3 substituent groups selected from the group consisting of a halogen atom and a hydroxy group)), a 1,3-benzodioxolanyl group, an indolyl group, a morpholyl group, a hydroxy group, a C₁₋₆ alkyl group (said C₁₋₆ alkyl group may be substituted by 1-2 hydroxy groups), an amino group, a mono-C₁₋₆ alkylamino group, a di-C₁₋₆ alkylamino group, a C₁₋₆ alkoxy group, or a C₁₋₆ alkylsulfonyloxy group;

(II) The compound or pharmaceutically acceptable salt thereof according to (I) or (I'), wherein X is a bond, —CH₂O—, —CH₂—, —(CH₂)₂—, —(CH₂)₃—, —O—, —CH₂—NHC(=O)—, —CH₂—NHC(=O)—CH₂—, or —CH₂—NHS(=O)₂—;

(III) The compound or pharmaceutically acceptable salt thereof according to (I) or (I'), wherein X is —CH₂O— or —CH₂—;

(IV) The compound or pharmaceutically acceptable salt thereof according to any one of (I) to (III) and (I'), wherein R₁ is formula (2);

(V) The compound or pharmaceutically acceptable salt thereof according to any one of (I) to (IV) and (I'), wherein ring A is either one of the rings of the following formula (5):

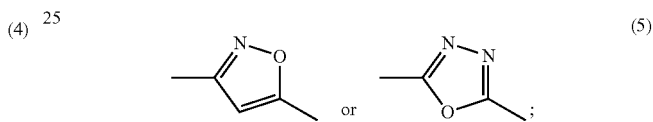

(VI) The compound or pharmaceutically acceptable salt thereof according to any one of (I) to (V) and (I'), wherein R₂ is a phenyl group, a pyridyl group, a pyridazinyl group or a pyrimidyl group (said phenyl group, pyridyl group or pyrimidyl group may be substituted by 1-3 halogen atoms or methoxy groups), a pyridonyl group, or a pyrimidinonyl group;

(VII) The compound or pharmaceutically acceptable salt thereof according to (VI), wherein R₂ is a phenyl group or a pyridyl group (said phenyl group or pyridyl group may be substituted by 1-3 methoxy groups);

(VIII) The compound according to (I), which is
(S)-1-(2-(5-((3,4-dimethoxyphenoxy)methyl)isoxazol-3-yl)pyrrolidin-1-yl)-2,2-difluoro-2-(1-hydroxy-3,3,5,5-tetramethylcyclohexyl)ethanone,
(S)-2,2-difluoro-2-(1-hydroxy-3,3,5,5-tetramethylcyclohexyl)-1-(2-(5-((pyridin-3-yloxy)methyl)isoxazol-3-yl)pyrrolidin-1-yl)ethanone,
(S)-2,2-difluoro-2-(1-hydroxy-3,3,5,5-tetramethylcyclohexyl)-1-(2-(5-((3,4,5-trimethoxyphenoxy)methyl)isoxazol-3-yl)pyrrolidin-1-yl)ethanone,
(S)—N-((3-(1-(2,2-difluoro-2-(1-hydroxy-3,3,5,5-tetramethylcyclohexyl)acetyl)pyrrolidin-2-yl)isoxazol-5-yl)methyl)benzamide,
(S)—N-((3-(1-(2,2-difluoro-2-(1-hydroxy-3,3,5,5-tetramethylcyclohexyl)acetyl)pyrrolidin-2-yl)isoxazol-5-yl)methyl)benzenesulfonamide,
(S)-1-(2-(5-((dimethylamino)methyl)isoxazol-3-yl)pyrrolidin-1-yl)-2,2-difluoro-2-(1-hydroxy-3,3,5,5-tetramethylcyclohexyl)ethanone,
(S)-3-(1-((cyclohexylmethyl)sulfonyl)pyrrolidin-2-yl)-5-(3,4-dimethoxyphenoxy)methyl)isoxazole,
(S)-1-(2-(5-((3,4-dimethoxyphenoxy)methyl)-1,3,4-oxadiazol-2-yl)pyrrolidin-1-yl)-2,2-difluoro-2-(1-hydroxy-3,3,5,5-tetramethylcyclohexyl)ethanone,
(S)-2,2-difluoro-2-(1-hydroxy-3,3,5,5-tetramethylcyclohexyl)-1-(2-(5-(phenoxymethyl)-1,3,4-oxadiazol-2-yl)pyrrolidin-1-yl)ethanone, (S)—N-((5-(1-(2,2-difluoro-2-(1-hydroxy-3,3,5,5-tetramethylcyclohexyl)acetyl)pyrrolidin-2-yl)-1,3,4-oxadiazol-2-yl)methyl)benzamide,
(S)-1-(2-(5-((dimethylamino)methyl)-1,3,4-oxadiazol-2-yl)pyrrolidin-1-yl)-2,2-difluoro-2-(1-hydroxy-3,3,5,5-tetramethylcyclohexyl)ethanone,
(S)-1-(2-(3-((3,4-dimethoxyphenoxy)methyl)-1,2,4-oxadiazol-5-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)-1-methyl-1H-pyrazol-3-yl)pyrrolidin-1-yl)-2,2-difluoro-2-(1-hydroxy-3,3,5,5-tetramethylcyclohexyl)ethanone,
(S)-1-(2-(3-((3,4-dimethoxyphenoxy)methyl)isoxazol-5-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)-1H-pyrazol-3-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)-1,3,4-thiadiazol-2-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)-4H-1,2,4-triazol-3-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)-1-methyl-1H-1,2,4-triazol-3-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)oxazol-2-yl)pyrrolidin-1-yl)-2,2-difluoro-2-(1-hydroxy-3,3,5,5-tetramethylcyclohexyl)ethanone,
(S)-1-(2-(5-((3,4-dimethoxyphenoxy)methyl)thiazol-2-yl)pyrrolidin-1-yl)-2,2-difluoro-2-(1-hydroxy-3,3,5,5-tetramethylcyclohexyl)ethanone,
(S)-2,2-difluoro-2-(1-hydroxy-3,3,5,5-tetramethylcyclohexyl)-1-(2-(5-(phenoxymethyl)isoxazol-3-yl)pyrrolidin-1-yl)ethanone,
(S)-2,2-difluoro-2-(1-hydroxy-3,3,5,5-tetramethylcyclohexyl)-1-(2-(5-((pyrimidin-5-yloxy)methyl)isoxazol-3-yl)pyrrolidin-1-yl)ethanone,
(S)-1-((3-(1-(2,2-difluoro-2-(1-hydroxy-3,3,5,5-tetramethylcyclohexyl)acetyl)pyrrolidin-2-yl)isoxazol-5-yl)methyl)pyrimidin-4(1H)-one,
(S)-2,2-difluoro-2-(1-hydroxy-3,3,5,5-tetramethylcyclohexyl)-1-(2-(5-((pyrimidin-4-yloxy)methyl)isoxazol-3-yl)pyrrolidin-1-yl)ethanone,
(S)-2,2-difluoro-1-(2-(5-((3-fluorophenoxy)methyl)isoxazol-3-yl)pyrrolidin-1-yl)-2-(1-hydroxy-3,3,5,5-tetramethylcyclohexyl)ethanone, or
(S)-1-((3-(1-(2,2-difluoro-2-(1-hydroxy-3,3,5,5-tetramethylcyclohexyl)acetyl)pyrrolidin-2-yl)isoxazol-5-yl)methyl)pyridin-4(1H)-one, or
a pharmaceutically acceptable salt thereof;
(IX) A pharmaceutical comprising as an active ingredient the compound or pharmaceutically acceptable salt thereof according to any one of (I) to (VIII) and (I'); and
(X) An agent for preventing or treating alopecia which comprises as an active ingredient the compound or pharmaceutically acceptable salt thereof according to any one of (I) to (VIII) and (I').

Advantageous Effects of Invention

The compounds of the present invention and pharmaceutically acceptable salts thereof bound to FKBP12 and inhibited its peptidyl-prolyl isomerase (rotamase) activity. In addition, the compounds and pharmaceutically acceptable salts thereof had such high solubility that they showed profiles preferred for external use. Moreover, the compounds and pharmaceutically acceptable salts thereof showed an outstanding hair-development stimulating action.

The compounds of the present invention and pharmaceutically acceptable salts thereof do not markedly suppress the protein phosphatase calcineurin, so they have no serious immunosuppressing activity. Consequently, it is expected that preparations containing the compounds or pharmaceutically acceptable salts thereof exhibit high safety feature when used as agents for preventing or treating alopecia.

DESCRIPTION OF EMBODIMENTS

Figure 1:
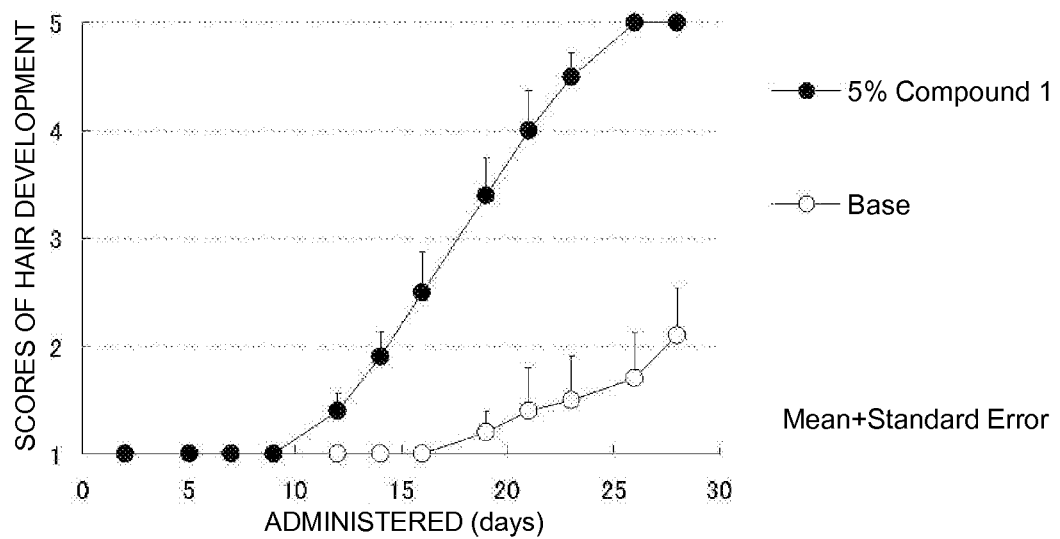
FIG. 1 shows the hair development stimulating effect of Compound 1 in shaven mouse models.

The following are the definitions of several important terms as used in this specification.

The term "halogen atom" means a fluorine atom, a chlorine atom, a bromine atom, or an iodine atom.

The term "$C_{1-6}$ alkyl group" means a straight or branched alkyl group having 1 to 6 carbon atoms and examples include a methyl group, an ethyl group, a propyl group, a butyl group, a pentyl group, a hexyl group, an isopropyl group, an isobutyl group, a tert-butyl group, a sec-butyl group, an isopentyl group, a neopentyl group, a tert-pentyl group, a 1,2-dimethylpropyl group, etc.

The term "$C_{1-6}$ alkoxy group" means a straight or branched alkoxy group having 1 to 6 carbon atoms and examples include a methoxy group, an ethoxy group, a propoxy group, a butoxy group, a pentyloxy group, a hexyloxy group, an isopropoxy group, an isobutoxy group, a tert-butoxy group, a sec-butoxy group, an isopentyloxy group, a neopentyloxy group, a tert-pentyloxy group, a 1,2-dimethylpropoxy group, etc.

The term "aryl group" means an aromatic carbocyclic group, which is monocyclic to tetracyclic, and that is composed of 6 to 18 carbon atoms, and examples include a phenyl group, a naphthyl group, an anthryl group, a phenanthryl group, a tetracenyl group, a pyrenyl group, etc.

The term "heteroaryl group" means a monocyclic or fused cyclic aromatic heterocyclic group and examples include a pyridyl group, a pyridazinyl group, a pyrimidinyl group, a pyrazinyl group, a thienyl group, a pyrrolyl group, a thiazolyl group, an isothiazolyl group, a pyrazolyl group, an imidazolyl group, a furyl group, an oxazolyl group, an isoxazolyl group, an oxadiazolyl group, a 1,3,4-thiadiazolyl group, a 1,2,3-triazolyl group, a 1,2,4-triazolyl group, a tetrazolyl group, a quinolyl group, an isoquinolyl group, a naphthyridinyl group, a quinazolinyl group, a benzofuranyl group, a benzothienyl group, an indolyl group, a benzoxazolyl group, a benzoisoxazolyl group, a 1H-indazolyl group, a 2H-indazolyl group, a benzimidazolyl group, a benzoxadiazolyl group, a benzothiadiazolyl group, an indolizinyl group, a benzofurazanyl group, a thienopyridyl group, a pyrazolopyridyl group, an imidazopyridyl group, an imidazopyrazinyl group, a pyrazolopyrimidinyl group, a triazolopyrimidinyl group, a thienothienyl group, an imidazothiazolyl group, etc.

The term "mono-$C_{1-6}$ alkylamino group" means an amino group substituted by a single $C_{1-6}$ alkyl group as defined above and examples include a methylamino group, an ethylamino group, a propylamino group, a butylamino group, a pentylamino group, a hexylamino group, an isopropylamino group, an isobutylamino group, a tert-butylamino group, a sec-butylamino group, an isopentylamino group, a neopentylamino group, a tert-pentylamino group, a 1,2-dimethylpropylamino group, etc.

The term "di-$C_{1-6}$ alkylamino group" means an amino group substituted by two respectively independent $C_{1-6}$ alkyl groups as defined above and examples include a dimethylamino group, a diethylamino group, a dipropylamino group, a dibutylamino group, a dipentylamino group, a dihexylamino group, a diisopropylamino group, a diisobutylamino group, a di-tert-butylamino group, a di-sec-butylamino group, a di-isopentylamino group, a di-neopentylamino group, a di-tert-pentylamino group, a di-1,2-dimethylpropylamino group, an ethylmethylamino group, an isopropylmethylamino group, an isobutylisopropylamino group, etc.

The term "$C_{1-6}$ alkylsulfonyloxy group" means a sulfonyloxy group substituted by the $C_{1-6}$ alkyl group defined above and examples include a methylsulfonyloxy group, an ethanesulfonyloxy group, a n-propylsulfonyloxy group, an isopropylsulfonyloxy group, a n-butylsulfonyloxy group, a 2-methyl-n-butylsulfonyloxy group, a tert-butylsulfonyloxy group, a n-pentylsulfonyloxy group, a n-hexylsulfonyloxy group, etc.

In the compounds of the present invention,
X is preferably a bond, —CH$_2$O—, —CH$_2$—, —(CH$_2$)$_2$—, —(CH$_2$)$_3$—, —O—, —CH$_2$—NHC(=O)—, —CH$_2$—NHC(=O)—CH$_2$—, or —CH$_2$—NHS(=O)$_2$—; and
X is more preferably —CH$_2$O—;
in addition, preferably,
R$_1$ is formula (2); and
ring A is either one of the rings represented by the following formula (5)

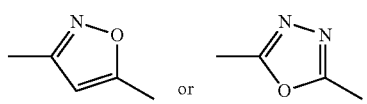

(5)

and R$_2$ is a phenyl group or a pyridyl group (said phenyl group or pyridyl group may be substituted by 1-3 methoxy groups.)

The term "alopecia" means a condition in which some or all hairs have shedded or disappeared or have changed to thinner and shorter hairs. Alopecia manifests itself in various types which include, but are not particularly limited to, male pattern alopecia, seborrheic alopecia, alopecia senilis, alopecia areata, alopecia medicamentosa due, for example, to the administration of cancer control drugs, scarring alopecia, and postpartum alopecia which manifests itself after delivery. Alopecia often results from a disrupted hair cycle and is triggered by a shortened anagen phase due, for example, to the arrest of cell proliferation.

The term "hair cycle" refers to the growth cycle of hairs and represents a period consisting of three stages, (1) the anagen phase (the period during which the hair follicle repeats division to cause active growth of the hair; the anagen phase lasts from two to six years for the hairs on the scalp); (2) the catagen phase (the period during which the hair growth is lessened and the follicle shrinks; the catagen phase lasts from one to two weeks for scalp hair); and (3) the telogen phase (the period during which the follicle is completely degenerated and remains dormant; the telogen phase lasts from three to four months for scalp hair.) Usually, 80 to 90 percent of the hairs are in the anagen phase and less than one percent are in the catagen phase, with the remainder in the telogen phase. Alopecia involves abnormalities in the hair cycle and, particularly in male pattern alopecia, the duration of the anagen phase is shortened and the hair makes a transition to the catagen/telogen phase before it grows to a thicker terminal hair, so the percentage of hairs in the telogen phase increases and the terminal hair changes to a fine vellus.

The term "agents for preventing or treating alopecia" according to the present invention refers to drugs that have either one of the following actions: (1) inducing a transition from the telogen phase to the anagen phase (i.e., inducing hair development); (2) stimulating hair growth; (3) extending the anagen phase; and (4) inhibiting, delaying or reducing the shedding of hairs; drugs having more than one action are desired.

The term "pharmaceutically acceptable salts" means salts that are acceptable from a pharmaceutical viewpoint. Examples include: salts with acids such as acetic acid, propionic acid, butyric acid, formic acid, trifluoroacetic acid, maleic acid, tartaric acid, citric acid, stearic acid, succinic acid, ethylsuccinic acid, malonic acid, lactobionic acid, gluconic acid, glucoheptonic acid, benzoic acid, methansulfonic acid, ethanesulfonic acid, 2-hydroxyethanesulfonic acid, benzenesulfonic acid, p-toluenesulfonic acid (tosylic acid), laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer; salts with inorganic bases such as lithium salts, sodium salts, potassium salts, and calcium salts; and salts with organic amines (e.g., morpholine and piperidine) and amino acids.

The compounds of the present invention and pharmaceutically acceptable salts thereof can occur in various solvated forms. They may also be converted to hydrates from the viewpoint of applicability as pharmaceuticals.

The compounds (1) of the present invention or pharmaceutically acceptable salts thereof may be used as they are or, alternatively, they may be formulated into preparations together with pharmaceutically acceptable carriers by per se known techniques. Pharmaceutically acceptable carriers are various organic or inorganic materials commonly used as pharmaceutical necessities depending on whether they are used in solid preparations or liquid preparations: examples for use in the former case include excipients (e.g., lactose, saccharose, D-mannitol, starch, corn starch, crystalline cellulose, light silicic anhydride, etc.), lubricants (e.g., magnesium stearate, calcium stearate, talc, colloidal silica, etc.), binders (e.g., crystalline cellulose, saccharose, D-mannitol, dextrin, hydroxypropyl cellulose, hydroxypropyl methylcellulose, polyvinylpyrrolidone, starch, sucrose, gelatin, methylcellulose, carboxymethylcellulose sodium, etc.), disintegrants (e.g., starch, carboxymethylcellulose, carboxymethylcellulose calcium, croscarmelose sodium, carboxymethyl starch sodium, low-substitution hydroxypropyl cellulose, etc.); examples for use in liquid preparations include solvents (e.g., water for injections, alcohols, propylene glycol, macrogol, sesame oil, corn oil, etc.), solvent promoters (e.g., polyethylene glycols, propylene glycol, D-mannitol, benzyl benzoate, ethanol, Tris-aminomethane, cholesterol, triethanolamine, sodium carbonate, sodium citrate, etc.), suspending agents (e.g., surfactants such as stearyl triethanolamine, sodium lauryl sulfate, lauryl aminopropionic acid, lecithin, benzalkonium chloride, benzethonium chloride, glyceryl monostearate, etc. or hydrophilic polymers such as polyvinyl alcohol, polyvinylpyrrolidone, carboxymethylcellulose sodium, methylcellulose, hydroxymethyl cellulose, hydroxypropyl cellulose, etc.), isotonic agents (e.g., glucose, D-sorbitol, sodium chloride, glycerin, D-mannitol, etc.), buffering agents (e.g., phosphates, acetates, carbonates, citrates, etc.), and soothing agents (e.g., benzyl alcohol, etc.) In the course of pharmaceutical formulation procedure, various additives may be used depending on the need, as exemplified by preservatives (e.g., paraoxybenzoate esters, chlorobutanol, benzyl alcohol, phenethyl alcohol, dehydroacetic acid, sorbic acid, etc.), antioxidants (e.g., sulfites, ascorbic acid, etc.), coloring agents, sweetening agents, adsorbents, wetting agents, etc.

The compounds of the present invention or pharmaceutically acceptable salts thereof may be administered orally or non-orally (e.g., intravenously, topically, rectally, etc.) Dosage forms of their administration may be exemplified by tablets (including sugar-coated tablets and film-coated tablets), powders, granules, dusts, troches, capsules (including soft capsules), liquids, injections (e.g., subcutaneous, intravenous, intramuscular, intraperitoneal, etc.), external preparations (e.g., for nasal administration, transdermal application, ointments, creams, etc.), suppositories (e.g., rectal, vaginal, etc.), slow-release preparations (e.g., slow-release microcapsules, etc.), pellets, drops, etc.; each of these dosage forms may be manufactured by common pharmaceutical formulation techniques (e.g., the methods described in the 15$^{th}$ Japanese Pharmacopoeia.) External preparations are a preferred dosage form due, for example, to the capability of being directly administered to the affected area, ease of administration, and a lower risk of causing systemic side effects. The compounds can also be used as oral preparations since they exert no immunosuppressing action and the risk for systemic side effects is low.

The thus produced agents of the present invention for preventing or treating alopecia are administered in doses that can be appropriately adjusted depending on such factors as the weight, age, and sex of the patient. Specifically, if the agents are used as an external preparation, the compounds of the present invention are incorporated at concentrations of 0.0001% to 20% and the resulting preparation can be administered once to several times a day. Upon administration, the external preparation is applied to hairs in amounts ranging from about 0.00001 to about 4 mg/cm$^2$, preferably from about 0.01 to about 1 mg/cm$^2$.

If the agents are to be used as an oral preparation, they may be administered once to several times a day, with the compounds of the present invention being contained in daily amounts of 1 to 1000 mg/kg per adult.

Moreover, the compounds of the present invention can be used in combination with other active ingredients for agents that are effective in preventing or treating alopecia. Drugs that can be combined include but are not limited to minoxidil and finasteride. The compounds can also be combined with such drugs as other hair growth stimulants/hair restorers, vasodilators, anti-androgens, cyclosporine derivatives, anti-microbials, anti-inflammatories, thyroid hormone derivatives, prostaglandin agents or antagonists, retinoids, and triterpenes. The compounds and the other active ingredients for agents that are effective in preventing or treating alopecia may be used as separate preparations or, alternatively, they may be used as a single combined drug.

While the method for producing the compounds of the present invention is described below, it is by no means limited to the following examples. Starting compounds used to produce the compounds can be readily prepared by known methods or per se known methods. Production methods A to E are described below, with focus being placed on the construction of ring A. As for the addition of the organic residue —R$_1$, the following description assumes a method of introducing the same at the last stage but it may be introduced before constructing ring A or at an intermediate stage. Addition or transformation of the organic residue —X—R$_2$ may also be carried out at any suitable stage. Any reactive functional group that occurs in respective steps may be protected and deprotected as appropriate.

Production Method A

Among the compounds represented by the general formula (1), those in which ring A is represented by the following formula:

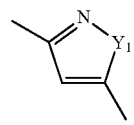

(Y$_1$ represents an oxygen atom, NMe, or NH) may be produced by, for example, the following method.

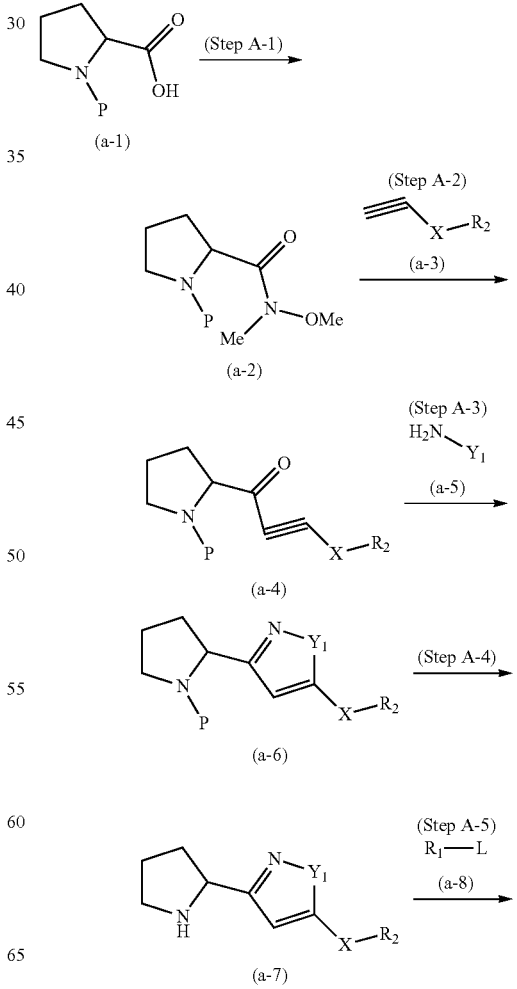

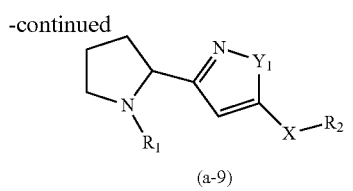

(a-9)

(where $R_1$, $R_2$ and X have the same meanings as defined above; P represents an amino protecting group (e.g., a t-butoxycarbonyl group, a benzyloxycarbonyl group, etc.); $Y_1$ represents an oxygen atom, NMe or NH; and L represents a hydroxy group or a leaving group (e.g., chlorine, bromine, iodine, etc.))

(1) Step A-1

To obtain a compound represented by formula (a-2), a compound represented by formula (a-1) is reacted with methoxymethylamine through commonly practiced acylation. For example, the carboxylic acid compound represented by formula (a-1) is reacted with thionyl chloride, oxalyl chloride, etc. so that it is converted to the corresponding acid halide or, alternatively, the compound of formula (a-1) is reacted with ethyl chloroformate, isobutyl chloroformate, etc. so that it is converted to the corresponding mixed acid anhydride; the resulting product is then reacted with methoxymethylamine either in a solvent or with no solvent used, optionally in the presence of a base. The compound represented by formula (a-2) can also be obtained by reacting the compound (a-1) with methoxymethylamine using a condensing agent such as dicyclohexylcarbodiimide or 1-ethyl-3-(3-dimethylaminopropyl)carbodiimide. The solvent may be a halogen-based solvent such as methylene chloride or chloroform, an ether-based solvent such as tetrahydrofuran or dioxane, an aromatic hydrocarbon-based solvent such as toluene or xylene, an aprotic polar solvent such as N,N-dimethylformamide, or mixtures of these solvents. The base may be an organic base such as pyridine or triethylamine, or an inorganic base such as sodium hydroxide or sodium hydrogencarbonate.

(2) Step A-2

To obtain a compound represented by formula (a-4), a compound represented by formula (a-3) may be reacted with an organometallic reagent such as MeLi, n-BuLi or EtMgBr in a solvent to generate an acetylide, which is then reacted with the compound of formula (a-2). The solvent may be an ether-based solvent such as tetrahydrofuran or dioxane, an aliphatic hydrocarbon solvent such as hexane or pentane, or mixtures of these solvents.

(3) Step A-3

To obtain a compound represented by formula (a-6), the compound of formula (a-4) is reacted with a compound represented by formula (a-5) or a salt thereof either in a solvent or with no solvent used, optionally in the presence of an acid or a base. The solvent may be an alcohol such as methanol or ethanol, an ether-based solvent such as tetrahydrofuran or dioxane, an aprotic polar solvent such as N,N-dimethylormamide, water, or mixtures of these solvents. The acid may be an inorganic acid such as hydrochloric acid or sulfuric acid, or an organic acid such as acetic acid or p-toluenesulfonic acid. The base may be an organic base such as pyridine or triethylamine, or an inorganic base such as AcONa, NaOMe, $Na_2SO_4$, or $K_2CO_3$.

(4) Step A-4

To obtain a compound represented by formula (a-7), the amino protecting group in the compound of formula (a-6) is removed for deprotection. If the protecting group is a t-butoxycarbonyl group, deprotection may be effected by carrying out reaction with an acid such as trifluoroacetic acid or hydrochloric acid; if the protecting group is a benzyloxycarbonyl group, deprotection may be effected either by hydrogenation in the presence of a catalyst such as palladium-carbon or platinum oxide or by reaction with an acid such as HBr-AcOH. If other protecting groups are to be removed, methods commonly practiced to remove the amino protecting group of interest may be implemented.

(5) Step A-5

To obtain a compound represented by formula (a-9), a compound represented by formula (a-8) (where L is an OH group) is treated by the same method as described in Step A-1 so that it is converted to an acid halide and then reacted with the compound of formula (a-7), or it may be directly reacted with the compound of formula (a-7) in the presence of a condensing agent. Alternatively, a compound represented by formula (a-9) may be obtained by reacting a compound of formula (a-8) (where L is a leaving group) with the compound of formula (a-7) in a solvent, optionally in the presence of a base.

Production Method B

Among the compounds represented by the general formula (1), those in which ring A is represented by the following formula:

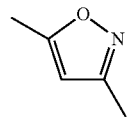

may be produced by, for example, the following method.

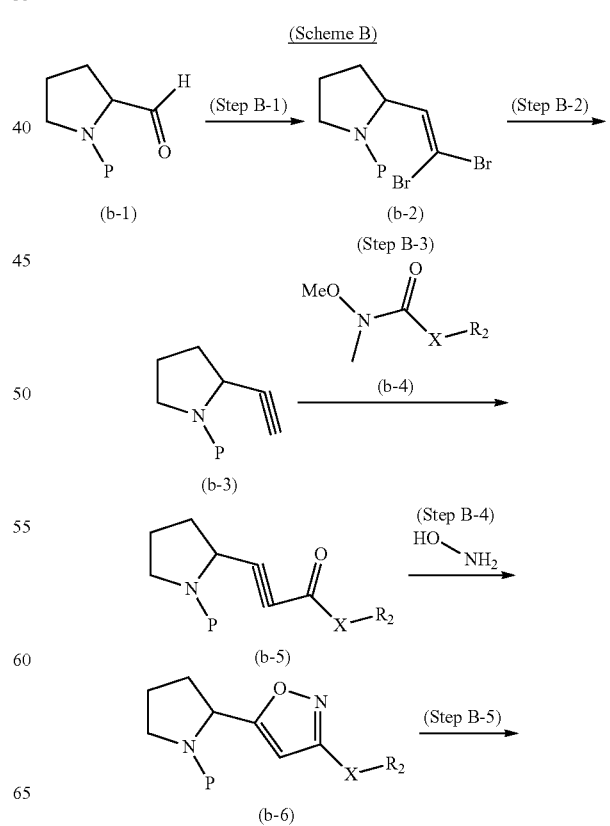

13

-continued

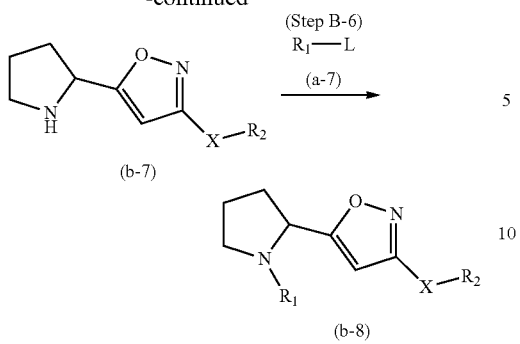

(Step B-6)
R₁—L
(a-7)

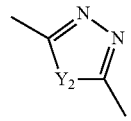

(where R₁, R₂ and X have the same meanings as defined above; P represents an amino protecting group (e.g., a t-butoxycarbonyl group, a benzyloxycarbonyl group, etc.); L represents a hydroxy group or a leaving group (e.g., chlorine, bromine, iodine, etc.))

(1) Step B-1

To obtain a compound represented by formula (b-2), a compound represented by formula (b-1) is reacted with CBr₄ and PPh₃ in a halogen-based solvent such as methylene chloride or chloroform by the method described in Journal of Medicinal Chemistry, 1990, vol. 33, page 3190 or a modified version of the method.

(2) Step B-2

To obtain a compound represented by formula (b-3), the compound of formula (b-2) is reacted with a base in a solvent. The base may be MeLi, n-BuLi, sec-BuLi, LiN(i-Pr)₂, or the like. The solvent may be an ether-based solvent such as tetrahydrofuran or dioxane, an aliphatic hydrocarbon solvent such as hexane or pentane, or mixtures of these solvents.

(3) Step B-3

To obtain a compound represented by formula (b-5), the compound (b-3) may be reacted with an organometallic reagent such as MeLi, n-BuLi or EtMgBr in a solvent to generate an acetylide, which is then reacted with a compound represented by (b-4). The solvent may be an ether-based solvent such as tetrahydrofuran or dioxane, an aliphatic hydrocarbon solvent such as hexane or pentane, or mixtures of these solvents. To obtain a compound represented by formula (b-5), an acetylide corresponding to the compound of formula (b-3) generated in situ by the reaction described in Step B-2 may be reacted with the compound of formula (b-4).

(4) Step B-4

To obtain a compound represented by formula (b-6), the compound of formula (b-5) is reacted with hydroxylamine or a salt thereof either in a solvent or with no solvent used, optionally in the presence of an acid or a base. The solvent may be an alcohol such as methanol or ethanol, an ether-based solvent such as tetrahydrofuran or dioxane, an aprotic polar solvent such as N,N-dimethylormamide, water, or mixtures of these solvents. The acid may be an inorganic acid such as hydrochloric acid or sulfuric acid, or an organic acid such as acetic acid or p-toluenesulfonic acid. The base may be an organic base such as pyridine or triethylamine, or an inorganic base such as AcONa, NaOMe, Na₂SO₄, or K₂CO₃.

(5) Step B-5

A compound represented by formula (b-7) is obtained from the compound of formula (b-6) by the same method as described in Step A-4.

(6) Step B-6

A compound represented by formula (b-8) is obtained from the compound of formula (b-7) by the same method as described in Step A-5.

14

Production Method C

Among the compounds represented by the general formula (1), those in which ring A is represented by the following formula:

(where Y₂ represents an oxygen atom or a sulfur atom) may be produced by, for example, the following method.

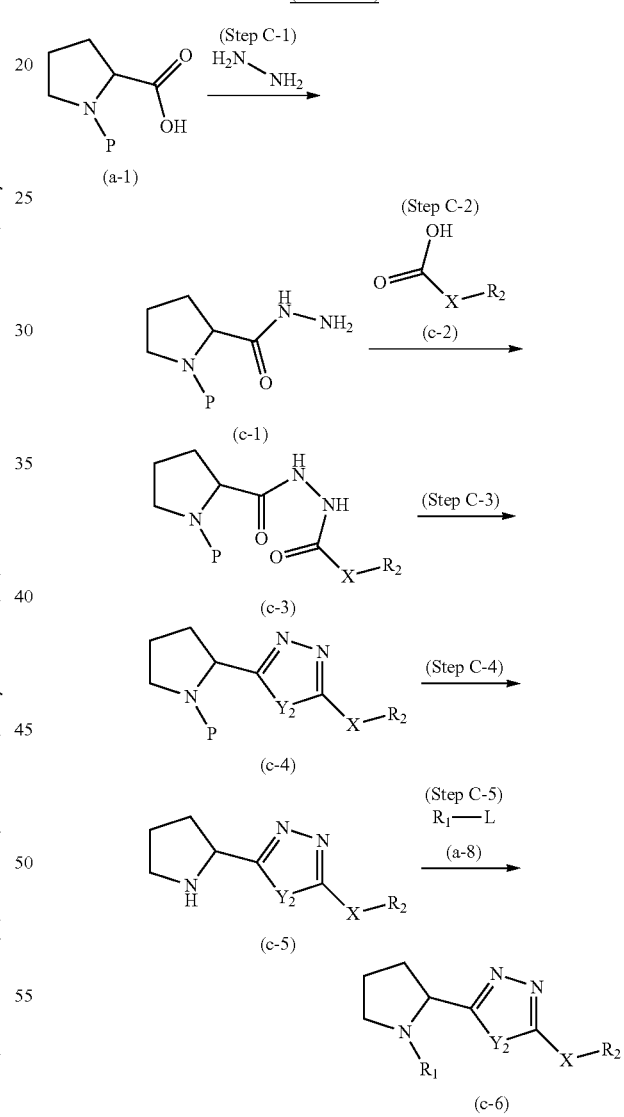

(where R₁, R₂ and X have the same meanings as defined above; P represents an amino protecting group (such as a t-butoxycarbonyl group, a benzyloxycarbonyl group, etc.); Y₂ represents an oxygen atom or a sulfur atom; L represents a hydroxy group or a leaving group (e.g., chlorine, bromine, iodine, etc.))

(1) Step C-1

A compound represented by formula (c-1) is obtained from the compound of formula (a-1) and hydrazine by the commonly practiced acylation which is described in Step A-1.

(2) Step C-2

A compound represented by formula (c-3) is obtained from the compounds of formula (c-1) and (c-2) by the commonly practiced acylation which is described in Step A-1.

(3) Step C-3

Among the compounds represented by formula (c-4), a compound where $Y_2$ is an oxygen atom is obtained by subjecting the compound of formula (c-3) to cyclodehydration in a solvent using Burgess reagent or $CBr_4$, $PPh_3$, imidazole, etc. The solvent may be a halogen-based solvent such as methylene chloride or chloroform, or an aromatic hydrocarbon solvent such as toluene or xylene.

Among the compounds represented by formula (c-4), a compound where $Y_2$ is a sulfur atom is obtained by reacting the compound of formula (c-3) with Lawesson's reagent or the like in a solvent. The solvent may be a halogen-based solvent such as methylene chloride or chloroform, or an aromatic hydrocarbon solvent such as toluene or xylene.

(4) Step C-4

A compound represented by formula (c-5) is obtained from the compound of formula (c-4) by the same method as described in Step A-4.

(5) Step C-5

A compound represented by formula (c-6) is obtained from the compound of formula (c-5) by the same method as described in Step A-5.

Production Method D

Among the compounds represented by the general formula (1), those in which ring A is represented by the following formula:

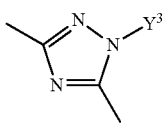

(where $Y_3$ represents a hydrogen atom or a Me group) may be produced by, for example, the following method.

(Scheme D)

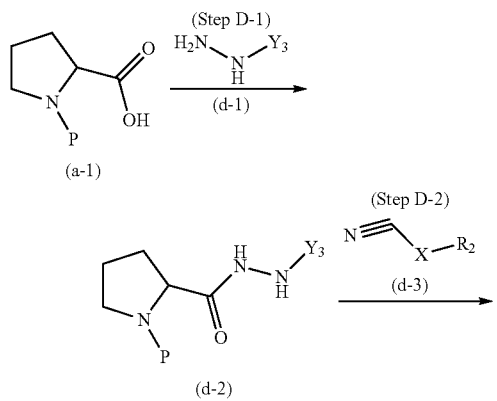

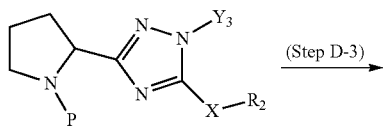

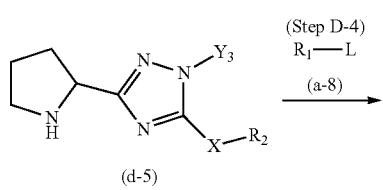

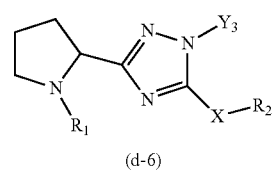

(where $R_1$, $R_2$ and X have the same meanings as defined above; P represents an amino protecting group (such as a t-butoxycarbonyl group, a benzyloxycarbonyl group, etc.); $Y_3$ represents a hydrogen atom or a Me group; L represents a hydroxy group or a leaving group (e.g., chlorine, bromine, iodine, etc.))

(1) Step D-1

A compound represented by formula (d-2) can be obtained from the compound of formula (a-1) by reacting it with a hydrazine compound of formula (d-1) by the commonly practiced acylation which is described in Step A-1; alternatively, the compound of formula (a-1) may be reacted with a protected form of hydrazine corresponding to the hydrazine compound of formula (d-1) and then deprotected.

(2) Step D-2

A compound represented by formula (d-4) is obtained from the compound of formula (d-2) and a cyano compound of formula (d-3) by means of heating in a solvent, optionally in the presence of an acid or a base. The solvent may be an alcohol such as methanol or butanol, or an ether-based solvent such as dioxane or diphenylether. The acid may be an organic acid such as acetic acid. The base may be an inorganic base such as NaOMe or $K_2CO_3$. The reaction may be performed at a temperature ranging from the solvent's reflux temperature to 220° C. under atmospheric or superatmospheric pressure or under microwave irradiation.

(3) Step C-3

A compound represented by formula (d-5) is obtained from the compound of formula (d-4) by the same method as described in Step A-4.

(4) Step C-4

A compound represented by formula (d-6) is obtained from the compound of formula (d-5) by the same method as described in Step A-5.

Production Method E

Among the compounds represented by the general formula (1), those in which ring A is represented by the following formula:

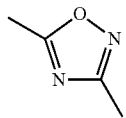

may be produced by, for example, the following method.

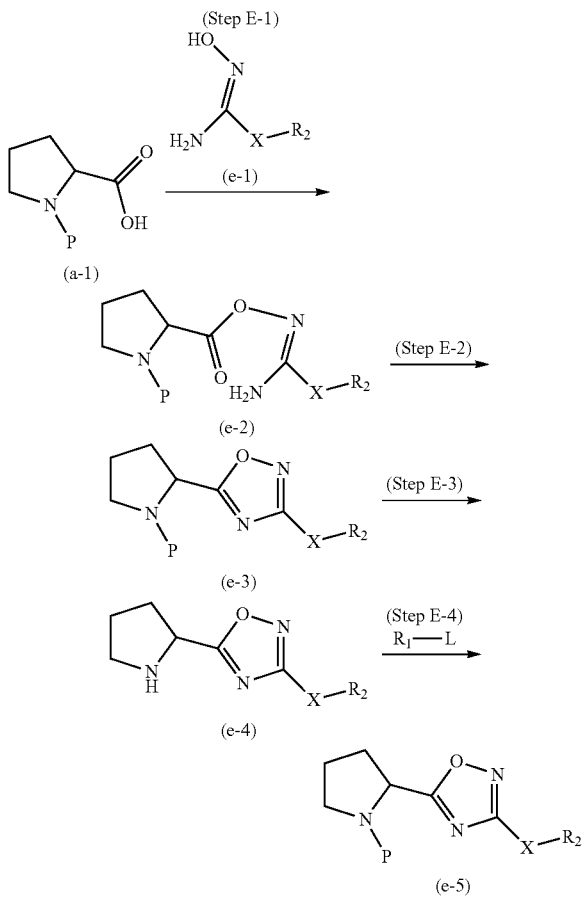

(where R$_1$, R$_2$ and X have the same meanings as defined above; P represents an amino protecting group (such as a t-butoxycarbonyl group, a benzyloxycarbonyl group, etc.); L represents a hydroxy group or a leaving group (e.g., chlorine, bromine, iodine, etc.))

(1) Step E-1

A compound represented by formula (e-2) can be obtained from the compound of formula (a-1) by reacting it with a compound of formula (e-1) by the commonly practiced acylation which is described in Step A-1.

(2) Step E-2

A compound represented by formula (e-3) is obtained by subjecting the compound of formula (e-2) to dehydration in a solvent, optionally in the presence of an acid or a base. The solvent may be an ether-based solvent such as dioxane or an aromatic hydrocarbon solvent such as toluene or xylene. The acid may be an organic acid such as p-toluenesulfonic acid. The base may be an organic base such as pyridine or triethylamine or an ammonium salt such as n-Bu$_4$NF. The reaction may be performed at a temperature ranging from room temperature to the solvent's reflux temperature.

(3) Step E-3

A compound represented by formula (e-4) is obtained from the compound of formula (e-3) by the same method as described in Step A-4.

(4) Step E-4

A compound represented by formula (e-5) is obtained from the compound of formula (e-4) by the same method as described in Step A-5.

Production Method F

Among the compounds represented by the general formula (1), those in which ring A is represented by the following formula:

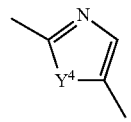

(where Y$_4$ represents an oxygen atom or a sulfur atom) may be produced by, for example, the following method.

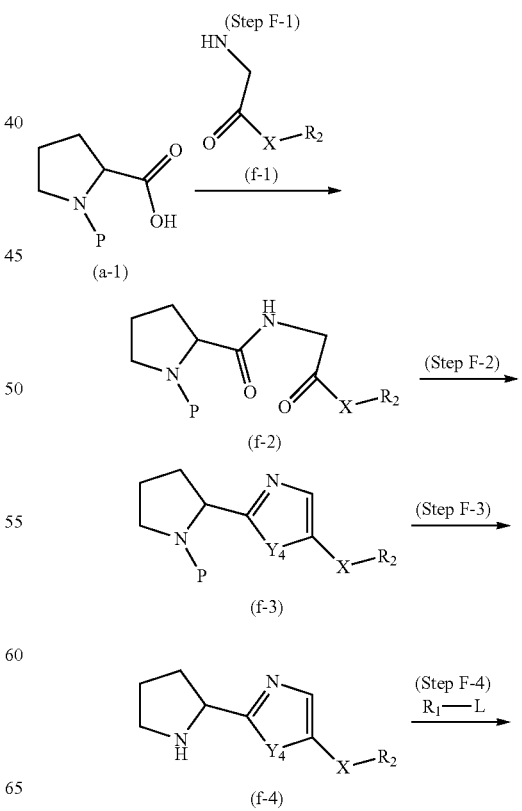

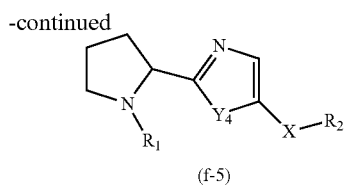

(f-5)

(where $R_1$, $R_2$ and X have the same meanings as defined above; P represents an amino protecting group (such as a t-butoxycarbonyl group, a benzyloxycarbonyl group, etc.); $Y_4$ represents an oxygen atom or a sulfur atom; L represents a hydroxy group or a leaving group (e.g., chlorine, bromine, iodine, etc.))

(1) Step F-1

A compound represented by formula (f-2) can be obtained from the compound of formula (a-1) by reacting it with a compound of formula (f-1) by the commonly practiced acylation which is described in Step A-1.

(2) Step F-2

Among the compounds represented by formula (f-3), a compound where $Y_4$ is an oxygen atom is obtained by subjecting the compound of formula (f-2) to cyclodehydration in a solvent using Burgess reagent or $CBr_4$, $PPh_3$, imidazole, etc. The solvent may be a halogen-based solvent such as methylene chloride or chloroform, or an aromatic hydrocarbon solvent such as toluene or xylene.

Among the compounds represented by formula (f-3), a compound where $Y_4$ is a sulfur atom is obtained by reacting the compound of formula (f-2) with Lawesson's reagent or the like in a solvent. The solvent may be a halogen-based solvent such as methylene chloride or chloroform, or an aromatic hydrocarbon solvent such as toluene or xylene.

(3) Step F-3

A compound represented by formula (f-4) is obtained from the compound of formula (f-3) by the same method as described in Step A-4.

(4) Step F-4

A compound represented by formula (f-5) is obtained from the compound of formula (f-4) by the same method as described in Step A-5.

EXAMPLES

On the following pages, the present invention is described in greater detail by means of working examples and test examples. It should be noted that the compounds of the present invention are by no means limited to those described in the following working examples.

Unless otherwise noted:

M. S. GEL D-75-60-A (product of DOKAI CHEMICAL INDUSTRY, LTD.) was used as a carrier in silica gel chromatography;

Chromatorex NH-DM1020 (product of FUJI SILYSIA CHEMICAL LTD.) was used as a carrier in NH-form silica gel chromatography;

Silica Gel 60N (product of Kanto Chemical Co., Inc.) or KP-Sil 20 µm silica gel (product of Biotage) was used as a carrier in neutral silica gel chromatography.

The NMR spectra were those of proton NMR; tetramethylsilane was used as an internal reference, with δ values being indicated in ppm.

MS measurements were performed using LC/MS-2010EV (equipped with dual ESI/APCI source).

Reverse-phae preparative HPLC was performed using GILSON preparative HPLC system. The following column and solvents were used for preparative purposes.

Column: Waters, SunFire Prep C18, OBD 5.0 µm, 30×50 mm Column

Solvents: $CH_3CN$ (0.1% $CF_3COOH$), $H_2O$ (0.1% $CF_3COOH$)

The abbreviations used in the working examples have following meanings.

AcOEt: ethyl acetate

APCI: atmospheric pressure chemical ionization

Boc: t-butoxycarbonyl

Brine: saturated aqueous sodium chloride

DBU: diazabicycloundecene

DPPA: diphenylphosphoryl azide $Et_3N$: triethylamine $Et_2O$: diethylether

ESI: electrospray ionization

HOBt: 1-hydroxybenzotriazole

MsCl: methanesulfonyl chloride

NMP: N-methyl-pyrrolidone

Pd—C: palladium on carbon $PPh_3$: triphenylphosphine

PTLC: preparative thin-layer chromatography

THF: tetrahydrofuran

WSC: 1-ethyl-3-(3-dimethylaminopropyl)carbodiimide hydrochloride

Burgess reagent: methyl N-(triethylammoniumsulfonyl)carbamate

Lawesson's reagent: 2,4-bis(4-methoxyphenyl)-1,3,2,4-dithiadiphosphetane-2,4-disulfide s: singlet br.s.: broad singlet d: doublet dd: double doublet m: multiplet Example 1

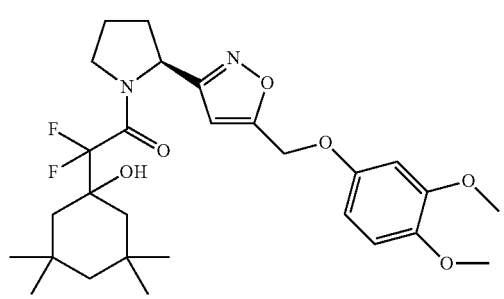

(S)-1-(2-(5-((3,4-Dimethoxyphenoxy)methyl)isoxazol-3-yl)pyrrolidin-1-yl)-2,2-difluoro-2-(1-hydroxy-3,3,5,5-tetramethylcyclohexyl)ethanone (Compound 1)

Example 1-(1)

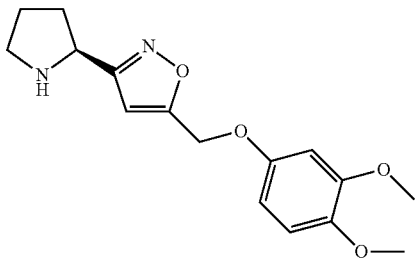 [SMILES: COc1ccc(OCc2cc([C@@H]3CCCN3)no2)cc1OC]

(S)-5-((3,4-Dimethoxyphenoxy)methyl)-3-(pyrrolidin-2-yl)isoxazole

In an argon atmosphere, n-BuLi (147 mL as 2.76 N hexane solution) was added to a solution of 1,2-dimethoxy-4-(prop-2-yn-1-yloxy)benzene (81.85 g) in THF (1000 mL) at −60° C. to −70° C. over 55 minutes and after stirring at the same temperature for 30 minutes, a solution of (S)-t-butyl 2-(methoxy(methyl)carbamoyl)pyrrolidine-1-carboxylate (100.00 g) in THF (600 mL) was added dropwise and temperature was raised to room temperature over 2 hours, followed by stirring at 25° C. for 30 minutes. The reaction mixture was added to a saturated aqueous solution of $NH_4Cl$ (3 L), ice water (2 L), hexane (1 L) and AcOEt (1 L); the organic layer was separated, washed with brine (5 L), water (2 L), and brine (1 L) successively, dried ($MgSO_4$), filtered and concentrated to give a brown oil (161.24 g), which was dissolved in EtOH (1000 mL); to the solution, hydroxylamine hydrochloride (53.79 g) was added and after heating under reflux for 13 hours, the mixture was stirred at room temperature for 13 hours. After reheating under reflux for 6 hours, the reaction mixture was concentrated to give a brown oil, to which HCl (1000 mL as 4.0 N AcOEt solution) was added and the mixture was stirred at room temperature for 64 hours. To the reaction mixture, water (2 L) was added and after separating the organic layer, NaOH (230 g) was added to the aqueous layer under cooling with ice; after extraction with $CHCl_3$ (2 L), the organic layer was dried ($Na_2SO_4$), filtered and concentrated to give a crude product, which was further purified by neutral silica gel chromatography (MeOH/$CHCl_3$) to give the titled compound (49.98 g, brown oil.)

$^1$H NMR (200 MHz, CHLOROFORM-d) δ 6.78 (d, J=8.8 Hz, 1H), 6.57 (d, J=3.1 Hz, 1H), 6.45 (dd, J=3.1, 8.8 Hz, 1H), 6.31 (s, 1H), 5.07 (s, 2H), 4.38-4.24 (m, 1H), 3.85 (s, 3H), 3.84 (s, 3H), 3.22-2.92 (m, 2H), 2.33-1.72 (m, 4H)

Example 1-(2)

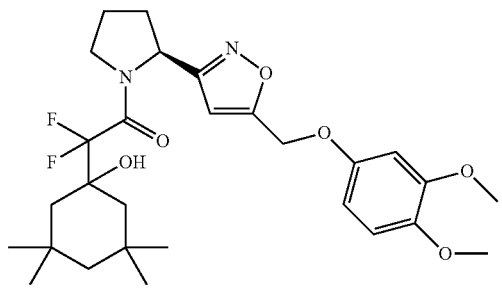

(S)-1-(2-(5-((3,4-Dimethoxyphenoxy)methyl)isoxazol-3-yl)pyrrolidin-1-yl)-2,2-difluoro-2-(1-hydroxy-3,3,5,5-tetramethylcyclohexyl)ethanone (Compound 1)

To a solution of 2,2-difluoro-2-(1-hydroxy-3,3,5,5-tetramethylcyclohexyl)acetate (87.83 g) and $Et_3N$ (122 mL) in THF (2000 mL), ethyl chloroformate (30.8 mL) was added at room temperature and the mixture was stirred for 30 minutes. To the reaction mixture, a THF (500 mL) solution of the compound (89.00 g) obtained in Example 1-(1) was added dropwise at room temperature over an hour and the mixture was stirred at room temperature for 20 hours. The reaction mixture was concentrated and AcOEt (2 L) and a saturated aqueous solution of $NH_4Cl$ (2 L) were added; after filtering the insoluble matter, the organic layer was separated and washed with saturated aqueous sodium bicarbonate (2 L), dried ($MgSO_4$), filtered and concentrated to give a crude product (165.0 g). A similar method was applied using 2,2-difluoro-2-(1-hydroxy-3,3,5,5-tetramethylcyclohexyl)acetate (34.64 g) and (S)-5-((3,4-dimethoxyphenoxy)methyl)-3-(pyrrolidin-2-yl)isoxazole (35.10 g) to give a crude product (60.10 g), which was combined with the first crude product and further purified by silica gel chromatography (AcOEt/hexane) and NH-form silica gel chromatography (AcOEt/hexane); the purified product was recrystallized ($Et_2O$/pentane) to give the titled compound (134.30 g, colorless powder.)

$^1$H NMR (600 MHz, CHLOROFORM-d) δ 6.78 (d, J=8.7 Hz, 1H), 6.57 (d, J=2.8 Hz, 1H), 6.44 (dd, J=2.8, 8.7 Hz, 1H), 6.26 [6.18] (s, 1H), 5.43-5.39 [5.60-5.55] (m, 1H), 5.11-5.00 (m, 2H), 4.23-4.13 (m, 1H), 3.99-3.71 (m, 2H), 3.86 (s, 3H), 3.84 (s, 3H), 2.34-0.78 (m, 22H)

m.p. 99.0-101.0° C.

Example 2

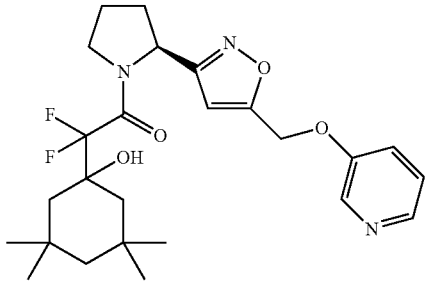 [SMILES: CC1(C)CC(C)(C)CC(O)(C(F)(F)C(=O)N2CCC[C@H]2c2cc(COc3cccnc3)on2)C1]

(S)-2,2-Difluoro-2-(1-hydroxy-3,3,5,5-tetramethylcyclohexyl)-1-(2-(5-((pyridin-3-yloxy)methyl)isoxazol-3-yl)pyrrolidin-1-yl)ethanone (Compound 40)

Example 2-(1)

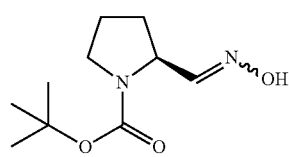

(S)-t-Butyl 2-((hydroxyimino)methyl)pyrrolidine-1-carboxylate

To a solution of (S)-t-butyl-2-formylpyrrolidine-1-carboxylate (40.94 g) in pyridine (411 mL), hydroxylamine monohydrochloride (28.56 g) was added at 0° C. and the mixture was stirred at room temperature for 17 hours. The reaction mixture was added to a mixture of AcOE (1.5 L) and hydrochloric acid (2 L, 3.0 N). The organic layer was separated, washed with saturated aqueous sodium bicarbonate (1 L), dried (MgSO$_4$), filtered and concentrated to give the titled compound (39.78 g, colorless solid.)
ESI+237 (M+Na)$^+$ Example 2-(2)

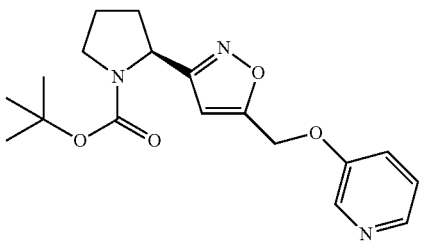 [SMILES: CC(C)(C)OC(=O)N1CCC[C@H]1c1cc(COc2cccnc2)on1]

(S)-tert-Butyl 2-(5-((pyridin-3-yloxy)methyl)isoxazol-3-yl)pyrrolidine-1-carboxylate To a DMF (60 mL) solution of the compound (8.57 g) obtained in Example 2-(1), NCS (5.341 g) was added in small portions at 0° C. and the mixture was stirred at room temperature for an hour. The reaction mixture was cooled to 0° C. and after adding a solution of 3-(prop-2-yn-1-yloxy)pyridine (2.663 g) in THF (5 mL) and a solution of Et$_3$N (5.6 mL) in THF (15 mL), the resulting mixture was stirred at room temperature for 14 hours. The reaction mixture was added to saturated aqueous sodium bicarbonate (200 mL), followed by extraction with AcOEt (200 mL). The resulting organic layer was washed with brine (200 mL), dried (MgSO$_4$), filtered and concentrated to give a crude product, which was further purified by neutral silica gel chromatography (AcOEt/hexane) to give the titled compound (3.81 g, pale yellow solid.)
$^1$H NMR (200 MHz, CHLOROFORM-d) δ 8.42-8.26 (m, 2H), 7.30-7.20 (m, 2H), 6.39-6.19 (m, 1H), 5.18 (br s, 2H), 5.10-4.86 (m, 1H), 3.65-3.35 (m, 2H), 2.44-1.83 (m, 4H), 1.59-1.14 (m, 9H)

Example 2-(3)

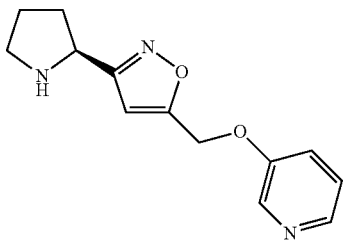 [SMILES: c1cncc(OCc2cc([C@@H]3CCCN3)no2)c1]

(S)-5-((Pyridin-3-yloxy)methyl)-3-(pyrrolidin-2-yl)isoxazole

To an AcOEt (20 mL) solution of the compound (3.81 g) obtained in Example 2-2, HCl (40 mL, 4.0 N AcOEt solution) was added and the mixture was stirred at room temperature for 40 hours. After concentrating the reaction mixture, saturated aqueous sodium bicarbonate (200 mL) and sodium chloride were added, followed by extraction with CHCl$_3$ (200 mL×2). The resulting organic layer was dried (Na$_2$SO$_4$), filtered and concentrated to give the titled compound (2.614 g, brown oil.)
$^1$H NMR (200 MHz, CHLOROFORM-d) δ 8.42-8.35 (m, 1H), 8.32-8.25 (m, 1H), 7.32-7.19 (m, 2H), 6.35 (s, 1H), 5.17 (s, 2H), 4.39-4.26 (m, 1H), 3.20-2.93 (m, 2H), 2.30-1.70 (m, 4H)

Example 2-(4)

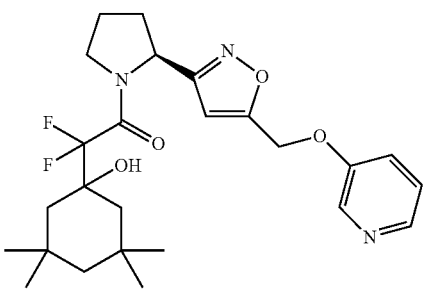 [SMILES: CC1(C)CC(C)(C)CC(O)(C(F)(F)C(=O)N2CCC[C@H]2c2cc(COc3cccnc3)on2)C1]

(S)-2,2-Difluoro-2-(1-hydroxy-3,3,5,5-tetramethylcyclohexyl)-1-(2-(5-((pyridin-3-yloxy)methyl)isoxazol-3-yl)pyrrolidin-1-yl)ethanone (Compound 40)

To a solution of 2,2-difluoro-2-(1-hydroxy-3,3,5,5-tetramethylcyclohexyl)acetic acid (3.192 g) and Et$_3$N (4.44 mL) in THF (100 mL), ethyl chloroformate (1.12 mL) was added at room temperature and the mixture was stirred for an hour. To the reaction mixture, a THF (50 mL) solution of the compound (2.607 g) obtained in Example 2-(3) was added dropwise at room temperature and the mixture was stirred at room temperature for 64 hours. To the reaction mixture, saturated aqueous sodium bicarbonate (200 mL) was added and the organic layer extracted with AcOEt (200 mL) was washed with brine (200 mL), dried (MgSO$_4$), filtered and concentrated to give a crude product, which was further purified by NH-form silica gel chromatography (AcOEt/hexane); the resulting compound was recrystallized (Et$_2$O/pentane) to give the titled compound (2.969 g, colorless powder.)
$^1$H NMR (600 MHz, CHLOROFORM-d) δ 8.41-8.34 (m, 1H), 8.32-8.25 (m, 1H), 7.28-7.20 (m, 2H), 6.29 [6.20] (s, 1H), 5.41-5.37 [5.58-5.55] (m, 1H), 5.17-5.12 (m, 2H), 4.20-4.13 (m, 1H), 3.90-3.70 (m, 2H), 2.33-0.82 (m, 22H)
m.p. 102.0-104.0° C.

Example 3

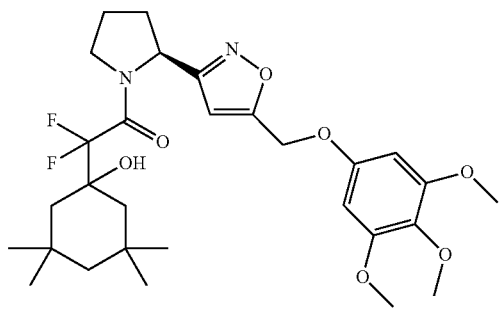

(S)-2,2-Difluoro-2-(1-hydroxy-3,3,5,5-tetramethyl-cyclohexyl)-1-(2-(5-((3,4,5-trimethoxyphenoxy)methyl)isoxaol-3-yl)pyrrolidin-1-yl)ethanone (Compound 21)

Example 3-(1)

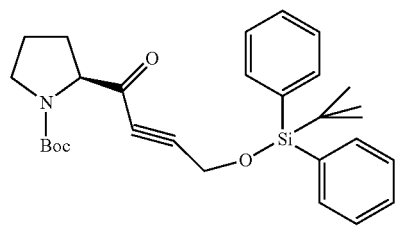 [SMILES: CC(C)(C)OC(=O)N1CCC[C@H]1C(=O)C#CCO[Si](c1ccccc1)(c1ccccc1)C(C)(C)C]

(S)-t-Butyl 2-(4-((tert-butyldiphenylsilyl)oxy)but-2-ynoyl)pyrrolidine-1-carboxylate In an argon atmosphere, n-BuLi (10.3 mL, 2.64 N hexane solution) was added dropwise to a solution of t-butyldiphenyl (prop-2-yn-1-yloxy)silane (8.576 g) in THF (200 mL) at −78° C. over 10 minutes, and after stirring at room temperature for 50 minutes, the reaction mixture was added dropwise to a solution of (S)-t-butyl 2-(methoxy(methyl)carbamoyl)pyrrolidine-1-carboxylate (5.01 g) in THF (200 mL) through a cannula and temperature was raised to room temperature over an hour. The reaction mixture was added to a saturated aqueous solution of $NH_4Cl$ (500 mL) and, after extraction with AcOEt, the organic layer was dried ($MgSO_4$), filtered and concentrated to give a crude product, which was further purified by neutral silica gel chromatography (AcOEt/hexane) to give the titled compound (5.36 g, colorless oil.)

ESI/APCI Dual 514 (M+Na)$^+$

Example 3-(2)

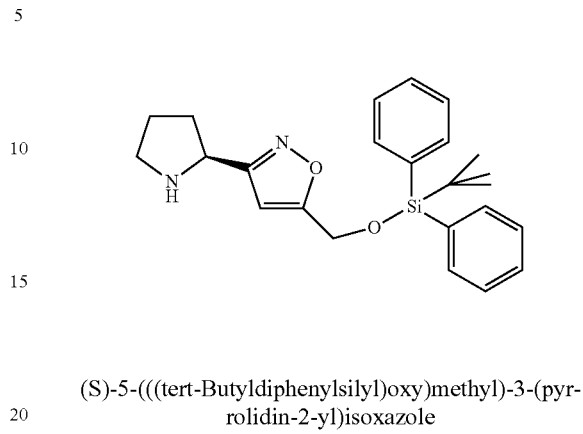

(S)-5-(((tert-Butyldiphenylsilyl)oxy)methyl)-3-(pyrrolidin-2-yl)isoxazole

To an EtOH (10 mL) solution of the compound (492 mg) obtained in Example 3-(1), hydroxylamine hydrochloride (139 mg) was added and the mixture was heated under reflux for 17 hours. To the reaction mixture, saturated aqueous sodium bicarbonate (50 ml) was added and the organic layer extracted with AcOEt was dried ($MgSO_4$), filtered and concentrated to give a crude product, which was further purified by neutral silica gel chromatography (AcOEt→MeOH/$CHCl_3$) to give the titled compound (163 mg, brown oil.)

ESI/APCI Dual 407 (M+H)$^+$

Example 3-(3)

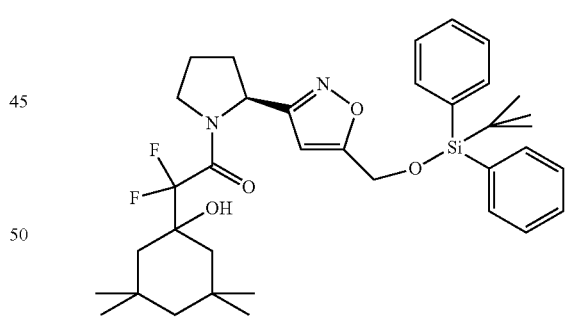

(S)-1-(2-(5-(((tert-Butyldiphenylsilyl)oxy)methyl)isoxazol-3-yl)pyrrolidin-1-yl)-2,2-difluoro-2-(1-hydroxy-3,3,5,5-tetramethylcyclohexyl)ethanone The procedure of Example 1-(2) was repeated, except that the compound obtained in Example 1-(1) was replaced by the compound (150 mg) obtained in Example 3-(2); this gave the titled compound (133 mg, colorless amorphous.)

ESI/APCI Dual 639 (M+H)$^+$

Example 3-(4)

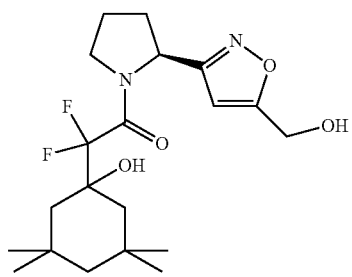 [SMILES: CC1(C)CC(C)(C)CC(O)(C(F)(F)C(=O)N2CCC[C@H]2c2cc(CO)on2)C1]

(S)-2,2-Difluoro-2-(1-hydroxy-3,3,5,5-tetramethyl-cyclohexyl)-1-(2-(5-(hydroxymethyl)isoxazol-3-yl)pyrrolidin-1-yl)ethanone (Compound 18)

To a THF (20 mL) solution of the compound (1.784 g) obtained in Example 3-(3), n-Bu$_4$NF (3.4 mL, 1.0 M THF solution) was added and the mixture was stirred at room temperature for 20 minutes. To the reaction mixture, a saturated aqueous solution of NH$_4$Cl was added and the organic layer extracted with AcOEt was dried (MgSO$_4$), filtered and concentrated to give a crude product, which was further purified with neutral silica gel chromatography (AcOEt/hexane) to give the titled compound (1.010 g, colorless solid.)

ESI/APCI Dual 426 (M+Na)$^+$

Example 3-(5)

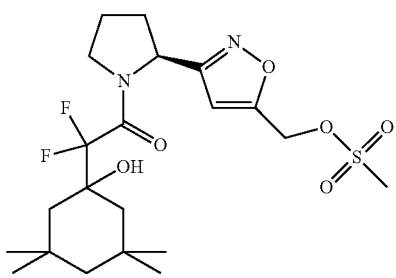 [SMILES: CC1(C)CC(C)(C)CC(O)(C(F)(F)C(=O)N2CCC[C@H]2c2cc(COS(C)(=O)=O)on2)C1]

(S)-(3-(1-(2,2-Difluoro-2-(1-hydroxy-3,3,5,5-tetramethylcyclohexyl)acetyl)pyrrolidin-2-yl)isoxazol-5-yl)methyl methanesulfonate To an AcOEt (3 mL) solution of the compound (45 mg) obtained in Example 3-(4) and Et$_3$N (31 μL), MsCl (13 μL) was added at 0° C. and after stirring the mixture for 30 minutes, MsCl (13 μL) was added and the mixture was stirred at 0° C. for 30 minutes, followed by addition of Et$_3$N (31 μL) and stirring at 0° C. for 2.5 hours. The reaction mixture was added to water (50 mL) and the organic layer extracted with AcOEt (50 mL) was dried (MgSO$_4$), filtered and concentrated to give the titled compound (58 mg, colorless oil.)

ESI/APCI Dual 501 (M+Na)$^+$

Example 3-(6)

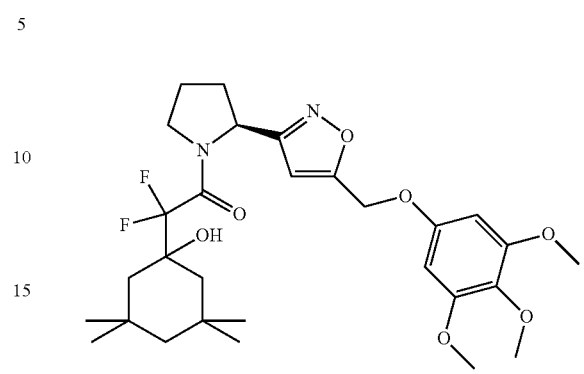

(S)-2,2-Difluoro-2-(1-hydroxy-3,3,5,5-tetramethyl-cyclohexyl)-1-(2-(5-((3,4,5-trimethoxyphenoxy)methyl)isoxazol-3-yl)pyrrolidin-1-yl)ethanone (Compound 21)

To a DMF (1.0 mL) solution of the compound (20.8 mg) obtained in Example 3-(5) and 3,4,5-trimethoxyphenol (16.0 mg), K$_2$CO$_3$ (24.0 mg) was added and the mixture was stirred at room temperature for 30 minutes, then at 50° C. for 2 hours. The reaction mixture was added to water (20 mL) and the organic layer extracted with AcOEt (20 mL×2) was dried (MgSO$_4$), filtered and concentrated to give a crude product, which was further purified by PTLC(NH-form) to give the titled compound (20.5 mg, colorless amorphous.)

1H NMR (600 MHz, CHLOROFORM-d) δ 6.30-6.16 (m, 3H), 5.61-5.35 (m, 1H), 5.14-5.02 (m, 2H), 4.25-4.12 (m, 1H), 3.84 (s, 6H), 3.80 (s, 3H), 3.94-3.68 (m, 2H), 2.36-0.85 (m, 22H)

ESI/APCI Dual 589 (M+Na)$^+$

Example 4

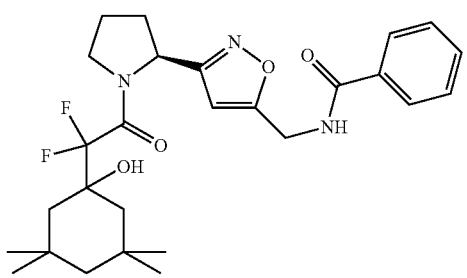 [SMILES: CC1(C)CC(C)(C)CC(O)(C(F)(F)C(=O)N2CCC[C@H]2c2cc(CNC(=O)c3ccccc3)on2)C1]

(S)—N-((3-(1-(2,2-Difluoro-2-(1-hydroxy-3,3,5,5-tetramethylcyclohexyl)acetyl)pyrrolidin-2-yl)isoxazol-5-yl)methyl)benzamide (Compound 44)

Example 4-(1)

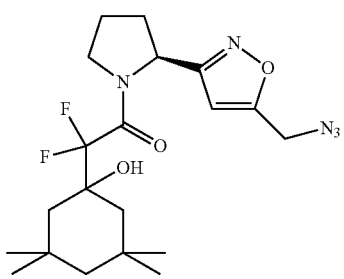 [SMILES: CC1(C)CC(C)(C)CC(O)(C(F)(F)C(=O)N2CCC[C@H]2c2cc(CN=[N+]=[N-])on2)C1]

(S)-1-(2-(5-(Azidomethyl)isoxazol-3-yl)pyrrolidin-1-yl)-2,2-difluoro-2-(1-hydroxyy-3,3,5,5-tetramethylcyclohexyl)ethanone To a mixture of toluene (20 mL) with the compound (657 mg) obtained in Example 3-(4), DBU (368 µL) and DPPA (530 µL) were added and the resulting mixture was stirred at room temperature for 20 hours. To the reaction mixture, water (50 mL) was added and the organic layer extracted with AcOEt (50 mL) was washed with brine (50 mL), dried (MgSO$_4$), filtered and concentrated to give a crude product, which was further purified by neutral silica gel chromatography (AcOEt/hexane) to give the titled compound (645 mg, colorless amorphous.)
ESI/APCI Dual 426 (M+H)$^+$ Example 4-(2)

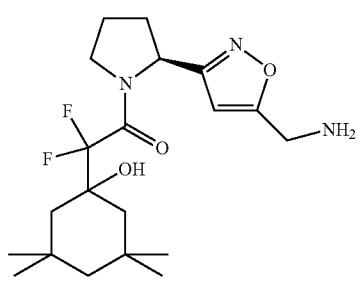 [SMILES: CC1(C)CC(C)(C)CC(O)(C(F)(F)C(=O)N2CCC[C@H]2c2cc(CN)on2)C1]

(S)-1-(2-(5-(Aminomethyl)isoxazol-3-yl)pyrrolidin-1-yl)-2,2-difluoro-2-(1-hydroxy-3,3,5,5-tetramethylcyclohexyl)ethanone (Compound 42)

To a THF (20 mL) solution of the compound (632 mg) obtained in Example 4-(1), PPh$_3$ (779 mg) and water (1.0 mL) were added and the mixture was heated under reflux for 3 hours. The reaction mixture was concentrated and after adding water (50 mL), extraction with AcOEt (50 mL×2), drying (Na$_2$SO$_4$), filtering and concentrating were performed to give a crude product, which was further purified by NH-form silica gel chromatography (AcOEt/hexane) and neutral silica gel chromatography (MeOH/CHCl$_3$) to give the titled compound (463 mg, colorless amorphous.)
ESI/APCI Dual 400 (M+H)$^+$ Example 4-(3)

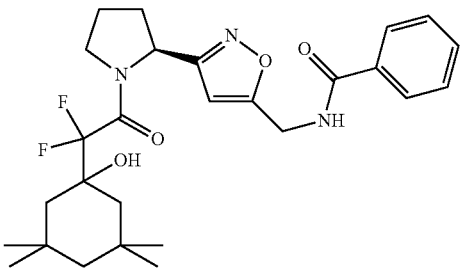 [SMILES: CC1(C)CC(C)(C)CC(O)(C(F)(F)C(=O)N2CCC[C@H]2c2cc(CNC(=O)c3ccccc3)on2)C1]

(S)—N-((3-(1-(2,2-Difluoro-2-(1-hydroxy-3,3,5,5-tetramethylcyclohexyl)acetyl)pyrrolidin-2-yl)isoxazol-5-yl)methyl)benzamide (Compound 44)

The compound (40 mg) obtained in Example 4-(2) was dissolved in CHCl$_3$ (3 ml) and after adding benzoyl chloride (17 µL) and Et$_3$N (43 µL), the mixture was stirred at room temperature for 19 hours. To the reaction mixture, CHCl$_3$ (20 ml) and 5% KHSO$_4$ (20 ml) were added to separate the organic layer. The resulting organic layer was washed with saturated aqueous sodium bicarbonate (20 ml) and brine (20 ml), dried (MgSO$_4$), filtered and concentrated to give a crude product, which was further purified by silica gel chromatography (AcOEt/hexane) to give the titled compound (43 mg, colorless amorphous.)
ESI/APCI Dual 504 (M+H)$^+$ Example 5

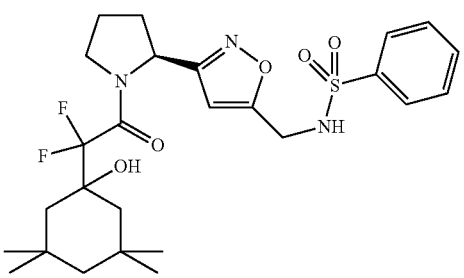 [SMILES: CC1(C)CC(C)(C)CC(O)(C(F)(F)C(=O)N2CCC[C@H]2c2cc(CNS(=O)(=O)c3ccccc3)on2)C1]

(S)—N-((3-(1-(2,2-Difluoro-2-(1-hydroxy-3,3,5,5-tetramethylcyclohexyl)acetyl)pyrrolidin-2-yl)isoxazol-5-yl)methyl)benzenesulfonamide (Compound 45)

The titled compound was obtained by repeating the procedure of Example 4-(3), except that benzoyl chloride was replaced by benzenesulfonyl chloride.
ESI/APCI Dual 540 (M+H)$^+$

Example 6

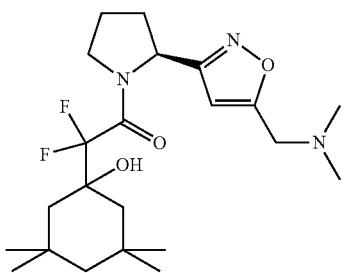

(S)-1-(2-(5-((Dimethylamino)methyl)isoxazol-3-yl)pyrrolidin-1-yl)-2,2-difluoro-2-(1-hydroxy-3,3,5,5-tetramethylcyclohexyl)ethanone (Compound 46)

The compound (160 mg) obtained in Example 3-(5) was dissolved in MeCN and after adding a THF solution of dimethylamine (2 M, 250 μL), the mixture was stirred at room temperature for 3 hours. To the reaction mixture, AcOEt (50 ml) and a saturated aqueous solution of $NaCO_3$ (50 ml) were added to separate the organic layer. The resulting organic layer was washed with brine (50 ml), dried ($MgSO_4$), filtered and concentrated to give a crude product, which was further purified by silica gel chromatography (AcOEt/hexane) to give the titled compound (83 mg, colorless amorphous.)
ESI+428 $(M+H)^+$

Example 7

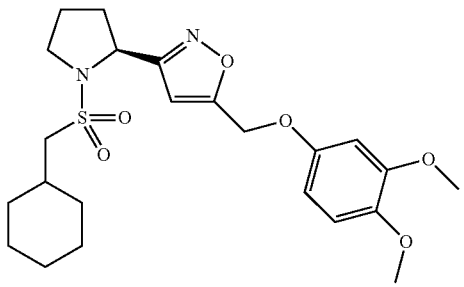 [SMILES: COc1ccc(OCc2cc([C@@H]3CCCN3S(=O)(=O)CC3CCCCC3)no2)cc1OC]

(S)-3-(1-((Cyclohexylmethyl)sulfonyl)pyrrolidin-2-yl)-5-((3,4-dimethoxyphenoxy)methyl)isoxazole (Compound 43)

To a THF (10 mL) solution of the compound (913 mg) obtained in Example 1-(1), a THF (5.0 mL) solution of $Et_3N$ (555 μL) and cyclohexylmethanesulfonyl chloride (393 mg) was added and the mixture was stirred at room temperature for 3.5 days. To the reaction mixture, a saturated aqueous solution of $NH_4Cl$ (50 mL) was added and the organic layer obtained by extraction with AcOEt (50 mL×2) was washed with brine (50 mL), dried ($MgSO_4$), filtered and concentrated to give a crude product, which was further purified by neutral silica gel chromatography (AcOEt/hexane) and NH-form silica gel chromatography (AcOEt/hexane) to give the titled compound (202 mg, colorless amorphous.)
ESI/APCI Dual 465$(M+H)^+$, 487 $(M+Na)^+$

Example 8

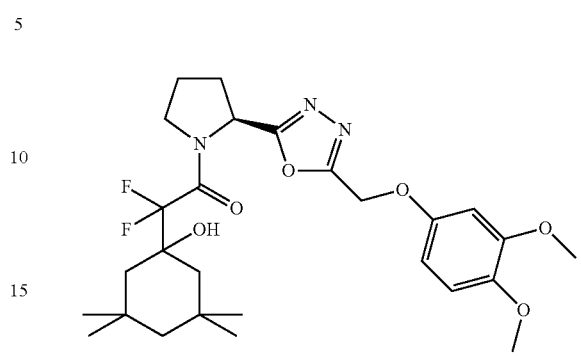

(S)-1-(2-(5-((3,4-Dimethoxyphenoxy)methyl)-1,3,4-oxadiazol-2-yl)pyrrolidin-1-yl)-2,2-difluoro-2-(1-hydroxy-3,3,5,5-tetramethylcyclohexyl)ethanone (Compound 2)

Example 8-(1)

(S)-t-Butyl 2-(2-(2-(3,4-dimethoxyphenoxy)acetyl)hydrazinecarbonyl)pyrrolidine-1-carboxylate

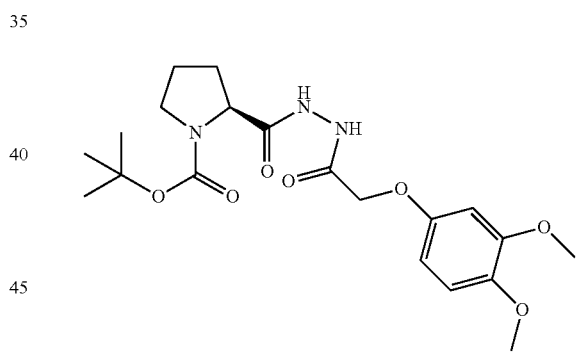

To a solution of (S)-t-butyl 2-(hydrazinecarbonyl)pyrrolidine-1-carboxylate (50.0 g) and 2-(3,4-dimethoxyphenoxy)acetic acid (47.8 g) in chloroform (1000 ml), HOBt (35.3 g) and WSC hydrochloride (50.0 g) were added and the mixture was stirred at room temperature for 4 hours. After distilling off the solvent under reduced pressure, water was added, followed by extraction with ethyl acetate. The organic layer was washed successively with saturated aqueous sodium bicarbonate and brine and dried over $MgSO_4$ before it was filtered. The solvent was distilled off under reduced pressure to give a crude form of the titled compound (61.0 g).

$^1$H NMR (200 MHz, CHLOROFORM-d) δ ppm 8.79 (br. s., 1H), 6.78 (d, J=8.79 Hz, 1H), 6.58 (d, J=2.64 Hz, 1H), 6.40 (dd, J=8.79, 3.08 Hz, 1H), 4.57 (s, 2H), 4.47-4.32 (m, 1H), 3.87 (s, 3H), 3.84 (s, 3H), 3.52-3.32 (m, 2H), 2.48-2.30 (m, 1H), 2.03-1.87 (m, 3H), 1.54-1.43 (m, 9H)

Example 8-(2)

(S)-t-Butyl 2-(5-((3,4-dimethoxyphenoxy)methyl)-1,3,4-oxadiazol-2-yl)pyrrolidine-1-carboxylate

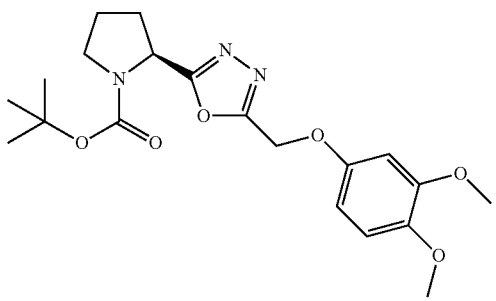 [SMILES: COc1ccc(OCc2nnc([C@@H]3CCCN3C(=O)OC(C)(C)C)o2)cc1OC]

To a toluene (700 ml) solution of the compound (61.0 g) obtained in Example 8-(1), Burgess reagent (45.0 g) was added and the mixture was stirred at 120° C. for 4 hours. After adding water to the reaction mixture, the organic layer extracted with AcOEt was dried (Na$_2$SO$_4$), filtered and had the solvent distilled off under reduced pressure; the resulting residue was purified by silica gel chromatography (AcOEt) to give the titled compound (42.0 g).

$^1$H NMR (600 MHz, CHLOROFORM-d) δ ppm 6.77 (d, J=8.71 Hz, 1H), 6.62-6.57 (m, 1H), 6.51 (dd, J=8.94, 2.98 Hz, 1H), 5.21-5.13 (m, 2H), 5.07-5.01 (m, 1H), 3.85 (s, 3H), 3.84 (s, 3H), 3.66-3.38 (m, 2H), 2.42-2.22 (m, 1H), 2.20-2.06 (m, 2H), 1.99 (m, 1H), 1.26-1.49 (m, 9H)

Example 8-(3)

(S)-2-((3,4-Dimethoxyphenoxy)methyl)-5-(pyrrolidin-2-yl)-1,3,4-oxadiazole hydrochloride

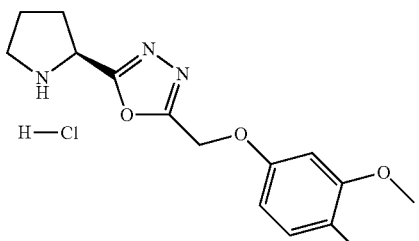

To an AcOEt (200 ml) solution of the compound (42.0 g) obtained in Example 8-(2), 4N HCl-AcOEt solution (200 ml) was added and the mixture was stirred at room temperature for 4 hours. The solvent was distilled off under reduced pressure to give a crude form of the titled compound (35.0 g).

$^1$H NMR (200 MHz, DMSO-d$_6$) δ ppm 6.88 (d, J=8.79 Hz, 1H), 6.70 (d, J=3.08 Hz, 1H), 6.64-6.55 (m, 1H), 5.38 (s, 2H), 5.13-5.00 (m, 1H), 3.75 (s, 3H), 3.70 (s, 3H), 3.34-3.23 (m, 2H), 2.44-1.90 (m, 4H)

Example 8-(4)

(S)-1-(2-(5-((3,4-Dimethoxyphenoxy)methyl)-1,3,4-oxadiazol-2-yl)pyrrolidin-1-yl)-2,2-difluoro-2-(1-hydroxy-3,3,5,5-tetramethylcyclohexyl)ethanone (Compound 2)

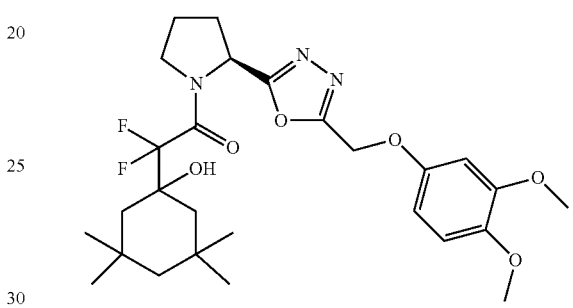

The procedure of Example 1-(2) was repeated, except that the compound obtained in Example 1-(1) was replaced by the compound (35.0 g) obtained in Example 8-(3); the resulting crude product was further purified by silica gel column chromatography (AcOEt/hexane) and thereafter recrystallized with AcOEt-pentane to give the titled compound (39.0 g) as a colorless solid.

$^1$H NMR (600 MHz, CHLOROFORM-d) δ ppm 6.80-6.77 (m, 1H), 6.62-6.60 (m, 1H), 6.50 (dd, J=8.71, 2.75 Hz, 1H), 5.50-5.46 [5.71-5.67] (m, 1H), 5.21-5.15 (m, 2H), 4.41-4.34 (m, 1H), 3.97 (s, 1H), 3.86 (s, 3H), 3.84 (s, 3H), 3.80-3.72 (m, 1H), 2.37-0.79 (m, 22H)

Example 9

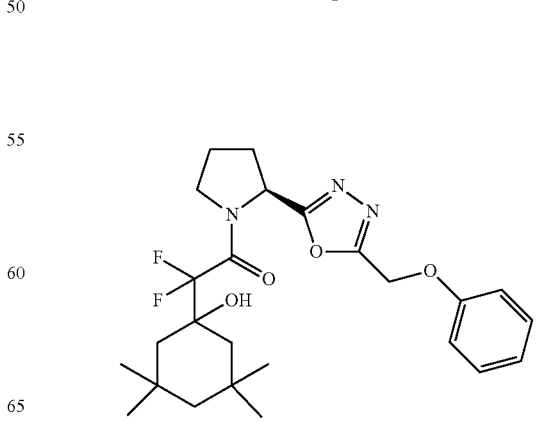

(S)-2,2-Difluoro-2-(1-hydroxy-3,3,5,5-tetramethyl-cyclohexyl)-1-(2-(5-(phenoxymethyl)-1,3,4-oxadiazol-2-yl)pyrrolidin-1-yl)ethanone (Compound 29)

Example 9-(1)

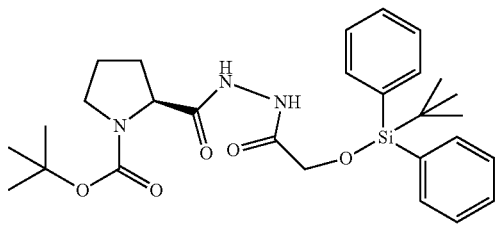 [SMILES: CC(C)(C)OC(=O)N1CCC[C@H]1C(=O)NNC(=O)CO[Si](c1ccccc1)(c1ccccc1)C(C)(C)C]

(S)-t-Butyl 2-(2-(2-((tert-butyldiphenylsilyl)oxy)acetyl)hydrazinecarbonyl)pyrrolidine-1-carboxylate A mixture of $CHCl_3$ (100 mL) with (S)-t-butyl 2-(hydrazinecarbonyl)pyrrolidine-1-carboxylate (4.791 g), 2-((t-butyldiphenylsilyl)oxy)acetic acid (6.28 g), WSC.HCl (4.371 g) and HOBt.$H_2O$ (3.081 g) was stirred at room temperature for 15 hours. To the reaction mixture, a saturated aqueous solution of $NH_4Cl$ (500 mL) was added, followed by extraction with AcOEt (500 mL). The organic layer was washed successively with saturated aqueous sodium bicarbonate (500 mL) and brine (500 mL), dried ($MgSO_4$), filtered and concentrated to give a crude product, which was further purified by silica gel chromatography (AcOEt/hexane) to give the titled compound (6.42 g, colorless amorphous.)

ESI/APCI Dual 548 (M+Na)$^+$

Example 9-(2)

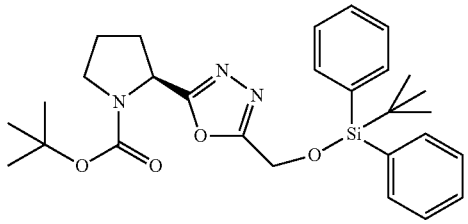 [SMILES: CC(C)(C)OC(=O)N1CCC[C@H]1c1nnc(CO[Si](c2ccccc2)(c2ccccc2)C(C)(C)C)o1]

(S)-t-Butyl 2-(5-(((tert-butyldiphenylsilyl)oxy)methyl)-1,3,4-oxadiazol-2-yl)pyrrolidine-1-carboxylate To a toluene (112 mL) solution of the compound (5.87 g) obtained in Example 9-(1), Burgess reagent (5.322 g) was added and the mixture was heated under reflux for 2.5 hours. The reaction mixture was concentrated to give a crude product, which was further purified by silica gel chromatography (AcOEt/hexane) to give the titled compound (4.151 g, colorless amorphous.)

ESI/APCI Dual 508 (M+H)$^+$, 530 (M+Na)$^+$

Example 9-(3)

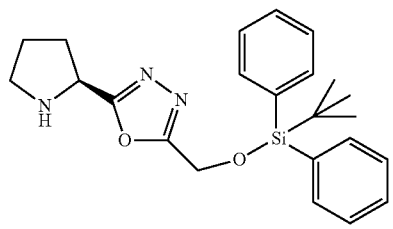 [SMILES: CC(C)(C)[Si](OCc1nnc([C@@H]2CCCN2)o1)(c1ccccc1)c1ccccc1]

(S)-2-(((tert-Butyldiphenylsilyl)oxy)methyl)-5-(pyrrolidin-2-yl)-1,3,4-oxadiazole To a THF (3.8 mL) solution of the compound (3.832 g) obtained in Example 9-(2), $H_3PO_4$ (6.1 mL, 85% aqueous solution) was added and the mixture was stirred at room temperature for an hour. To the reaction mixture, THF (50 mL) was added and the resulting mixture was added to NaOH (150 mL, 1.0 N aqueous solution) and ice (50 g), followed by extraction with $CHCl_3$ (300 mL). The organic layer was dried ($Na_2SO_4$), filtered and concentrated to give a crude product, which was further purified by NH-form silica gel chromatography (MeOH/$CHCl_3$) to give the titled compound (1.261 g, colorless oil.)

ESI/APCI Dual 408 (M+H)$^+$

Example 9-(4)

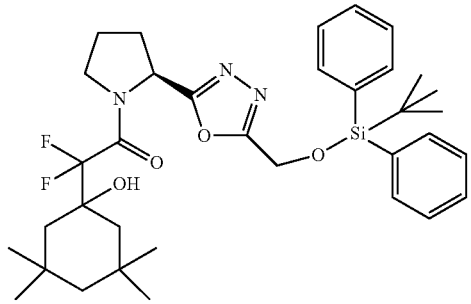 [SMILES: CC1(C)CC(C)(C)CC(O)(C(F)(F)C(=O)N2CCC[C@H]2c2nnc(CO[Si](c3ccccc3)(c3ccccc3)C(C)(C)C)o2)C1]

(S)-1-(2-(5-(((tert-Butyldiphenylsilyl)oxy)methyl)-1,3,4-oxadiazol-2-yl)pyrrolidin-1-yl)-2,2-difluoro-2-(1-hydroxy-3,3,5,5-tetramethylcyclohexyl)ethanone The procedure of Example 1-(2) was repeated, except that the compound obtained in Example 1-(1) was replaced by the compound (1.186 g) obtained in Example 9-(3); this gave the titled compound (1.287 g, colorless amorphous.)

ESI/APCI Dual 640 (M+H)$^+$, 662 (M+Na)$^+$

Example 9-(5)

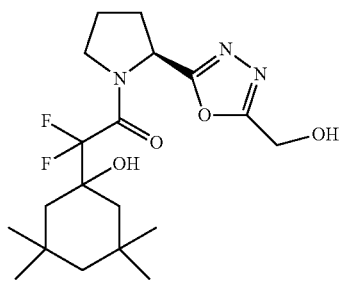 [SMILES: CC1(C)CC(C)(C)CC(O)(C(F)(F)C(=O)N2CCC[C@H]2c2nnc(CO)o2)C1]

(S)-2,2-Difluoro-2-(1-hydroxy-3,3,5,5-tetramethyl-cyclohexyl)-1-(2-(5-(hydroxymethy)-1,3,4-oxadiazol-2-yl)pyrrolidin-1-yl)ethanone (Compound 22)

The procedure of Example 3-(4) was repeated, except that the compound obtained in Example 3-(3) was replaced by the compound (1.378 g) obtained in Example 9-(4); this gave the titled compound (750 mg, colorless solid.)

ESI/APCI Dual 402 (M+H)$^+$, 424 (M+Na)$^+$

Example 9-(6)

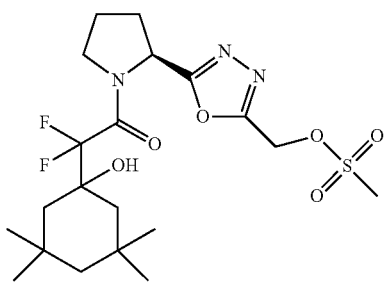 [SMILES: CC1(C)CC(C)(C)CC(O)(C(F)(F)C(=O)N2CCC[C@H]2c2nnc(COS(C)(=O)=O)o2)C1]

(S)-(5-(1-(2,2-Difluoro-2-(1-hydroxy-3,3,5,5-tetramethylcyclohexyl)acetyl)pyrrolidin-2-yl)-1,3,4-oxadiazol-2-yl)methyl methanesulfonate (Compound 23)

The procedure of Example 3-(5) was repeated, except that the compound obtained in Example 3-(4) was replaced by the compound (340 mg) obtained in Example 9-(5); the resulting crude product was recrystallized (AcOEt/hexane) to give the titled compound (7349 mg, colorless powder.)

ESI/APCI Dual 480 (M+H)$^+$, 502 (M+Na)$^+$

Example 9-(7)

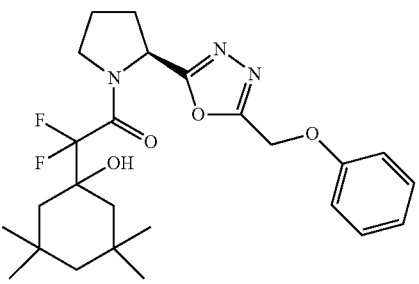 [SMILES: CC1(C)CC(C)(C)CC(O)(C(F)(F)C(=O)N2CCC[C@H]2c2nnc(COc3ccccc3)o2)C1]

(S)-2,2-Difluoro-2-(1-hydroxy-3,3,5,5-tetramethyl-cyclohexyl)-1-(2-(5-(phenoxymethyl)-1,3,4-oxadiazol-2-yl)pyrrolidin-1-yl)ethanone (Compound 29)

To a DMF (1.0 mL) solution of the compound (32.5 mg) obtained in Example 9-(6) and phenol (13 mg), K$_2$CO$_3$ (37 mg) was added and the mixture was stirred at 50° C. for 3.5 hours. The reaction mixture was added to water (20 mL) and the organic layer extracted with AcOEt (20 mL×2) was dried (MgSO$_4$), filtered and concentrated to give a crude product, which was further purified by silica gel chromatography (AcOEt/hexane) to give the titled compound (31.6 mg, colorless amorphous.)

ESI/APCI Dual 478 (M+H)$^+$, 500 (M+Na)$^+$

Example 10

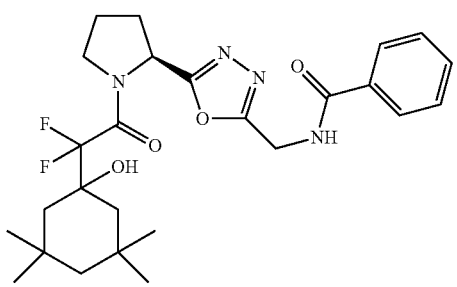 [SMILES: CC1(C)CC(C)(C)CC(O)(C(F)(F)C(=O)N2CCC[C@H]2c2nnc(CNC(=O)c3ccccc3)o2)C1]

(S)—N-((5-(1-(2,2-Difluoro-2-(1-hydroxy-3,3,5,5-tetramethylcyclohexyl)acetyl)pyrrolidin-2-yl)-1,3,4-oxadiazol-2-yl)methyl)benzamide (Compound 38)

The procedure of Example 4 was repeated, except that the compound obtained in Example 3-(4) was replaced by the compound obtained in Example 9-(6); this gave the titled compound.

ESI/APCI Dual 505 (M+H)$^+$, 527 (M+Na)$^+$

Example 11

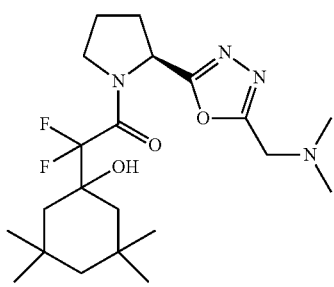

(S)-1-(2-(5-((Dimethylamino)methyl)-1,3,4-oxadiazol-2-yl)pyrrolidin-1-yl)-2,2-difluoro-2-(1-hydroxy-3,3,5,5-tetramethylcyclohexyl)ethanone (Compound 39)

The procedure of Example 6 was repeated, except that the compound obtained in Example 3-(5) was replaced by the compound obtained in Example 9-(6); this gave the titled compound.

ESI/APCI Dual 429 (M+H)⁺, 451 (M+Na)⁺

Example 12

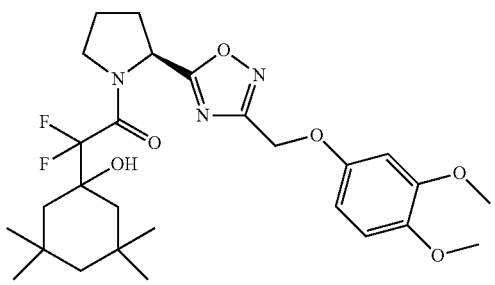

(S)-1-(2-(3-((3,4-Dimethoxyphenoxy)methyl)-1,2,4-oxadiazol-5-yl)pyrrolidin-1-yl)-2,2-difluoro-2-(1-hydroxy-3,3,5,5-tetramethylcyclohexyl)ethanone (Compound 3)

Example 12-(1)

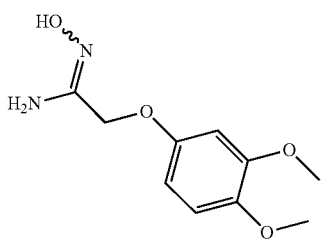 [SMILES: COc1ccc(OCC(N)=NO)cc1OC]

2-(3,4-Dimethoxyphenoxy)-N'-hydroxyacetoimidamide

To a solution of 2-(3,4-dimethoxyphenoxy)acetonitrile (3.8 g) in MeOH—H₂O (1:1), hydroxyamine hydrochloride was added and the mixture was stirred at 100° C. for 3 hours. After distilling off the solvent under reduced pressure, the residue was recovered by filtration and washed with water and hexane to give a crude form of the titled compound (4.9 g).

ESI/APCI Dual 227 (M+H)⁺, 249 (M+Na)⁺

Example 12-(2)

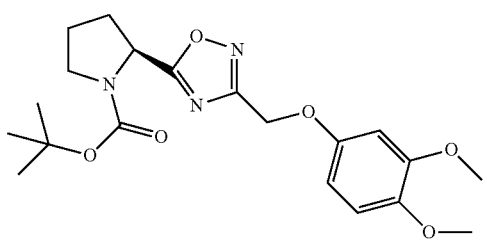 [SMILES: COc1ccc(OCc2noc([C@@H]3CCCN3C(=O)OC(C)(C)C)n2)cc1OC]

(S)-t-Butyl 2-(3-((3,4-dimethoxyphenoxy)methyl)-1,2,4-oxadiazol-5-yl)pyrrolidine-1-carboxylate To a CHCl₃ (20 ml) solution of the compound (1.0 g) obtained in Example 12-(1) and (S)-1-(tert-butoxycarbonyl)pyrrolidine-2-carboxylic acid (1.0 g), WSC.HCl (1.0 g) was added and the mixture was stirred at room temperature for 4 hours. Water was added, followed by extraction with CHCl₃. After distilling off the solvent under reduced pressure, the residue was dissolved in toluene (20 ml), followed by refluxing for 2 hours. The solvent was distilled off under reduced pressure and the residue was purified by silica gel chromatography (AcOEt/hexane) to give the titled compound (190 mg).

ESI/APCI Dual 424 (M+H)⁺, 446 (M+Na)⁺

Example 12-(3)

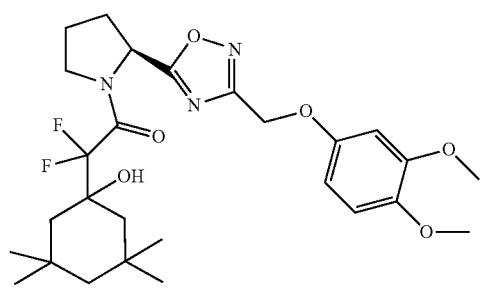

(S)-1-(2-(3-((3,4-Dimethoxyphenoxy)methyl)-1,2,4-oxadiazol-5-yl)pyrrolidin-1-yl)-2,2-difluoro-2-(1-hydroxy-3,3,5,5-tetramethylcyclohexyl)ethanone (Compound 3)

The procedures of Example 2-(3) and Example 2-(4) were repeated, except that the compound obtained in Example 2-(2) was replaced by the compound obtained in Example 12-(2); this gave the titled compound.

ESI/APCI Dual 538 (M+H)+, 560 (M+Na)+

Example 13

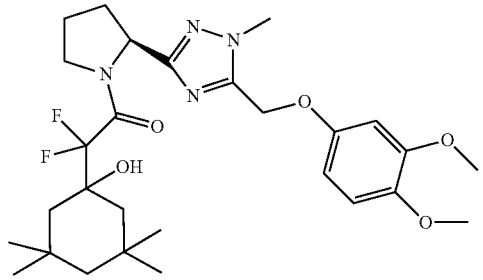

(S)-1-(2-(5-((3,4-Dimethoxyphenoxy)methyl)-1-methyl-1H-pyrazol-3-yl)pyrrolidin-1-yl)-2,2-difluoro-2-(1-hydroxy-3,3,5,5-tetramethylcyclohexyl)ethanone (Compound 9)

Example 13-(1)

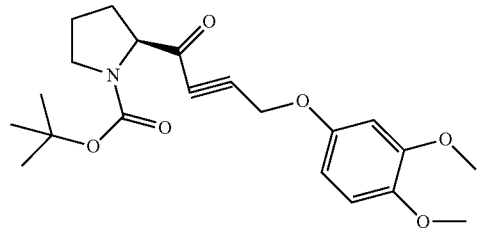 [SMILES: COc1ccc(OCC#CC(=O)[C@@H]2CCCN2C(=O)OC(C)(C)C)cc1OC]

(S)-t-Butyl 2-(4-(3,4-dimethoxyphenoxy)but-2-ynoyl)pyrrolidine-1-carboxylate

To a THF (50 mL) solution of 1,2-dimethoxy-4-(prop-2-yn-yloxy)benzene (2.118 g), n-BuLi (4.0 mL, 2.64 N hexane solution) was added dropwise at −78° C. and the resulting mixture was stirred at the same temperature for 30 minutes; the reaction mixture was then added dropwise to a solution of (S)-t-butyl 2-(methoxy(methyl)carbamoyl)pyrrolidine-1-carboxylate (2.578 g) in THF (100 mL) at −78° C. and, after stirring at the same temperature for an hour, temperature was raised to room temperature over an hour. The reaction mixture was added to a saturated aqueous solution of NH4Cl (300 mL) to separate the organic layer, which was washed with a saturated aqueous solution of NH4Cl (100 mL), dried (Na2SO4), filtered and concentrated to give a crude product, which was further purified by neutral silica gel chromatography (AcOEt/hexane) to give the titled compound (2.479 g, pale brown oil.)

ESI/APCI Dual 412 (M+Na)+

Example 13-(2)

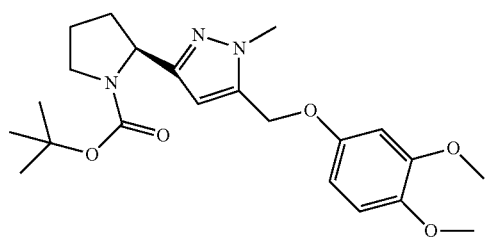 [SMILES: COc1ccc(OCc2cc([C@@H]3CCCN3C(=O)OC(C)(C)C)nn2C)cc1OC]

(S)-t-Butyl 2-(5-((3,4-dimethoxyphenoxy)methyl)-1-methyl-1H-pyrazol-3-yl)pyrrolidine-1-carboxylate To an EtOH (5.0 mL) solution of the compound (390 mg) obtained in Example 13-(1), methylhydrazine (106 μL) and sodium acetate (246 mg) were added and the mixture was heated under reflux for 20 hours. The reaction mixture was concentrated and a saturated aqueous solution of NH4Cl (50 mL) was added to separate the organic layer, which was dried (MgSO4), filtered and concentrated to give a crude product, which was further purified by neutral silica gel chromatography (AcOEt/hexane) to give the titled compound (378 mg, pale brown oil.)

ESI/APCI Dual 418 (M+H)+

Example 13-(3)

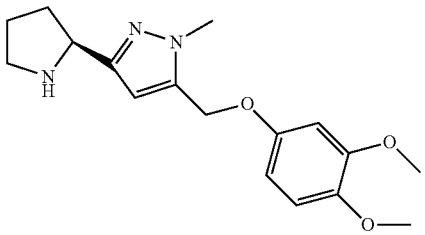 [SMILES: COc1ccc(OCc2cc([C@@H]3CCCN3)nn2C)cc1OC]

(S)-5-((3,4-Dimethoxyphenoxy)methyl)-1-methyl-3-(pyrrolidin-2-yl)-1H-pyrazole

To a CHCl3 (1.0 mL) solution of the compound (365 mg) obtained in Example 13-(2), TFA (5.0 mL) was added at 0° C. and the mixture was stirred at room temperature for 2 hours. After concentrating the reaction mixture, saturated aqueous sodium bicarbonate (50 mL) was added and the organic layer extracted with CHCl3 (50 mL×2) was dried (Na2SO4), filtered and concentrated to give the titled compound (283 mg, pale brown oil.)

ESI/APCI Dual 318 (M+H)+

Example 13-(4)

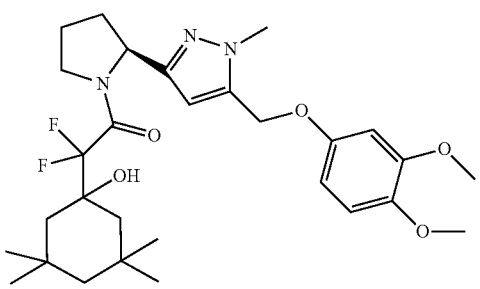

(S)-1-(2-(5-(((3,4-Dimethoxyphenoxy)methyl)-1-methyl-1H-pyrazol-3-yl)pyrrolidin-1-yl)-2,2-difluoro-2-(1-hydroxy-3,3,5,5-tetramethylcyclohexyl)ethanone (Compound 9)

The procedure of Example 1-(2) was repeated, except that the compound obtained in Example 1-(1) was replaced by the compound (274 mg) obtained in Example 13-(3); the resulting crude product was further purified by silica gel chromatography (AcOEt/hexane) to give the titled compound (129 mg, colorless amorphous.)
ESI/APCI Dual 550 (M+H)$^+$, 572 (M+Na)$^+$ Example 14

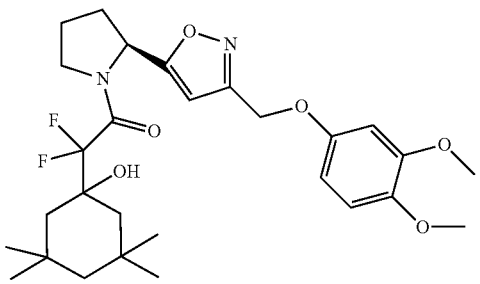

(S)-1-(2-(3-((3,4-Dimethoxyphenoxy)methyl)isoxazol-5-yl)pyrrolidin-1-yl)-2,2-difluoro-2-(1-hydroxy-3,3,5,5-tetramethylcyclohexyl)ethanone (Compound 10)

Example 14-(1)

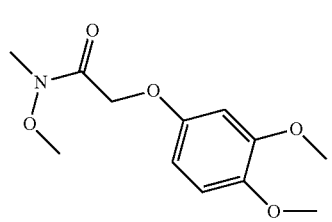

2-(3,4-Dimethoxyphenoxy)-N-methoxy-N-methylacetamide

To a mixture of CHCl$_3$ (100 mL) with 2-(3,4-dimethoxyphenoxy)acetic acid (4.244 g), N,O-dimethylhydroxyamine hydrochloride (2.341 g), WSC.HCl (4.984 g) and HOBt.H$_2$O (3.513 g), Et$_3$N (3.62 mL) was added and the mixture was stirred at room temperature for 20 hours. The reaction mixture was concentrated, H$_2$O (400 mL) was added, and the organic layer extracted with AcOEt (500 mL) was washed successively with saturated aqueous sodium dicarbonate (400 mL), water (400 mL) and brine (400 mL), dried (MgSO$_4$), filtered and concentrated to give a crude product, which was further purified by silica gel chromatography (AcOEt) to give the titled compound (4.01 g, pale brown oil.)
ESI/APCI Dual 256 (M+H)$^+$ Example 14-(2)

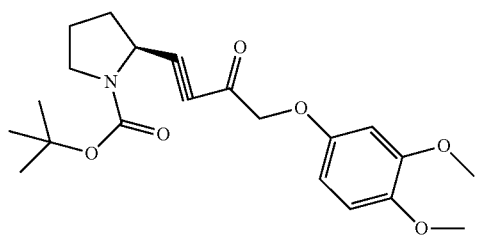 [SMILES: COc1ccc(OCC(=O)C#C[C@@H]2CCCN2C(=O)OC(C)(C)C)cc1OC]

(S)-t-Butyl 2-(4-(3,4-dimethoxyphenoxy)-3-oxobut-1-yn-1-yl)pyrrolidine-1-carboxylate To a THF (120 mL) solution of (S)-t-butyl 2-(2,2-dibromovinyl)pyrrolidine-1-carboxylate (5.326 g), n-BuLi (11.6 mL, 2.64 N hexane solution) was added dropwise at −78° C. and the mixture was stirred at the same temperature for an hour; thereafter, a THF (50 mL) solution of the compound (4.00 g) obtained in Example 14-(1) was added dropwise and temperature was raised to room temperature over an hour. The reaction mixture was added to a saturated aqueous solution of NH$_4$Cl (400 mL) and the organic layer extracted with AcOEt (400 mL×2) was dried (MgSO$_4$), filtered and concentrated to give a crude product, which was further purified by neutral silica gel chromatography (AcOEt/hexane) to give the titled compound (2.934 g, pale yellow oil.)
ESI/APCI Dual 388 (M−H)$^-$ Example 14-(3)

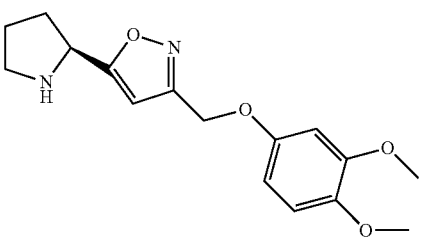 [SMILES: COc1ccc(OCc2cc([C@@H]3CCCN3)on2)cc1OC]

(S)-3-((3,4-Dimethoxyphenoxy)methyl)-5-(pyrrolidin-2-yl)isoxazole

To an EtOH (10 mL) solution of the compound (390 mg) obtained in Example 14-(2), hydroxylamine hydrochloride (139 mg) was added and the mixture was heated under reflux for 20 hours. The reaction mixture was concentrated to give a brown oil, to which CHCl$_3$ (1.0 mL) and TFA (5.0 mL) were added, followed by stirring at room temperature for 21 hours. After concentrating the reaction mixture, saturated aqueous sodium bicarbonate (50 mL) was added and the organic layer extracted with CHCl$_3$ (50 mL×2) was dried (Na$_2$SO$_4$), filtered and concentrated to give the titled compound (326 mg, brown oil) as a mixture with impurities.

ESI/APCI Dual 305 (M+H)$^+$

Example 14-(4)

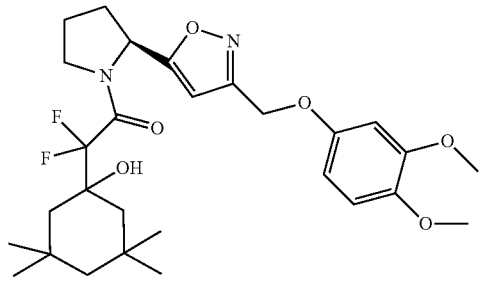

(S)-1-(2-(3-((3,4-Dimethoxyphenoxy)methyl)isoxazol-5-yl)pyrrolidin-1-yl)-2,2-difluoro-2-(1-hydroxy-3,3,5,5-tetramethylcyclohexyl)ethanone (Compound 10)

The procedure of Example 1-(2) was repeated, except that the compound obtained in Example 1-(1) was replaced by the compound (321 mg) obtained in Example 14-(3); the resulting crude product was further purified by neutral silica gel chromatography (AcOEt/hexane) and NH-form silica gel chromatography (AcOEt/hexane) to give the titled compound (142 mg, yellow amorphous.)

ESI/APCI Dual 537 (M+H)$^+$, 559 (M+Na)$^+$

Example 15

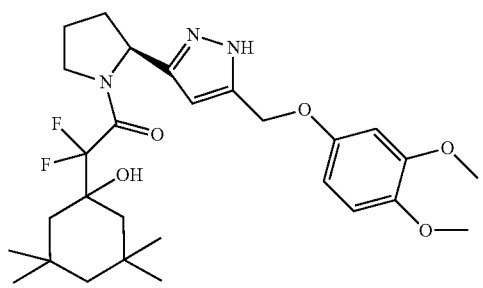

(S)-1-(2-(5-((3,4-Dimethoxyphenoxy)methyl)-1H-pyrazol-3-yl)pyrrolidin-1-yl)-2,2-difluoro-2-(1-hydroxy-3,3,5,5-tetramethylcyclohexyl)ethanone (Compound 11)

Example 15-(1)

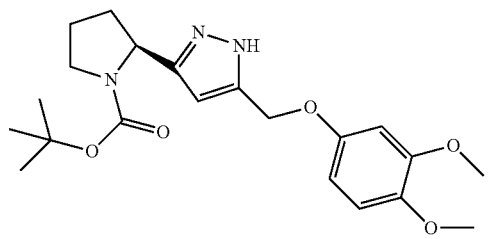 [SMILES: COc1ccc(OCc2cc([C@@H]3CCCN3C(=O)OC(C)(C)C)n[nH]2)cc1OC]

(S)-t-Butyl 2-(5-((3,4-dimethoxyphenoxy)methyl)-1H-pyrazol-3-yl)pyrrolidine-1-carboxylate To an EtOH (10 mL) solution of the compound (395 mg) obtained in Example 14-(2), hydrazine hydrate (63 μL) was added and the mixture was stirred at room temperature for 30 minutes. The reaction mixture was concentrated, water (50 mL) was added, and the organic layer extracted with AcOEt (50 mL) was dried (MgSO$_4$), filtered and concentrated to give the titled compound (466 mg, pale brown amorphous.)

ESI/APCI Dual 404 (M+H)$^+$, 426 (M+Na)$^+$

Example 15-(2)

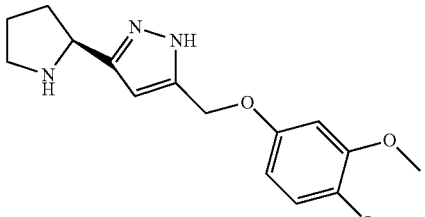

(S)-5-((3,4-Dimethoxyphenoxy)methyl)-3-(pyrrolidin-2-yl)-1H-pyrazole

The procedure of Example 13-(3) was repeated, except that the compound obtained in Example 13-(2) was replaced by the compound (460 mg) obtained in Example 15-(1); this gave the titled compound (339 mg, pale brown oil.)

ESI+304 (M+H)$^+$

Example 15-(3)

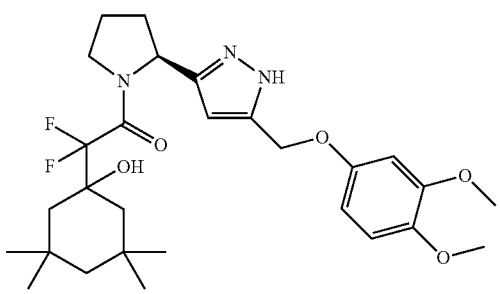

(S)-1-(2-(5-((3,4-Dimethoxyphenoxy)methyl)-1H-pyrazol-3-yl)pyrrolidin-1-yl)-2,2-difluoro-2-(1-hydroxy-3,3,5,5-tetramethylcyclohexyl)ethanone
(Compound 11)

The procedure of Example 1-(2) was repeated, except that the compound obtained in Example 1-(1) was replaced by the compound (332 mg) obtained in Example 15-(2); the resulting crude product was further purified by silica gel chromatography (AcOEt/hexane) to give the titled compound (463 mg, pale pink amorphous.)
ESI/APCI Dual 536 (M+H)$^+$, 558 (M+Na)$^+$

Example 16

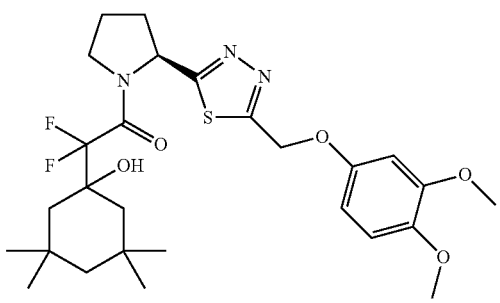

(S)-1-(2-(5-((3,4-Dimethoxyphenoxy)methyl)-1,3,4-thiadiazol-2-yl)pyrrolidin-1-yl)-2,2-difluoro-2-(1-hydroxy-3,3,5,5-tetramethylcyclohexyl)ethanone
(Compound 4)

Example 16-(1)

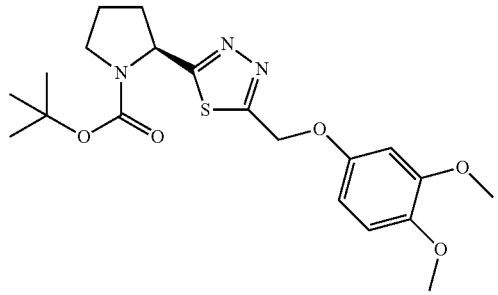

(S)-t-Butyl 2-(5-((3,4-dimethoxyphenoxy)methyl)-1,3,4-thiadiazol-2-yl)pyrrolidine-1-carboxylate To a toluene (30 ml) solution of the compound (540 mg) obtained in Example 8-(1), Lawesson's reagent (750 mg) was added and the mixture was stirred at 90° C. for 6 hours. After adding water, extraction was conducted with AcOEt. The solvent was distilled off under reduced pressure and the residue was purified by silica gel chromatography (AcOEt/hexane) to give the titled compound (291 mg).
ESI/APCI Dual 422 (M+H)$^+$, 444 (M+Na)$^+$

Example 16-(2)

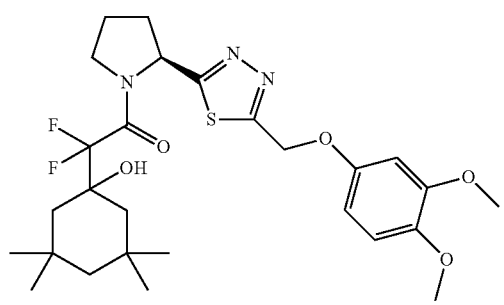

(S)-1-(2-(5-((3,4-Dimethoxyphenoxy)methyl)-1,3,4-thiadiazol-2-yl)pyrrolidin-1-yl)-2,2-difluoro-2-(1-hydroxy-3,3,5,5-tetramethylcyclohexyl)ethanone
(Compound 4)

The procedures of Example 2-(3) and Example 2-(4) were repeated, except that the compound obtained in Example 2-(2) was replaced by the compound obtained in Example 16-(1); this gave the titled compound.
ESI/APCI Dual 554 (M+H)$^+$, 576 (M+Na)$^+$

Example 17

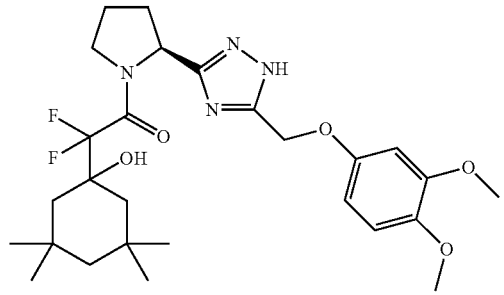

(S)-1-(2-(5-((3,4-Dimethoxyphenoxy)methyl)-4H-1,2,4-triazol-3-yl)pyrrolidin-1-yl)-2,2-difluoro-2-(1-hydroxy-3,3,5,5-tetramethylcyclohexyl)ethanone (Compound 5)

Example 17-(1)

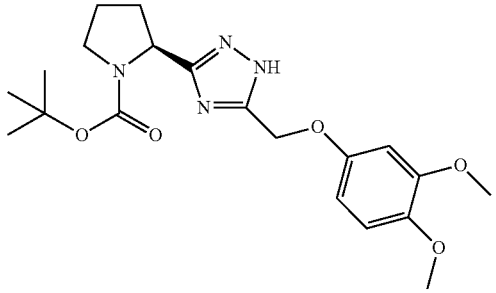 [SMILES: COc1ccc(OCc2nc([C@@H]3CCCN3C(=O)OC(C)(C)C)n[nH]2)cc1OC]

(S)-t-Butyl 2-(5-((3,4-dimethoxyphenoxy)methyl)-4H-1,2,4-triazol-3-yl)pyrrolidine-1-carboxylate To a n-butanol (10 ml) solution of 2-(3,4-dimethoxyphenoxy)acetonitrile (1.26 g) and (S)-t-butyl 2-(hydrazinecarbonyl)pyrrolidine-1-carboxylate (500 mg), $K_2CO_3$ (150 mg) was added. The resulting mixture was stirred at 160° C. for an hour under microwave irradiation. After distilling off the solvent under reduced pressure, water was added, followed by extraction with ethyl acetate. After distilling off the solvent under reduced pressure, the residue was purified by silica gel chromatography and NH-form silica gel chromatography to give the titled compound (281 mg).
ESI/APCI Dual 405 (M+H)$^+$, 427 (M+Na)$^+$ Example 17-(2)

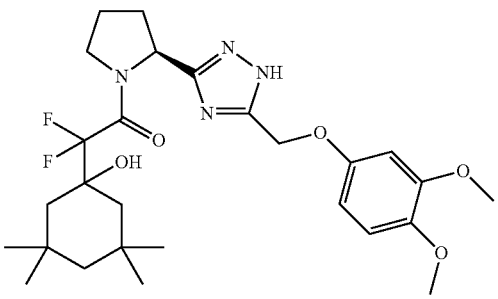

(S)-1-(2-(5-((3,4-Dimethoxyphenoxy)methyl)-4H-1,2,4-triazol-3-yl)pyrrolidin-1-yl)-2,2-difluoro-2-(1-hydroxy-3,3,5,5-tetramethylcyclohexyl)ethanone (Compound 5)

The procedures of Example 2-(3) and Example 2-(4) were repeated, except that the compound obtained in Example 2-(2) was replaced by the compound obtained in Example 17-(1); this gave the titled compound.
ESI/APCI Dual 537 (M+H)$^+$, 559 (M+Na)$^+$ Example 18

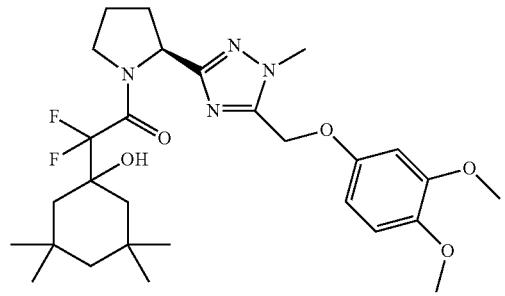

(S)-1-(2-(5-((3,4-Dimethoxyphenoxy)methyl)-1-methyl-1H-1,2,4-triazol-3-yl)pyrrolidin-1-yl)-2,2-difluoro-2-(1-hydroxy-3,3,5,5-tetramethylcyclohexyl)ethanone (Compound 8)

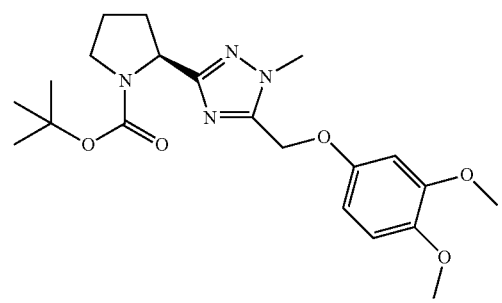 [SMILES: COc1ccc(OCc2nc([C@@H]3CCCN3C(=O)OC(C)(C)C)nn2C)cc1OC]

Example 18-(1)

(S)-t-Butyl 2-(5-((3,4-dimethoxyphenoxy)methyl)-1-methyl-1H-1,2,4-triazol-3-yl)pyrrolidine-1-carboxylate Using (S)-t-butyl 2-(2-methylhydrazinecarbonyl)pyrrolidine-1-carboxylate in place of (S)-2-(hydrazinecarbonyl)pyrrolidine-1-carboxylate, the procedure of Example 17-(1) was repeated to give the titled compound.
ESI/APCI Dual 419 (M+H)$^+$, 441 (M+Na)$^+$ Example 18-(2)

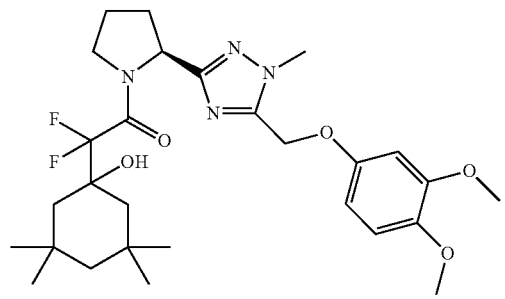

(S)-1-(2-(5-((3,4-Dimethoxyphenoxy)methyl)-1-methyl-1H-1,2,4-triazol-3-yl)pyrrolidin-1-yl)-2,2-difluoro-2-(1-hydroxy-3,3,5,5-tetramethylcyclohexyl)ethanone (Compound 8)

The procedures of Example 2-(3) and Example 2-(4) were repeated, except that the compound obtained in Example 2-(2) was replaced by the compound obtained in Example 18-(1); this gave the titled compound.

ESI/APCI Dual 551 (M+H)$^+$, 573 (M+Na)$^+$

Example 19

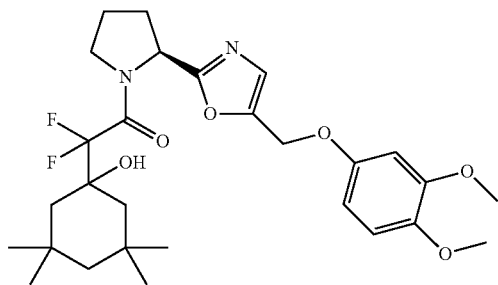

(S)-1-(2-(5-((3,4-Dimethoxyphenoxy)methyl)oxazol-2-yl)pyrrolidin-1-yl)-2,2-difluoro-2-(1-hydroxy-3,3,5,5-tetramethylcyclohexyl)ethanone (Compound 6)

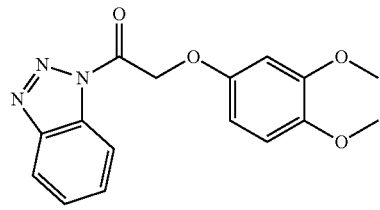 [SMILES: COc1ccc(OCC(=O)n2nnc3ccccc32)cc1OC]

Example 19-(1)

1-(1H-Benzo[d][1,2,3]triazol-1-yl)-2-(3,4-dimethoxyphenoxy)ethanone

To a solution of 1H-benzo[d][1,2,3]triazole (11.2 g) in CHCl$_3$ (120 ml), thionyl chloride (1.7 ml) was added and after stirring at room temperature for 30 minutes, 2-(3,4-dimethoxyphenoxy)acetic acid (5.00 g) was added and the mixture was stirred at room temperature for 1.5 hours. The precipitate was filtered off and the filtrate was washed with an aqueous solution of 2 N NaOH; thereafter, the organic layer was dried (MgSO$_4$), filtered and concentrated to give the titled compound (8.06 g, colorless solid.)

Example 19-(2)

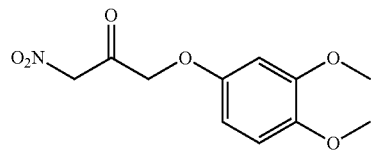

1-(3,4-Dimethoxyphenoxy)-3-nitropropan-2-one

To a suspension of potassium tert-butoxide (3.38 g) in DMSO (60 ml), a solution of nitromethane (0.836 g) in DMSO (5 ml) was added at 10° C. and the mixture was stirred at the same temperature for 30 minutes. A DMSO (65 ml) suspension of the compound (4.30 g) obtained in Example 19-(1) was added dropwise at 10° C. and the mixture was stirred at the same temperature for an hour, then at room temperature for 3 hours. The reaction mixture was poured into water (250 ml), rendered acidic with 10% aqueous acetic acid, and subjected to extraction with AcOEt. The organic layer was washed with water, dried (MgSO$_4$), filtered and concentrated to give a crude product, which was further purified by silica gel chromatography (AcOEt/hexane) and then recrystallized (AcOEt/hexane) to give the titled compound (0.808 g, pale yellow solid.)

ESI/APCI Dual 254 (M−H)$^-$

Example 19-(3)

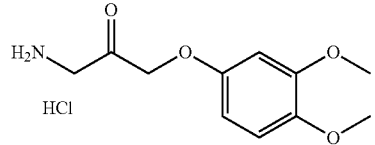 [SMILES: COc1ccc(OCC(=O)C[N+](=O)[O-])cc1OC]

1-Amino-3-(3,4-dimethoxyphenoxy)propan-2-one hydrochloride

To a MeOH (7 ml) solution of the compound (0.660 g) obtained in Example 19-(2), 10% Pd—C (0.330 g) and an aqueous solution of 1N HCl (14 ml) were added and the mixture was stirred at room temperature for 5 hours in a hydrogen gas atmosphere. The insoluble matter was filtered off and the filtrate was concentrated to give the titled compound (0.715 g, brown amorphous.)

ESI/APCI Dual 226 (M+H)$^+$

Example 19-(4)

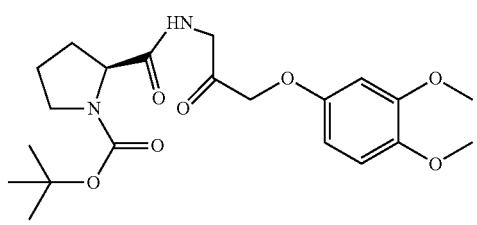 [SMILES: COc1ccc(OCC(=O)CNC(=O)[C@@H]2CCCN2C(=O)OC(C)(C)C)cc1OC]

(S)-tert-Butyl 2-((3-(3,4-dimethoxyphenoxy)-2-oxo-propyl)carbamoyl)pyrrolidine-1-carboxylate To a THF (14 ml) solution of (S)-1-(tert-butoxycarbonyl)pyrrolidine-2-carboxylic acid (0.557 g) and Et$_3$N (0.790 ml), ethyl chloroformate (0.295 g) was added over an ice bath, followed by stirring at the same temperature for 30 minutes. The reaction mixture was added at 0° C. to a THF (7 ml) solution of the compound (0.701 g) obtained in Example 19-(3) and the mixture was stirred at room temperature for 17 hours. After adding water and performing extraction with AcOEt, the organic layer was washed with saturated aqueous sodium chloride, dried (MgSO$_4$), filtered and concentrated to give a crude product, which was further purified by silica gel chromatography (AcOEt/hexane) to give the titled compound (0.540 g, brown amorphous.)

ESI/APCI Dual 445 (M+Na)$^+$

Example 19-(5)

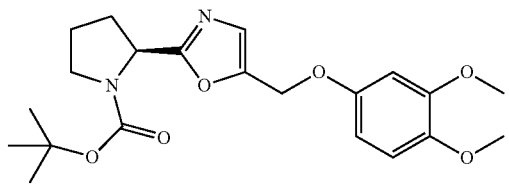 [SMILES: COc1ccc(OCc2cnc([C@@H]3CCCN3C(=O)OC(C)(C)C)o2)cc1OC]

(S)-t-Butyl 2-(5-((3,4-dimethoxyphenoxy)methyl)oxazol-2-yl)pyrrolidine-1-carboxylate To a toluene (10 ml) of the compound (0.250 g) obtained in Example 19-(4), Burgess reagent (0.281 g) was added and the mixture was stirred at 50° C. for 1.5 hours. After reversion to room temperature, the reaction mixture was concentrated to give a crude product, which was further purified by silica gel chromatography (AcOEt/hexane) to give the titled compound (0.156 g, colorless oil.)

ESI/APCI Dual 405 (M+H)$^+$

Example 19-(6)

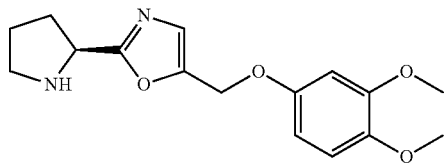 [SMILES: COc1ccc(OCc2cnc([C@@H]3CCCN3)o2)cc1OC]

(S)-5-((3,4-Dimethoxyphenoxy)methyl)-2-(pyrrolidin-2-yl)oxazole

To an AcOEt (1 ml) solution of the compound (0.146 g) obtained in Example 19-(5), 4N HCl-AcOEt (0.5 ml) was added and the mixture was stirred at room temperature for 12 hours. After adding 4N HCl-AcOEt (0.5 ml) and stirring for 3 hours, 4N HCl-AcOEt (0.5 ml) was further added and stirring was continued for an hour. After adding an aqueous solution of 2N NaOH and performing extraction with AcOEt, the organic layer was washed with brine, dried (MgSO$_4$), filtered and concentrated to give the titled compound (0.078 g, pale yellow solid.)

ESI/APCI Dual 305 (M+H)$^+$

Example 19-(7)

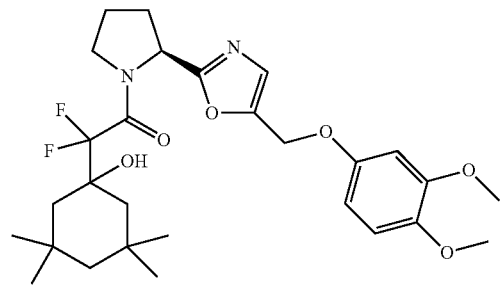

(S)-1-(2-(5-((3,4-Dimethoxyphenoxy)methyl)oxazol-2-yl)pyrrolidin-1-yl)-2,2-difluoro-2-(1-hydroxy-3,3,5,5-tetramethylcyclohexyl)ethanone (Compound 6)

To a solution of 2,2-difluoro-2-(1-hydroxy-3,3,5,5-tetramethylcyclohexyl)acetic acid (0.075 g) and Et$_3$N (0.038 ml) in THF (1 ml), ethyl chloroformate (0.028 g) was added over an ice bath, followed by stirring at the same temperature for an hour. To the reaction mixture, a solution of (S)-5-((3,4-dimethoxyphenoxy)methyl)-2-(pyrrolidin-2-yl)oxazole (0.075 g) in THF (1 ml) was added over an ice bath, followed by stirring at room temperature for 15 hours. After adding water and performing extraction with AcOEt, the organic layer was washed with saturated aqueous sodium chloride, dried (MgSO$_4$), filtered and concentrated to give a crude product, which was further purified by silica gel chromatography (AcOEt/hexane) to give the titled compound (0.104 g, colorless amorphous.)

ESI/APCI Dual 537 (M+H)$^+$

Example 20

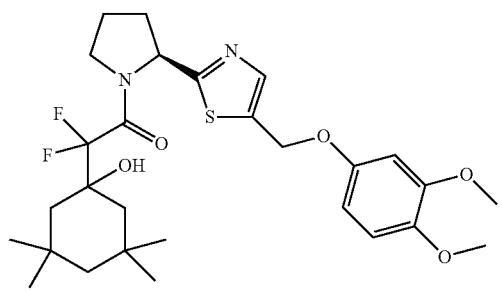

(S)-1-(2-(5-((3,4-Dimethoxyphenoxy)methyl)thiazol-2-yl)pyrrolidin-1-yl)-2,2-difluoro-2-(1-hydroxy-3,3,5,5-tetramethylcyclohexyl)ethanone
(Compound 7)

Example 20-(1)

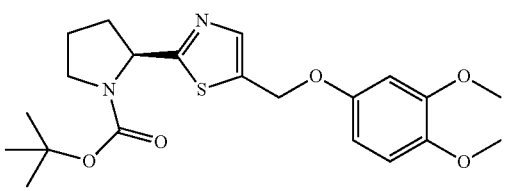 [SMILES: COc1ccc(OCc2cnc([C@@H]3CCCN3C(=O)OC(C)(C)C)s2)cc1OC]

(S)-tert-Butyl 2-(5-((3,4-dimethoxyphenoxy)methyl)thiazol-2-yl)pyrrolidine-1-carboxylate To a toluene (5 ml) solution of the compound (0.287 g) obtained in Example 19-(4), Lawesson's reagent (0.275 g) was added and the mixture was stirred at 110° C. for an hour. After reversion to room temperature, the reaction mixture was concentrated to give a crude product, which was further purified by silica gel chromatography (AcOEt/hexane) to give the titled compound (0.100 g, colorless amorphous.)
ESI/APCI Dual 421 (M+H)$^+$

Example 20-(2)

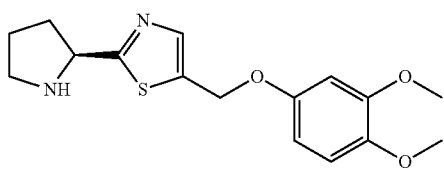 [SMILES: COc1ccc(OCc2cnc([C@@H]3CCCN3)s2)cc1OC]

(S)-5-((3,4-Dimethoxyphenoxy)methyl)-2-(pyrrolidin-2-yl)thiazole

The procedure of Example 19-(6) was repeated, except that the compound obtained in Example 19-(5) was replaced by the compound obtained in Example 20-(2); this gave the titled compound (0.063 g, colorless solid.)
ESI/APCI Dual 321 (M+H)$^+$

Example 20-(3)

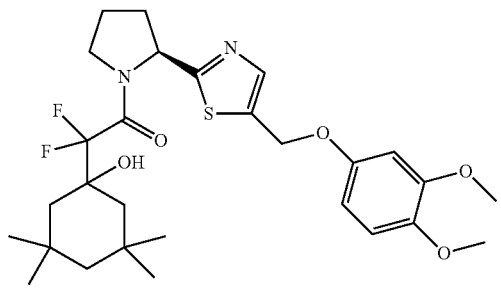

(S)-1-(2-(5-((3,4-Dimethoxyphenoxy)methyl)thiazol-2-yl)pyrrolidin-1-yl)-2,2-difluoro-2-(1-hydroxy-3,3,5,5-tetramethylcyclohexyl)ethanone
(Compound 7)

The procedure of Example 19-(7) was repeated, except that the compound obtained in Example 19-(6) was replaced by the compound obtained in Example 20-(2); this gave the titled compound (0.077 g, colorless amorphous.)
ESI/APCI Dual 575 (M+Na)$^+$

Example 21

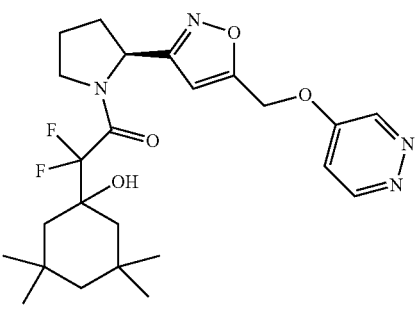 [SMILES: CC1(C)CC(C)(C)CC(O)(C(F)(F)C(=O)N2CCC[C@H]2c2cc(COc3ccnnc3)on2)C1]

(S)-2,2-Difluoro-2-(1-hydroxy-3,3,5,5-tetramethylcyclohexyl)-1-(2-(5-((pyridazin-4-yloxy)methyl)isoxazol-3-yl)pyrrolidin-1-yl)ethanone
(Compound 53)

A sealed tube was charged with a mixture prepared by adding toluene (2 ml) to Compound 18 (30 mg), 4-bromopyridazine hydrobromide (22 mg), Pd(OAc)$_2$ (2 mg), Cs$_2$CO$_3$ (37 mg), and [1,1'-binaphthalen]-2-yldi-tert-butylphosphine (3 mg) and the mixture was stirred at 100° C. for 4 hours. After cooling the reaction mixture to room temperature, NH silica gel was added, followed by stirring for a while. After separating the silica gel by filtration, the silica gel was washed with chloroform and the solvent was distilled off; the resulting residue was purified by reverse-phase preparative HPLC to give the titled compound (6.0 mg, colorless oil.)

1H NMR (600 MHz, CHLOROFORM-d) δ=9.08-8.98 (m, 2H), 7.02-6.96 (m, 1H), 6.35 [6.26] (s, 1H), 5.62-5.37 (m, 1H), 5.22[5.24] (s, 2H), 4.21-3.71 (m, 2H), 2.38-0.82 (m, 22H)

Example 22

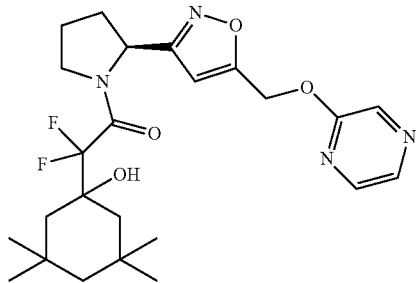 [SMILES: CC1(C)CC(C)(C)CC(O)(C(F)(F)C(=O)N2CCC[C@H]2c2cc(COc3cnccn3)on2)C1]

(S)-2,2-Difluoro-2-(1-hydroxy-3,3,5,5-tetramethyl-cyclohexyl)-1-(2-(5-((pyrazin-2-yloxy)methyl)isoxazol-3-yl)pyrrolidin-1-yl)ethanone (Compound 55)

To a solution of Compound 18 (40 mg) in DMF (1.0 ml), NaH (5.2 mg, >55% in mineral oil) was added and after stirring for 30 minutes, 2-bromopyrazine (23.8 mg) was added and the mixture was stirred at room temperature for 0.5 hour.
To the reaction mixture, DMSO (1.0 ml) was added and after filtering off the insoluble matter, the filtrate was purified by reverse-phase preparative HPLC to give the titled compound (6.7 mg, colorless oil.)
1H NMR (600 MHz, CHLOROFORM-d) δ 8.34-8.29 (m, 1H), 8.24-8.18 (m, 1H), 8.13-8.08 (m, 1H), 6.28 [6.19] (s, 1H), 5.60-5.36 (m, 3H), 4.24-4.13 (m, 1H), 3.95-3.87 (m, 1H), 3.82-3.69 (m, 1H), 2.35-0.76 (m, 22H)

Example 23

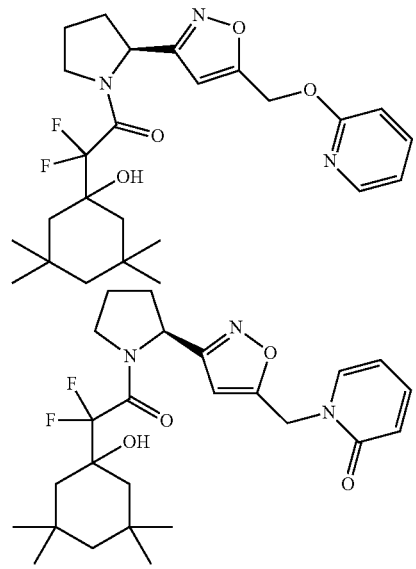

(S)-2,2-Difluoro-2-(1-hydroxy-3,3,5,5-tetramethyl-cyclohexyl)-1-(2-(5-((pyridin-2-yloxy)methyl)isoxazol-3-yl)pyrrolidin-1-yl)ethanone (Compound 54); and (S)-1-((3-(1-(2,2-Difluoro-2-(1-hydroxy-3,3,5,5-tetramethylcyclohexyl)acetyl)pyrrolidin-2-yl)isoxazol-5-yl)methyl)pyridin-2(1H)-one (Compound 60)

To a DMF (1.0 mL) solution of the compound (30 mg) obtained in Example 3-(5) and pyridin-2-ol (12 mg), K$_2$CO$_3$ (35 mg) was added and the mixture was stirred at 50° C. for an hour. To the reaction mixture, DMSO (1.0 ml) was added and after filtering off the insoluble matter, the filtrate was purified by reverse-phase preparative HPLC to give Compound 54 (2.0 mg, colorless oil) and Compound 60 (16.0 mg, colorless oil.)

(S)-2,2-Difluoro-2-(1-hydroxy-3,3,5,5-tetramethyl-cyclohexyl)-1-(2-(5-((pyridin-2-yloxy)methyl)isoxazol-3-yl)pyrrolidin-1-yl)ethanone (Compound 54)

1H NMR (600 MHz, CHLOROFORM-d) δ 8.20-8.12 (m, 1H), 7.66-7.57 (m, 1H), 6.97-6.90 (m, 1H), 6.85-6.78 (m, 1H), 6.24 [6.15] (s, 1H), 5.59-5.30 (m, 3H), 4.25-4.14 (m, 1H), 4.05-3.92 (m, 1H), 3.81-3.69 (m, 1H), 2.33-0.77 (m, 22H)

(S)-1-((3-(1-(2,2-Difluoro-2-(1-hydroxy-3,3,5,5-tetramethylcyclohexyl)acetyl)pyrrolidin-2-yl)isoxazol-5-yl)methyl)pyridin-2(1H)-one (Compound 60)

1H NMR (600 MHz, CHLOROFORM-d) δ 7.42-7.31 (m, 2H), 6.59 (d, J=9.1 Hz, 1H), 6.28-6.11 (m, 2H), 5.56-5.07 (m, 3H), 4.23-4.09 (m, 1H), 3.98-3.83 (m, 1H), 3.80-3.67 (m, 1H), 2.35-0.72 (m, 22H)

Example 24

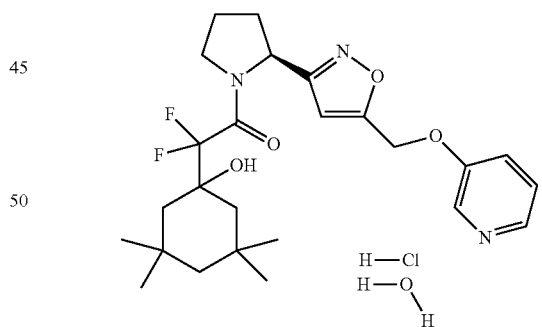

(S)-2,2-Difluoro-2-(1-hydroxy-3,3,5,5-tetramethyl-cyclohexyl)-1-(2-(5-((pyridin-3-yloxy)methyl)isoxazol-3-yl)pyrrolidin-1-yl)ethanone hydrochloride monohydrate (Compound 67)

To an AcOEt (50 ml) solution of Compound 40 (2.24 g) obtained in Example 2, HCl (50 ml, 4.0 N in AcOEt) was added and the mixture was stirred at room temperature for 15 hours, and after adding pentane (140 ml), the mixture was stirred for 8 days. The residue obtained by concentrating the reaction mixture was recrystallized (MeOH/Et₂O) to give the titled compound (2.23 g, colorless powder.)

¹H NMR (600 MHz, DMSO-d₆) δ=8.65-8.52 (m, 1H), 8.46-8.36 (m, 1H), 7.97-7.84 (m, 1H), 7.75-7.65 (m, 1H), 6.61 [6.63] (s, 1H), 5.79-3.01 (m, 7H), 5.42 [5.44] (s, 2H), 2.31-0.66 (m, 22H)

Anal. calcd for $C_{25}H_{33}F_2N_3O_4 \cdot HCl \cdot H_2O$: C, 56.44; H, 6.82; N, 7.90. found C, 56.20; H, 6.66; N, 7.76.

The procedure of Example 3 was repeated to give the following compounds.

(S)-2,2-Difluoro-2-(1-hydroxy-3,3,5,5-tetramethyl-cyclohexyl)-1-(2-(5-(((6-methoxypyridin-3-yl)oxy)methyl)isoxazol-3-yl)pyrrolidin-1-yl)ethanone (Compound 41)

1H NMR (600 MHz, CHLOROFORM-d) δ 7.91-7.82 (m, 1H), 7.30-7.21 (m, 1H), 6.74-6.66 (m, 1H), 6.39-6.15 (m, 1H), 5.60-5.33 (m, 1H), 5.12-5.02 (m, 2H), 3.89 (s, 3H), 4.24-3.64 (m, 3H), 2.35-0.84 (m, 22H)

(S)-2,2-Difluoro-2-(1-hydroxy-3,3,5,5-tetramethyl-cyclohexyl)-1-(2-(5-(phenoxymethyl)isoxazol-3-yl)pyrrolidin-1-yl)ethanone (Compound 52)

1H NMR (600 MHz, CHLOROFORM-d) δ 7.37-7.28 (m, 2H), 7.05-6.92 (m, 3H), 6.26 [6.18] (s, 1H), 5.44-5.37 [5.60-5.54] (m, 1H), 5.17-5.05 (m, 2H), 4.41-3.54 (m, 3H), 2.39-0.68 (m, 22H)

(S)-2,2-Difluoro-2-(1-hydroxy-3,3,5,5-tetramethyl-cyclohexyl)-1-(2-(5-((pyrimidin-5-yloxy)methyl)isoxazol-3-yl)pyrrolidin-1-yl)ethanone (Compound 59)

1H NMR (600 MHz, CHLOROFORM-d) δ 8.93 (s, 1H), 8.49 (s, 2H), 6.34 [6.25] (s, 1H), 5.44-5.36 [5.61-5.56] (m, 1H), 5.26-5.17 (m, 2H), 4.21-4.11 (m, 1H), 3.89-3.70 (m, 2H), 2.38-0.77 (m, 22H)

(S)-2,2-Difluoro-1-(2-(5-((3-fluorophenoxy)methyl)isoxazol-3-yl)pyrrolidin-1-yl)-2-(1-hydroxy-3,3,5,5-tetramethylcyclohexyl)ethanone (Compound 64)

1H NMR (600 MHz, CHLOROFORM-d) δ 7.30-7.21 (m, 1H), 6.77-6.65 (m, 3H), 6.27 [6.18] (s, 1H), 5.44-5.38 [5.59-5.55] (m, 1H), 5.15-5.05 (m, 2H), 4.23-4.14 (m, 1H), 3.93-3.87 (m, 1H), 3.84-3.70 (m, 1H), 2.35-0.78 (m, 22H)

(S)-2,2-Difluoro-2-(1-hydroxy-3,3,5,5-tetramethyl-cyclohexyl)-1-(2-(5-((p-toluoyloxy)methyl)isoxazol-3-yl)pyrrolidin-1-yl)ethanone (Compound 65)

1H NMR (600 MHz, CHLOROFORM-d) δ 7.13-7.08 (m, 2H), 6.87-6.82 (m, 2H), 6.25 [6.17] (s, 1H), 5.44-5.37 [5.58-5.55] (m, 1H), 5.13-5.04 (m, 2H), 4.24-4.15 (m, 1H), 3.98-3.91 (m, 1H), 3.82-3.69 (m, 1H), 2.30 (s, 3H), 2.25-0.86 (m, 22H)

The procedure of Example 21 was repeated to give the following compound.

(S)-2,2-Difluoro-2-(1-hydroxy-3,3,5,5-tetramethyl-cyclohexyl)-1-(2-(5-((pyridin-4-yloxy)methyl)isoxazol-3-yl)pyrrolidin-1-yl)ethanone (Compound 57)

1H NMR (600 MHz, CHLOROFORM-d) δ 8.49 (br. s., 2H), 6.93-6.82 (m, 2H), 6.30 [6.21] (s, 1H), 5.46-5.35 [5.61-5.55] (m, 1H), 5.21-5.10 (m, 2H), 4.24-4.08 (m, 1H), 3.92-3.69 (m, 2H), 2.40-0.75 (m, 22H)

The procedure of Example 22 was repeated to give the following compounds.

(S)-2,2-Difluoro-2-(1-hydroxy-3,3,5,5-tetramethyl-cyclohexyl)-1-(2-(5-((pyridazin-3-yloxy)methyl)isoxazol-3-yl)pyrrolidin-1-yl)ethanone (Compound 56)

1H NMR (600 MHz, CHLOROFORM-d) δ 8.93-8.86 (m, 1H), 7.47-7.40 (m, 1H), 7.10-7.02 (m, 1H), 6.35 [6.25] (s, 1H), 5.70-5.60 (m, 2H), 5.44-5.37 [5.60-5.56] (m, 1H), 4.25-4.13 (m, 1H), 3.99-3.87 (m, 1H), 3.82-3.69 (m, 1H), 2.35-0.77 (m, 22H)

(S)-2,2-Difluoro-2-(1-hydroxy-3,3,5,5-tetramethyl-cyclohexyl)-1-(2-(5-((pyrimidin-2-yloxy)methyl)isoxazol-3-yl)pyrrolidin-1-yl)ethanone (Compound 58)

1H NMR (600 MHz, CHLOROFORM-d) δ 8.59-8.52 (m, 2H), 7.06-6.99 (m, 1H), 6.30 [6.23] (s, 1H), 5.63-5.35 (m, 3H), 4.26-4.14 (m, 1H), 4.02-3.91 (m, 1H), 3.82-3.68 (m, 1H), 2.38-0.75 (m, 22H)

The procedure of Example 23 was repeated to give the following compounds.

(S)-1-((3-(1-(2,2-Difluoro-2-(1-hydroxy-3,3,5,5-tetramethylcyclohexyl)acetyl)pyrrolidin-2-yl)isoxazol-5-yl)methyl)pyrimidin-4(1H)-one (Compound 61)

1H NMR (600 MHz, CHLOROFORM-d) δ 8.22-8.10 (m, 1H), 7.36-7.30 (m, 1H), 6.33-6.15 (m, 2H), 5.40-5.30 [5.60-5.54] (m, 1H), 5.02-4.96 (m, 2H), 4.17-4.06 (m, 1H), 3.86-3.60 (m, 2H), 2.36-0.77 (m, 22H)

(S)-3-((3-(1-(2,2-Difluoro-2-(1-hydroxy-3,3,5,5-tetramethylcyclohexyl)acetyl)pyrrolidin-2-yl)isoxazol-5-yl)methyl)pyrimidin-4(3H)-one (Compound 62)

1H NMR (600 MHz, CHLOROFORM-d) δ 8.26-8.21 (m, 1H), 7.95-7.87 (m, 1H), 6.50-6.46 (m, 1H), 6.28 [6.21] (s, 1H), 5.40-5.31 [5.57-5.50] (m, 1H), 5.21-5.11 (m, 2H), 4.21-4.08 (m, 1H), 3.91-3.68 (m, 2H), 2.31-0.83 (m, 22H)

(S)-2,2-Difluoro-2-(1-hydroxy-3,3,5,5-tetramethyl-cyclohexyl)-1-(2-(5-((pyrimidin-4-yloxy)methyl)isoxazol-3-yl)pyrrolidin-1-yl)ethanone (Compound 63)

1H NMR (600 MHz, CHLOROFORM-d) δ 8.81 (s, 1H), 8.53-8.46 (m, 1H), 6.85-6.79 (m, 1H), 6.29 [6.20] (s, 1H), 5.63-5.34 (m, 3H), 4.24-4.13 (m, 1H), 3.97-3.68 (m, 2H), 2.38-0.77 (m, 22H)

(S)-1-((3-(1-(2,2-Difluoro-2-(1-hydroxy-3,3,5,5-tetramethylcyclohexyl)acetyl)pyrrolidin-2-yl)isoxazol-5-yl)methyl)pyridin-4(1H)-one (Compound 66)

1H NMR (600 MHz, CHLOROFORM-d) δ 7.36-7.30 (m, 2H), 6.44-6.38 (m, 2H), 6.16 [6.08] (s, 1H), 5.61-5.31 (m, 1H), 5.06-4.91 (m, 2H), 4.22-4.07 (m, 1H), 3.92-3.62 (m, 2H), 2.38-0.77 (m, 22H)

Reference Example

In Example 2-(2), the following intermediate as generated in situ was used to perform cyclization; if desired, this intermediate may be isolated before the cyclization.

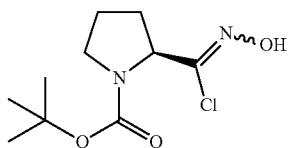 [SMILES: CC(C)(C)OC(=O)N1CCC[C@H]1C(Cl)=NO]

(S)-tert-Butyl 2-(chloro(hydroxyimino)methyl)pyrrolidine-1-carboxylate

To an AcOEt (270 ml) solution of the (S)-t-butyl 2-((hydroxyimino)methyl)pyrrolidine-1-carboxylate (32.0 g) obtained in Example 2-(1), NMP (43.1 ml) was added and after adding NCS (21.94 g) in three divided portions at 20- to 30-min intervals at 30 to 40° C., the resulting mixture was stirred at room temperature for 0.5 hour. The same reaction was carried out in a total of four runs using the same quantities. To the reaction mixture, water (400 ml) was added and the organic layer was separated. The separated organic layers were combined, washed with water (1.2 L×2), dried (MgSO4), filtered and concentrated to give a crude product (pale yellow solid, 174 g), which was washed with AcOEt/hexane (AcOEt/hexane=140 ml/840 ml) and dried to give the titled compound (109.3 g, colorless solid.)

1H NMR (600 MHz, DMSO-d6) δ 11.77-11.62 (m, 1H), 4.55-4.41 (m, 1H), 3.58-3.20 (m, 2H), 2.25-1.71 (m, 4H), 1.39 [1.33] (s., 9H)

ESI/APCI Dual 237 (M+Na)$^+$

Using methods either the same as or similar to those described in Examples 1-24, the compounds identified in Table 1-1 to Table 1-11 were prepared.

TABLE 1-1

| Compound No. | Structural formula | PKBP12 rotamase inhibiting activity IC50 (nM) | MS ESI/APCI dual | Preparation method |
|---|---|---|---|---|
| Compound 1 | | 49 | 559 (M + Na)+ | Example 1 |
| Compound 2 | | 62 | 538 (M + H)+ | Example 8 |
| Compound 3 | | 500~1,000 | 538 (M + H)+ | Example 12 |

TABLE 1-1-continued
| Compound No. | Structural formula | PKBP12 rotamase inhibiting activity IC50 (nM) | MS ESI/APCI dual | Preparation method |
|---|---|---|---|---|
| Compound 4 | 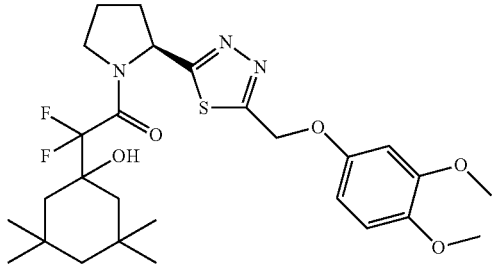 | 145 | 554 (M + H)+ | Example 16 |
| Compound 5 | 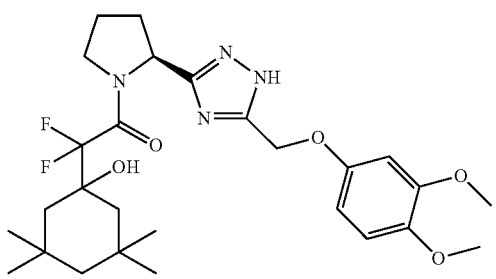 | 119 | 537 (M + H)+ | Example 17 |
| Compound 6 | 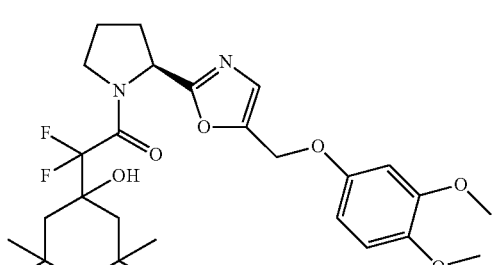 | 500~1,000 | 537 (M + H)+ | Example 19 |
TABLE 1-2
| Compound 7 | 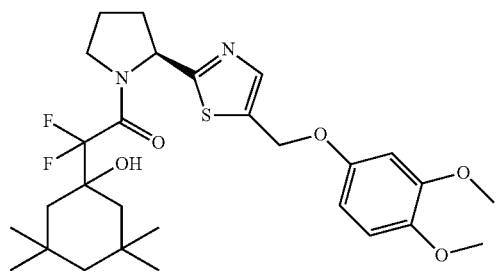 | 500~1,000 | 575 (M + Na)+ | Example 20 |
|---|---|---|---|---|
| Compound 8 | 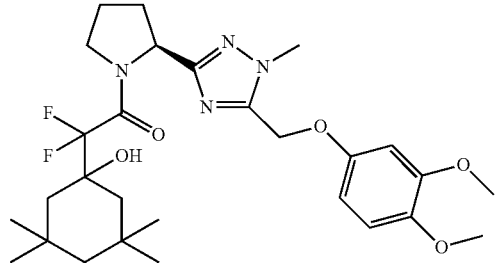 | 189 | 551 (M + H)+ | Example 18 |

TABLE 1-2-continued

| | Structure | IC50 | MS | Example |
|---|---|---|---|---|
| Compound 9 | 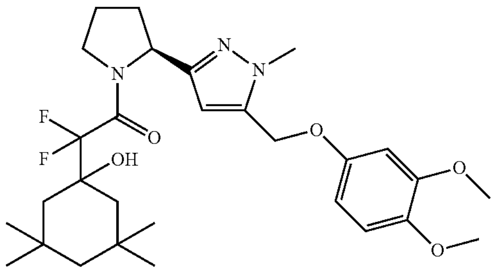 | 500~1,000 | 550 (M + H)+ | Example 13 |
| Compound 10 | 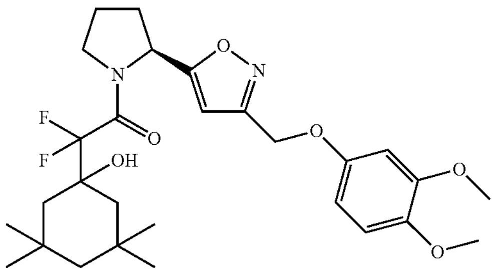 | 500~1,000 | 559 (M + Na)+ | Example 14 |
| Compound 11 | 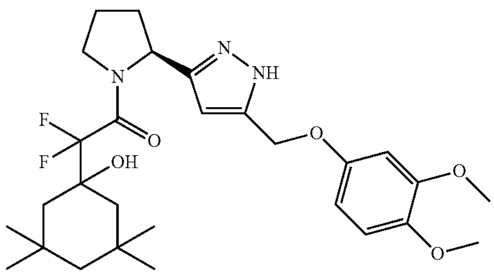 | 235 | 536 (M + H)+ | Example 15 |
| Compound 12 | 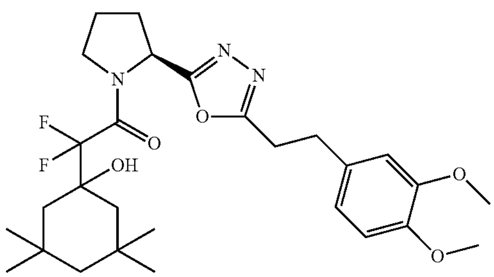 | 270 | 536 (M + H)+ | As in Example 8 |

TABLE 1-3

| | Structure | IC50 | MS | Example |
|---|---|---|---|---|
| Compound 13 | 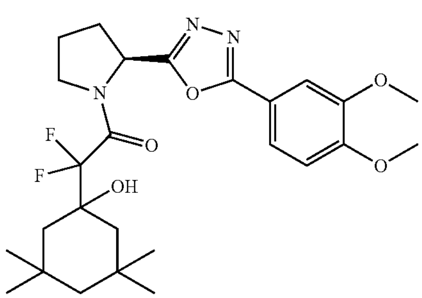 | 434 | 508 (M + H)+ | As in Example 8 |

TABLE 1-3-continued

| Compound | Structure | IC50 | MS | Method |
|---|---|---|---|---|
| Compound 14 | 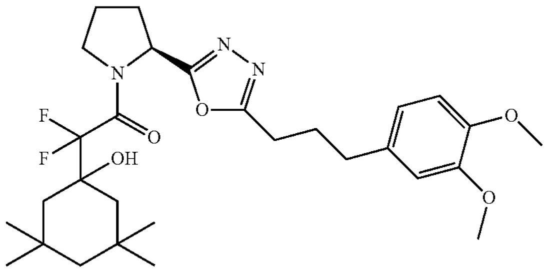 | 500~1,000 | 550 (M + H)+ | As in Example 8 |
| Compound 15 | 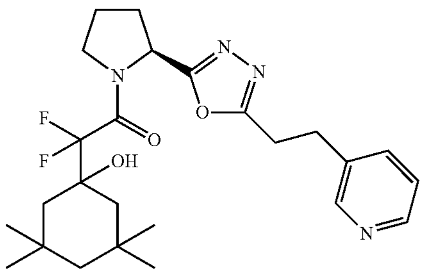 [SMILES: CC1(C)CC(C)(C)CC(O)(C(F)(F)C(=O)N2CCC[C@H]2c2nnc(CCc3cccnc3)o2)C1] | 244 | 406 (M − H)− | As in Example 8 |
| Compound 16 | 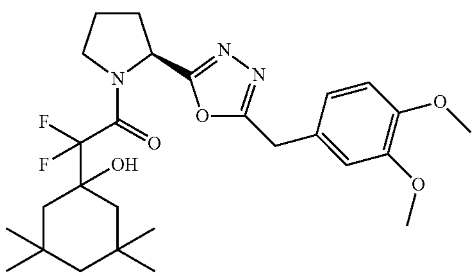 | 142 | 522 (M + H)+ | As in Example 8 |
| Compound 17 | 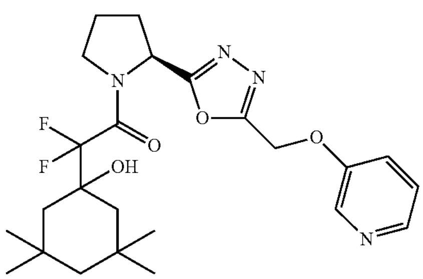 [SMILES: CC1(C)CC(C)(C)CC(O)(C(F)(F)C(=O)N2CCC[C@H]2c2nnc(COc3cccnc3)o2)C1] | 356 | 479 (M + H)+ | As in Example 9 |
| Compound 18 | 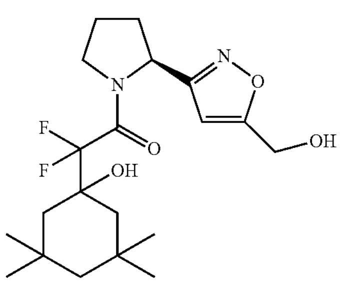 [SMILES: CC1(C)CC(C)(C)CC(O)(C(F)(F)C(=O)N2CCC[C@H]2c2cc(CO)on2)C1] | 500~1,000 | 423 (M + Na)+ | Example 3-(4) |

TABLE 1-4
| Compound 19 | 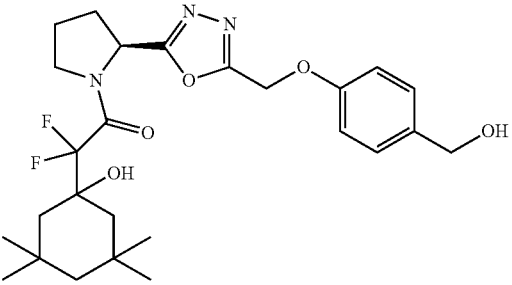 [SMILES: CC1(C)CC(C)(C)CC(O)(C(F)(F)C(=O)N2CCC[C@H]2c2nnc(COc3ccc(CO)cc3)o2)C1] | 229 | 530 (M + Na)+ | As in Example 9 |
| --- | --- | --- | --- | --- |
| Compound 20 | 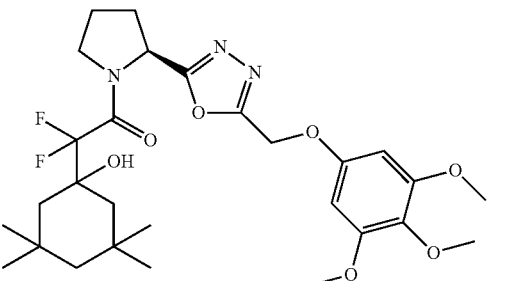 | 276 | 568 (M + H)+ | As in Example 9 |
| Compound 21 | 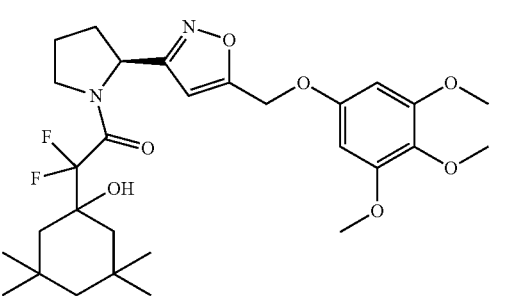 | 64 | 589 (M + Na)+ | Example 3 |
| Compound 22 | 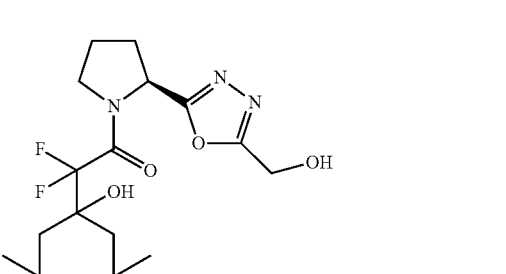 | 1,000~2,000 | 402 (M + H)+ | Example 9-(5) |
| Compound 23 | 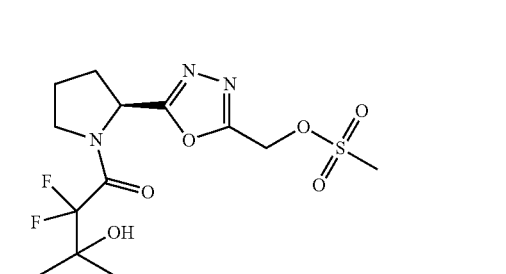 | 1,000~2,000 | 502 (M + Na)+ | Example 9-(6) |

TABLE 1-4-continued

| Compound 24 | (structure) | 218 | 530 (M + Na)+ | As in Example 9 |

TABLE 1-5

| Compound 25 | (structure) | 401 | 530 (M + Na)+ | As in Example 9 |
| Compound 26 | (structure) | 500~1,000 | 530 (M + Na)+ | As in Example 9 |
| Compound 27 | (structure) | 500~1,000 | 386 (M + H)+ | As in Example 8 |
| Compound 28 | (structure) | 351 | 524 (M + H)+ | As in Example 8 |

TABLE 1-5-continued

| Compound 29 | (structure) | 62 | 500 (M + Na)+ | Example 9 |
| Compound 30 | (structure) | 220 | 538 (M + H)+ | As in Example 9 |

TABLE 1-6

| Compound 31 | (structure) | 389 | 531 (M + Na)+ | As in Example 9 |
| Compound 32 | (structure) | 165 | 522 (M + H)+ | As in Example 9 |
| Compound 33 | (structure) | 259 | 517 (M + H)+ | As in Example 9 |

TABLE 1-6-continued

| Compound | Structure | Activity | MS | Synthesis |
|---|---|---|---|---|
| Compound 34 | (pyrrolidine-N-C(O)-C(F)(F)-C(OH)(3,3,5,5-tetramethylcyclohexyl); pyrrolidine-2-yl connected to 1,3,4-oxadiazole-2-yl, 5-position CH2-pyridin-3-yl) | 500~1,000 | 463 (M + H)+ | As in Example 8 |
| Compound 35 | (same left side; isoxazole with 5-CH2CH2-pyridin-3-yl) | 45 | 476 (M + H)+ | As in Example 1 |
| Compound 36 | (same left side; 1,3,4-oxadiazole-CH2-O-pyrimidin-5-yl) | 1,000~2,000 | 480 (M + H)+ | As in Example 9 |
| Compound 37 | (same left side; 1,3,4-oxadiazole-CH2NH2) | 1,000~2,000 | 401 (M + H)+ | Example 10 |

TABLE 1-7

| Compound | Structure | Activity | MS | Synthesis |
|---|---|---|---|---|
| Compound 38 | (same left side; 1,3,4-oxadiazole-5-CH2-NH-C(O)-phenyl) | 500~1,000 | 505 (M + H)+ | Example 10 |

TABLE 1-7-continued

| Compound | Structure | IC50 | MS | Example |
|---|---|---|---|---|
| Compound 39 | 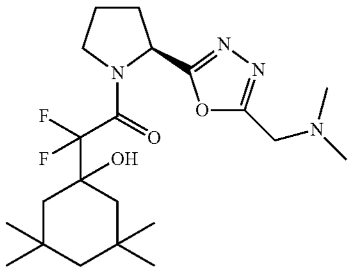 | 500~1,000 | 429 (M + H)+ | Example 11 |
| Compound 40 | 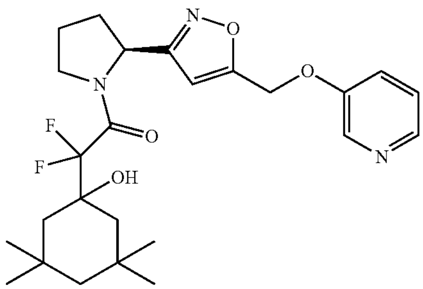 [SMILES: CC1(C)CC(C)(C)CC(O)(C(F)(F)C(=O)N2CCC[C@H]2c2cc(CCc3cccnc3)on2)C1] | 83 | 478 (M + H)+ | Example 2 |
| Compound 41 | 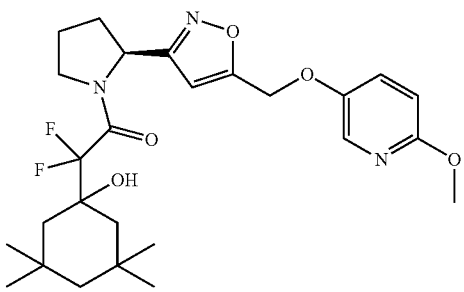 | 150 | 508 (M + H)+ | As in Example 3 |
| Compound 42 | 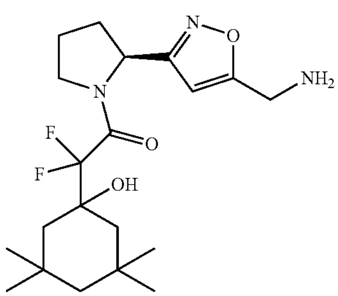 | 447 | 400 (M + H)+ | Example 4-(2) |
| Compound 43 | 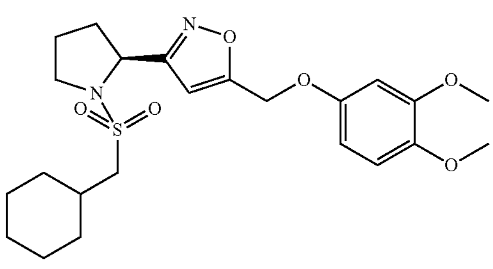 [SMILES: COc1ccc(OCc2cc([C@@H]3CCCN3S(=O)(=O)CC3CCCCC3)no2)cc1OC] | 149 | 487 (M + H)+ | Example 7 |

TABLE 1-7-continued
| Compound 44 | 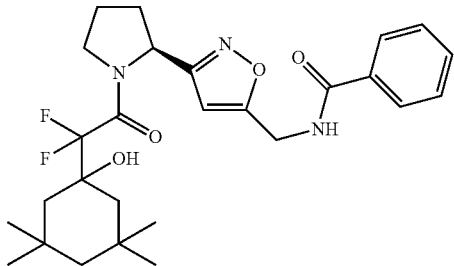 [SMILES: CC1(C)CC(C)(C)CC(O)(C(F)(F)C(=O)N2CCC[C@H]2c2cc(CNC(=O)c3ccccc3)on2)C1] | 166 | 504 (M + H)+ | Example 4 |
TABLE 1-8
| Compound 45 | 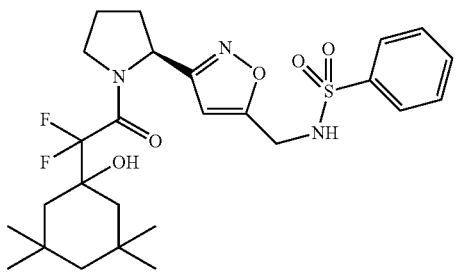 [SMILES: CC1(C)CC(C)(C)CC(O)(C(F)(F)C(=O)N2CCC[C@H]2c2cc(CNS(=O)(=O)c3ccccc3)on2)C1] | 101 | 540 (M + H)+ | Example 5 |
| Compound 46 | 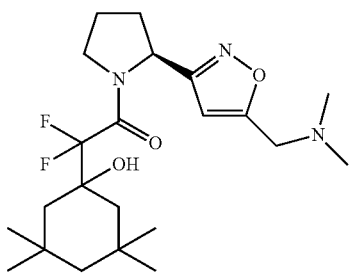 | 310 | 428 (M + H)+ | Example 6 |
| Compound 47 | 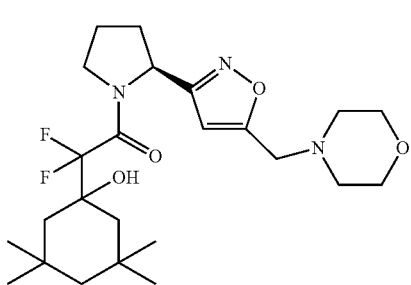 [SMILES: CC1(C)CC(C)(C)CC(O)(C(F)(F)C(=O)N2CCC[C@H]2c2cc(CN3CCOCC3)on2)C1] | 254 | 470 (M + H)+ | As in Example 6 |
| Compound 48 | 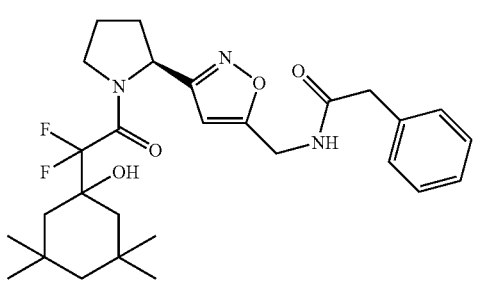 [SMILES: CC1(C)CC(C)(C)CC(O)(C(F)(F)C(=O)N2CCC[C@H]2c2cc(CNC(=O)Cc3ccccc3)on2)C1] | 94 | 518 (M + H)+ | As in Example 4 |

TABLE 1-8-continued

| Compound 49 | (structure) | 500~1,000 | 429 (M + H)+ | As in Example 2 |
| --- | --- | --- | --- | --- |
| Compound 50 | (structure) | 117 | 564 (M + H)+ | As in Example 4 |
| Compound 51 | (structure) | 74 | 578 (M + H)+ | As in Example 4 |

TABLE 1-9

| Compound 52 | (structure) | 204 | 499 (M + Na)+ | As in Example 3 |
| --- | --- | --- | --- | --- |
| Compound 53 | (structure) | 86 | 501 (M + Na)+ | Example 21 |

TABLE 1-9-continued

| Compound 54 | (structure) | 290 | 478 (M + H)+ | Example 23 |
| Compound 55 | (structure) | 228 | 501 (M + Na)+ | Example 22 |
| Compound 56 | (structure) | 328 | 479 (M + H)+ | As in Example 22 |
| Compound 57 | (structure) | 79 | 500 (M + Na)+ | As in Example 21 |
| Compound 58 | (structure) | 250 | 501 (M + Na)+ | As in Example 22 |

TABLE 1-10
| Compound 59 | 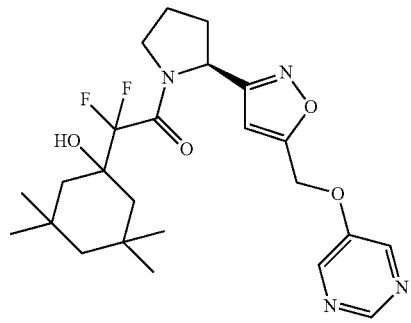 [SMILES: CC1(C)CC(C)(C)CC(O)(C(F)(F)C(=O)N2CCC[C@H]2c2cc(COc3cncnc3)on2)C1] | 124 (M + Na)+ | 501 | As in Example 3 |
|---|---|---|---|---|
| Compound 60 | 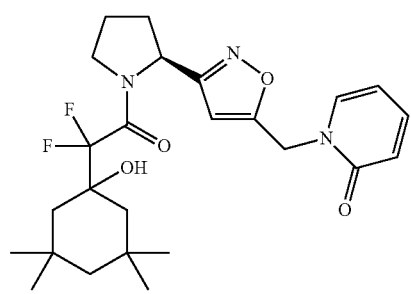 [SMILES: CC1(C)CC(C)(C)CC(O)(C(F)(F)C(=O)N2CCC[C@H]2c2cc(Cn3ccccc3=O)on2)C1] | 376 (M + Na)+ | 500 | As in Example 23 |
| Compound 61 | 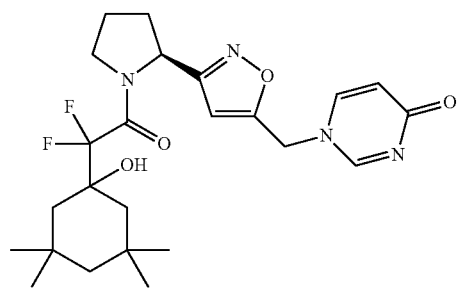 | 152 (M + H)+ | 479 | As in Example 23 |
| Compound 62 | 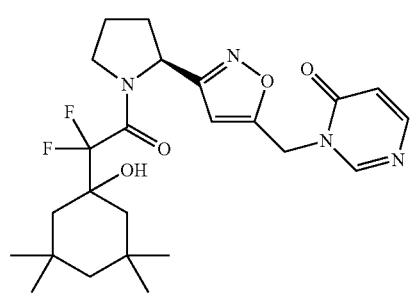 [SMILES: CC1(C)CC(C)(C)CC(O)(C(F)(F)C(=O)N2CCC[C@H]2c2cc(Cn3cnccc3=O)on2)C1] | 210 (M + H)+ | 479 | As in Example 23 |
| Compound 63 | 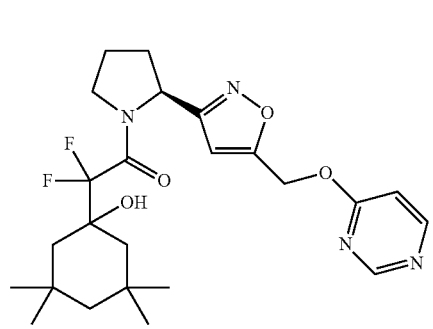 [SMILES: CC1(C)CC(C)(C)CC(O)(C(F)(F)C(=O)N2CCC[C@H]2c2cc(COc3ccncn3)on2)C1] | 185 (M + H)+ | 479 | As in Example 23 |

TABLE 1-10-continued

| Compound 64 | (structure) | 182 | 517 (M + Na)+ | As in Example 3 |
| Compound 65 | (structure) | 241 | 513 (M + Na)+ | As in Example 3 |

TABLE 1-11

| Compound 60 | (structure) | 122 | 478 (M + H)+ | As in Example 23 |
| Compound 67 | (structure) |  | 478 (M + H)+ | Example 24 |

(Test 1) Test for Measuring Immunophilin FKBP12 Rotamase Activity

The rotamase (peptidylprolyl isomerase) inhibiting activity of each test compound was measured by a known method (Harding et al., Nature 341, 758-760, 1989; Holts et al., J. Am. Chem. Soc. 115, 9925-9938, 1993.) To be more specific, a plastic cuvette was charged with 35 mM HEPES (pH 7.8), 12 nM human recombinant FKBP12 (Sigma, F-5398), 0.4 mg/mL α-chymotrypsin, and a test compound dissolved in DMSO at varying concentrations (DMSO's final concentration was 0.1%.) Subsequently, 24 mM of the substrate peptide, succinyl-Ala-Phe-Pro-Phe-paranitroanilide, as dissolved in trifluoroethanol containing 500 mM of LiCl was added to give a final concentration of 48 μM, whereupon reaction started. The reaction was carried out at 4° C. and the change in absorbance at 390 nm accompanying the liberation of the paranitroaniline product was monitored. A calculated initial rate minus the corresponding value in the absence of the enzyme was used as an index of rotamase activity. The rotamase inhibiting activity of a test compound was expressed in relative values (%) with respect to the control value of rotamase activity in the absence of the compound, and the concentration of the compound at which it was capable of inhibiting rotamase activity by 50% was calculated as an $IC_{50}$ value from its concentration response curve.

The IC$_{50}$ values of the respective test compounds are indicated in Table 1-1 to Table 1-11.

(Test 2) Dissolution Test

To 5 g of 1,3-butylene glycol, 10 g of water was added and the mixture was stirred until homogeneity; thereafter, ethanol was added to make a total volume of 100 mL, whereby a base was prepared. An excess amount of a test compound was put into a test tube, the prepared base was added, and the mixture was stirred at 25° C. for 7 days and passed through a membrane filter (0.45 µm); the resulting filtrate was diluted with acetonitrile and the concentration of the diluted solution was measured by HPLC to determine the solubility of the compound.

A comparative example (1-[2-((2S)-2-[5-(3,4-dimethoxyphenoxy)methyl]-1,2,4-oxadiazol-3-yl]pyrrolidin-1-yl)-1,1-difluoro-2-oxoethyl]-3,3,5,5-tetramethylcyclohexanol, disclosed in WO2008/075735) had a solubility of 30.8 mg/mL whereas Compound 1 had a solubility of 57.5 mg/mL.

(Test 3) Test for Measuring Hair Development Stimulating Effect in Shaven Mouse Model Method C57BL mice (female, ca. 7-wk old) were shaven on the back and the base prepared in Test 2 or a solution prepared by dissolving 5% (w/v) of Compound 1 in this base was administered by applying them to the shaven area in 200-µL portions once daily starting 3 days after the shaving (each group consisting of 10 heads.) Every 2 or 3 days after the start of the administration, the state of hair development in the shaven area was scored in accordance with the following criteria.

Criteria for scoring the hair development:
1=No hair development.
2=Hair development in less than 30% of the shaven area.
3=Hair development in at least 30% but less than 60% of the shaven area.
4=Hair development in at least 60% but less than 90% of the shaven area.
5=Hair development in at least 90% of the shaven area.

Results

As FIG. 1 shows, the group administered with the solution of 5% Compound 1 had their hair development scores increased earlier than the group administered with the base. The hair development scores in the Compound 1 administered group were higher than those in the base administered group at day 15 of the administration and onward in the test period. It therefore became clear that the test compound showed a superior hair development stimulating effect. Such superior hair development stimulating effect is exhibited by the combination of various properties including not only the rotamase inhibiting effect of the compound but also its good stability, absorbability, and disposition.

(Test 4) Dissolution Test

To 79 mL of ethanol, water was added to give a total volume of 100 mL, whereby a base was prepared. An excess amount of a test compound was put into a test tube, the prepared base was added, and the mixture was stirred at 5° C. for 3 days and passed through a membrane filter (0.45 µm); the resulting filtrate was diluted with acetonitrile and the concentration of the diluted solution was measured by HPLC to determine the solubility of the compound. Compound 40 had a solubility of 113.2 mg/mL.

(Test 5) Test for Measuring Hair Development Stimulating Effect in Shaven Mouse Model Method C57BL mice (female, ca. 7-wk old) were shaven on the back and the base prepared in Test 4 or a solution prepared by dissolving 5% (w/v) of Compound 40 in this base was administered by applying them to the shaven area in 200-µL portions once daily starting 3 days after the shaving (each group consisting of 10 heads.) Every 2 or 3 days after the start of the administration, the state of hair development in the shaven area was scored in accordance with the criteria described in Test 3.

Results

Figure 2:
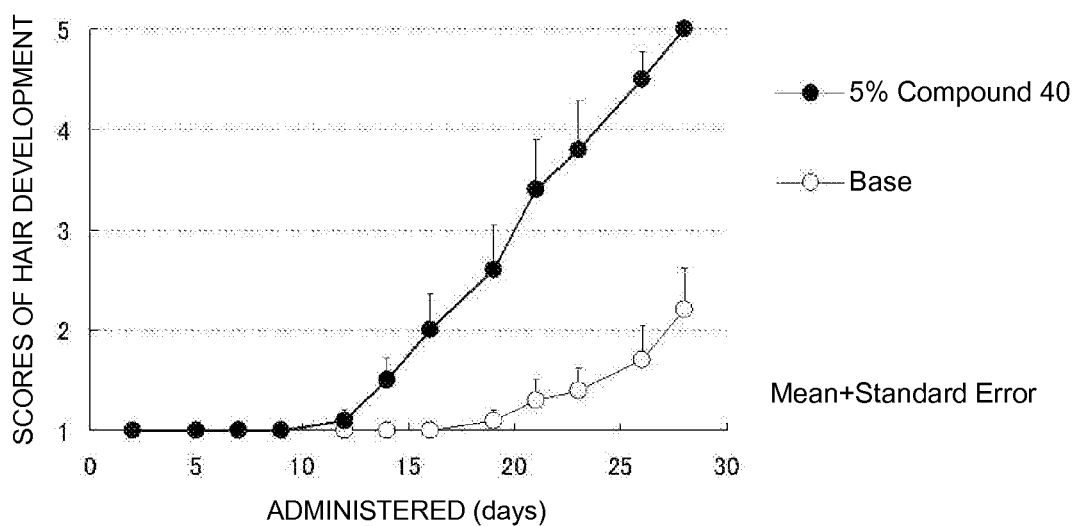
FIG. 2 shows the hair development stimulating effect of Compound 40 in shaven mouse models.

As FIG. 2 shows, the group administered with the solution of 5% Compound 40 had their hair development scores increased earlier than the group administered with the base. The hair development scores in the Compound 40 administered group were higher than those in the base administered group at day 15 of the administration and onward in the test period. It therefore became clear that the test compound showed a superior hair development stimulating effect.

The superior hair development stimulating effect of Compound 40 is exhibited by the combination of various properties including not only the rotamase inhibiting effect of the compound but also its good stability, absorbability, and disposition.

(Test 6) Test for Measuring Anagen Induction Stimulating Effect in Shave Mouse Model Method It is known that as the hair cycle of the mouse skin makes a transition from the telogen to the anagen phase and as the anagen phae proceeds, the number of proliferating cell nuclear antigen (PCNA) positive cells in the hair follicle increases (Cravens et al., J. Endocrinol., 191, 415-425, 2006) and, hence, the increase in the quantity of PCNA is one of the markers for the induction of the anagen phase.

The anagen induction stimulating effect of a compound was measured by the following method with the quantity of skin PCNA being used as an index.

C57BL mice (female, ca. 7-wk old) were shaven on the back and a base (80% ethanol) or a solution prepared by dissolving 5% (w/v) of Compound 40, 52, 59, 61, 63, 64 or 66 in this base was administered by applying them to the shaven area in 200-µL portions once daily for 2 days starting 3 days after the shaving (each group consisting of 5 heads.) About 4 hours after the administration on the second day, the skin at the application site was sampled and homogenized in a buffer containing 50 mM Tris-HCl (pH 7.6), 150 mM NaCl, 1% NP-40, and a protease inhibitor. By a centrifugal separation procedure, a PCNA containing protein solution was prepared and the quantity of PCNA in the solution was measured with a PCNA-ELISA kit of Calbiochem, Inc.

Results

Figure 3:
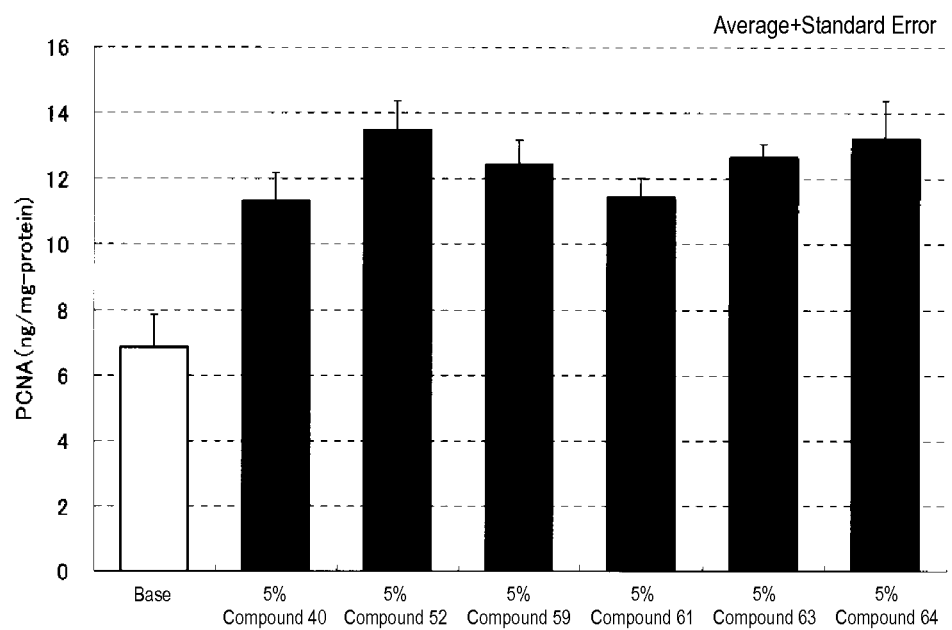
FIG. 3 shows the anagen induction stimulating effect of Compounds 40, 52, 59, 61, 63, and 64 in shaven mouse models.

As FIG. 3 shows, the group administered with Compound 40 which showed a hair development stimulating effect in Test 5 showed higher values for the quantity of skin PCNA than the group administered with the base. It therefore became clear that the test compound showed a superior anagen induction stimulating effect in the early stage following the start of administration.

Like the group administered with Compound 40, the groups administered with the solutions of Compounds 52, 59, 61, 63, and 64 also showed increases in the quantity of skin PCNA. It therefore became clear that each of these compounds showed an anagen induction stimulating effect (FIG. 3.)

The same test was conducted on the group administered with Compound 66, which showed skin PCNA levels approximately 1.4 times higher than those in the group administered with the base.

The superior anagen induction stimulating effect of these compounds is exhibited by the combination of various properties including not only the rotamase inhibiting effect of the compounds but also their good stability, absorbability, and disposition.

INDUSTRIAL APPLICABILITY

The present invention enables providing novel compounds that bind to FKBP12 or pharmaceutically acceptable salts thereof, as well as new therapeutics useful in the prevention or treatment of alopecia which comprise those compounds or pharmaceutically acceptable salts thereof.

The invention claimed is:

1. A compound represented by formula (1)

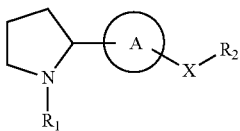

(1)

[where $R_1$ represents either the following formula (2) or (3)

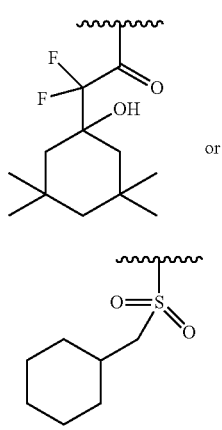

ring A represents either one of the rings represented by the following formula (5)

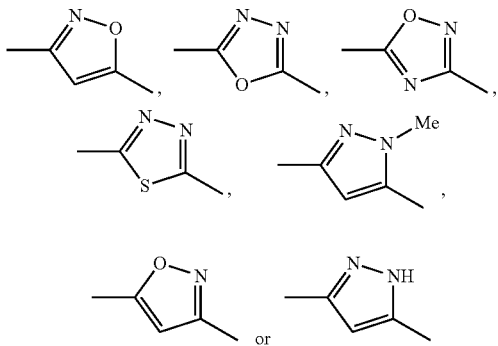

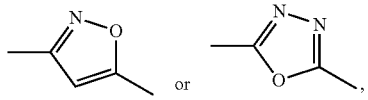

(5)

X represents $—(CH_2)_m—X_1—(CH_2)_n—$;

$X_1$ represents —O—;

m and n which may be the same or different each represent an integer of 0-3;

$R_2$ represents an aryl group, a heteroaryl group (said aryl or heteroaryl group may be substituted by 1-3 substituent groups selected from the group consisting of a halogen atom, a $C_{1-6}$ alkyl group, and a $C_{1-6}$ alkoxy group (said $C_{1-6}$ alkyl group or $C_{1-6}$ alkoxy group may be substituted by 1-3 substituent groups selected from the group consisting of a halogen atom and a hydroxy group)), a 1,3-benzodioxolanyl group, an indolyl group, a morpholyl group, a hydroxy group, a $C_{1-6}$ alkyl group (said $C_{1-6}$ alkyl group may be substituted by 1-2 hydroxy groups), an amino group, a mono-$C_{1-6}$ alkylamino group, a di-$C_{1-6}$ alkylamino group, a $C_{1-6}$ alkoxy group, a $C_{1-6}$ alkylsulfonyloxy group, a pyridonyl group, or a pyrimidinonyl group] or a pharmaceutically acceptable salt thereof.

2. The compound or pharmaceutically acceptable salt thereof according to claim 1, wherein X is —CH$_2$O— or —O—.

3. The compound or pharmaceutically acceptable salt thereof according to claim 1, wherein X is —CH$_2$O.

4. The compound or pharmaceutically acceptable salt thereof according to claim 1, wherein $R_1$ is formula (2).

5. The compound or pharmaceutically acceptable salt thereof according to claim 1, wherein $R_2$ is a phenyl group, a pyridyl group, a pyridazinyl group or a pyrimidyl group (said phenyl group, pyridyl group or pyrimidyl group may be substituted by 1-3 halogen atoms or methoxy groups), a pyridonyl group, or a pyrimidinonyl group.

6. The compound or pharmaceutically acceptable salt thereof according to claim 5, wherein $R_2$ is a phenyl group or a pyridyl group (said phenyl group or pyridyl group may be substituted by 1-3 methoxy groups).

7. The compound according to claim 1, which is (S)-1-(2-(5-((3,4-dimethoxyphenoxy)methyl)isoxazol-3-yl)pyrrolidin-1-yl)-2,2-difluoro-2-(1-hydroxy-3,3,5,5-tetramethylcyclohexyl)ethanone,
(S)-2,2-difluoro-2-(1-hydroxy-3,3,5,5-tetramethylcyclohexyl)-1-(2-(5-((pyridin-3-yloxy)methyl)isoxazol-3-yl)pyrrolidin-1-yl)ethanone,
(S)-1-(2-(5-((3,4-dimethoxyphenoxy)methyl)-1,3,4-oxadiazol-2-yl)pyrrolidin-1-yl)-2,2-difluoro-2-(1-hydroxy-3,3,5,5-tetramethylcyclohexyl)ethanone,
(S)-2,2-difluoro-2-(1-hydroxy-3,3,5,5-tetramethylcyclohexyl)-1-(2-(5-(phenoxymethyl)-1,3,4-oxadiazol-2-yl)pyrrolidin-1-yl)ethanone,
(S)-2,2-difluoro-2-(1-hydroxy-3,3,5,5-tetramethylcyclohexyl)-1-(2-(5-((pyrimidin-4-yloxy)methyl)isoxazol-3-yl)pyrrolidin-1-yl)ethanone,
a pharmaceutically acceptable salt thereof.

8. A pharmaceutical comprising as an active ingredient the compound or pharmaceutically acceptable salt thereof according to claim 1 and a pharmaceutically acceptable carrier.

9. A method of treating alopecia which comprises applying the compound or pharmaceutically acceptable salt thereof according to claim 1 to a patient.

10. (S)-1-(2-(5-((3,4-dimethoxyphenoxy)methyl)isoxazol-3-yl)pyrrolidin-1-yl)-2,2-difluoro-2-(1-hydroxy-3,3,5,5-tetramethylcyclohexyl)ethanone represented by the following formula:

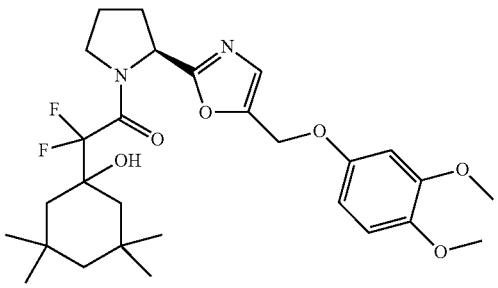

or a pharmaceutically acceptable salt thereof.

11. (S)-1-(2-(5-((3,4-Dimethoxyphenoxy)methyl)-1,3,4-oxadiazol-2-yl)pyrrolidin-1-yl)-2,2-difluoro-2-(1-hydroxy-3,3,5,5-tetramethylcyclohexyl)ethanone represented by the following formula:

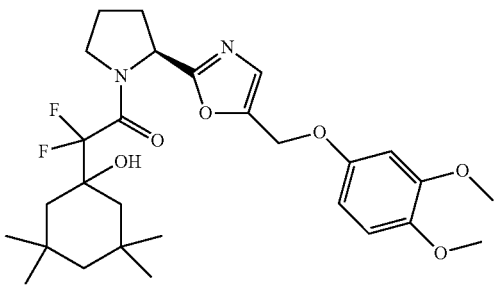

or a pharmaceutically acceptable salt thereof.

12. (S)-2,2-Difluoro-2-(1-hydroxy-3,3,5,5-tetramethylcyclohexyl)-1-(2-(5-((3,4,5-trimethoxyphenoxy)methyl)isoxaol-3-yl)pyrrolidin-1-yl)ethanone represented by the following formula:

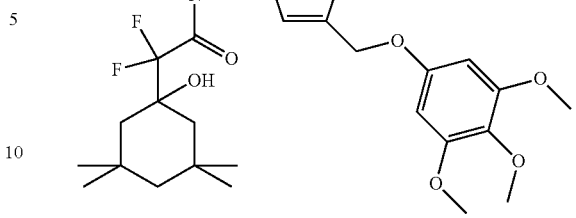

or a pharmaceutically acceptable salt thereof.

13. (S)-2,2-Difluoro-2-(1-hydroxy-3,3,5,5-tetramethylcyclohexyl)-1-(2-(5-(phenoxymethyl)-1,3,4-oxadiazol-2-yl)pyrrolidin-1-yl)ethanone or a pharmaceutically acceptable salt thereof.

14. (S)-2,2-Difluoro-2-(1-hydroxy-3,3,5,5-tetramethylcyclohexyl)-1-(2-(5-((pyridin-3-yloxy)methyl)isoxazol-3-yl)pyrrolidin-1-yl)ethanone represented by the following formula:

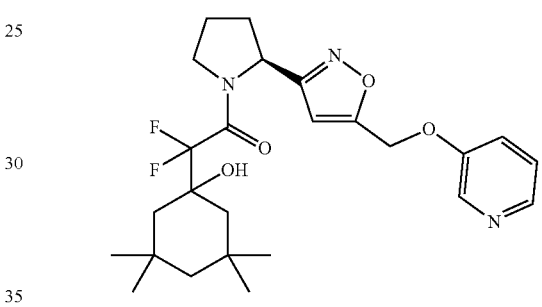

or a pharmaceutically acceptable salt thereof.

15. (S)-2,2-Difluoro-2-(1-hydroxy-3,3,5,5-tetramethylcyclohexyl)-1-(2-(5-((pyridin-4-yloxy)methyl)isoxazol-3-yl)pyrrolidin-1-yl)ethanone or a pharmaceutically acceptable salt thereof.

16. A pharmaceutical comprising as an active ingredient the compound or pharmaceutically acceptable salt thereof according to any one of claims 10 to 15 and a pharmaceutically acceptable carrier.

* * * * *